United States Patent
Shchepinov

(10) Patent No.: US 11,166,930 B2
(45) Date of Patent: Nov. 9, 2021

(54) ISOTOPICALLY MODIFIED COMPONENTS AND THERAPEUTIC USES THEREOF

(71) Applicant: RETROTOPE, INC., Los Altos, CA (US)

(72) Inventor: Mikhail Sergeevich Shchepinov, Kingston Upon Thames (GB)

(73) Assignee: RETROTOPE, INC., Los Altos, CA (US)

( * ) Notice: Subject to any disclaimer, the term of this patent is extended or adjusted under 35 U.S.C. 154(b) by 0 days.

(21) Appl. No.: 16/348,087

(22) PCT Filed: Nov. 16, 2017

(86) PCT No.: PCT/US2017/062107
§ 371 (c)(1),
(2) Date: May 7, 2019

(87) PCT Pub. No.: WO2018/094116
PCT Pub. Date: May 24, 2018

(65) Prior Publication Data
US 2019/0282529 A1 Sep. 19, 2019

Related U.S. Application Data

(60) Provisional application No. 62/423,699, filed on Nov. 17, 2016.

(51) Int. Cl.
*A61K 31/22* (2006.01)
*A61K 31/215* (2006.01)
(Continued)

(52) U.S. Cl.
CPC ............ *A61K 31/202* (2013.01); *A61B 5/055* (2013.01); *A61B 5/4848* (2013.01);
(Continued)

(58) Field of Classification Search
CPC ... A61K 31/202; A61K 31/232; A61K 31/375
(Continued)

(56) References Cited

U.S. PATENT DOCUMENTS 6,331,532 B1  12/2001  Murphy et al.
7,179,928 B2   2/2007  Smith et al.
(Continued)

FOREIGN PATENT DOCUMENTS

WO  2018/094116  5/2018

OTHER PUBLICATIONS

Berkowitz et al. (Dec. 2015) "Measuring In Vivo Free Radical Production by the Outer Retina", Investigative Ophthalmology & Visual Science, 56:7931-7938.
(Continued)

*Primary Examiner* — Shengjun Wang
(74) *Attorney, Agent, or Firm* — Mintz, Levin, Cohn, Ferris, Glovsky and Popeo, P.C.

(57) ABSTRACT

Methods are provided of identifying a subject having impaired aldehyde dehydrogenase activity; and administering to the subject a compound comprising an isotopically-modified polyunsaturated fatty acid, an isotopically-modified polyunsaturated fatty acid ester, an isotopically-modified polyunsaturated fatty acid thioester, an isotopically-modified polyunsaturated fatty acid amide, a polyunsaturated fatty acid mimetic, or an isotopically-modified polyunsaturated fatty acid pro-drug, the compound having an isotopic modification that reduces oxidation of the compound, thereby reducing production in the subject of substrate for aldehyde dehydrogenase. Some aspects provide coadministering an isotopically-modified polyunsaturated fatty acid and an oxylipin.

27 Claims, 7 Drawing Sheets

(51) Int. Cl.

| | |
|---|---|
| *A61K 31/20* | (2006.01) |
| *A61K 31/202* | (2006.01) |
| *A61P 25/28* | (2006.01) |
| *A61B 5/055* | (2006.01) |
| *A61B 5/00* | (2006.01) |
| *G01N 33/573* | (2006.01) |
| *G01N 33/68* | (2006.01) |
| *C12Q 1/32* | (2006.01) |
| *A61P 25/00* | (2006.01) |
| *A61K 31/375* | (2006.01) |
| *A61K 31/557* | (2006.01) |
| *A61K 31/66* | (2006.01) |
| *A61K 31/122* | (2006.01) |
| *A61K 31/355* | (2006.01) |

(52) U.S. Cl.
CPC .......... *A61K 31/122* (2013.01); *A61K 31/355* (2013.01); *A61K 31/375* (2013.01); *A61K 31/557* (2013.01); *A61K 31/66* (2013.01); *A61P 25/00* (2018.01); *A61P 25/28* (2018.01); *C12Q 1/32* (2013.01); *G01N 33/573* (2013.01); *G01N 33/6896* (2013.01); *C07B 2200/05* (2013.01); *G01N 2333/90203* (2013.01)

(58) Field of Classification Search
USPC ........................................ 514/549, 530, 560
See application file for complete search history.

(56) References Cited

U.S. PATENT DOCUMENTS

| | | | |
|---|---|---|---|
| 7,232,809 | B2 | 6/2007 | Murphy et al. |
| 7,432,305 | B2 | 10/2008 | Miller et al. |
| 7,470,798 | B2 | 12/2008 | Wang et al. |
| 7,514,461 | B2 | 4/2009 | Wang et al. |
| 7,888,334 | B2 | 2/2011 | Murphy et al. |
| 7,888,335 | B2 | 2/2011 | Taylor et al. |
| 2002/0052342 | A1 | 5/2002 | Murphy et al. |
| 2002/0081689 | A1 | 6/2002 | Yan et al. |
| 2003/0032078 | A1 | 2/2003 | Travis |
| 2003/0069208 | A1 | 4/2003 | Murphy et al. |
| 2004/0106579 | A1 | 6/2004 | Murphy et al. |
| 2005/0043553 | A1 | 2/2005 | Smith et al. |
| 2005/0245487 | A1 | 11/2005 | Murphy et al. |
| 2006/0229278 | A1 | 10/2006 | Taylor et al. |
| 2007/0238709 | A1 | 10/2007 | Murphy et al. |
| 2007/0270381 | A1 | 11/2007 | Murphy et al. |
| 2008/0161267 | A1 | 7/2008 | Taylor et al. |
| 2008/0275005 | A1 | 11/2008 | Murphy et al. |
| 2009/0258841 | A1 | 10/2009 | Murphy et al. |
| 2009/0280516 | A1 | 11/2009 | Chen et al. |
| 2010/0029706 | A1 | 2/2010 | Miller et al. |
| 2010/0056643 | A1 | 3/2010 | Bachynsky et al. |
| 2011/0046219 | A1 | 2/2011 | Hiinman et al. |
| 2011/0105609 | A1* | 5/2011 | Shchepinov .......... C07B 59/001 514/549 |
| 2012/0005765 | A1* | 1/2012 | Kumar ............... A61K 49/0008 800/3 |
| 2013/0309330 | A1* | 11/2013 | Mastronardi ........ A61K 31/216 424/722 |
| 2014/0044693 | A1* | 2/2014 | Shchepnov .......... A61K 31/231 424/94.1 |
| 2014/0050712 | A1 | 2/2014 | Shchepinov |
| 2014/0147428 | A1 | 5/2014 | Shchepinov |

OTHER PUBLICATIONS

Berkowitz et al. (Feb. 2016) "MRI of Retinal Free Radical Production With Laminar Resolution In Vivo". Investigative Ophthalmology & Visual Science, 57(2):577-585.

D'Souza et al. (2015) "Characterization of Aldh2-/-Mice as an Age-related Model of Cognitive impairment and Alzheimer's Disease", Molecular Brain, 8(27): 16 pages.
Fitzmaurice et al. {Jan. 8, 2013, e-Published (Dec. 24, 2012)} "Aldehyde Dehydrogenase Inhibition as a Pathogenic Mechanism in Parkinson Disease". Proceedings of the National: Academy of Sciences of the United States of America, 110(2):636-641.
GenBank (Aug. 1, 1997) "aldehydedehydrogenase 1 [*Homo sapiens*]", Accession No. AAC51 652.1,. 2 pages.
GenBank (Mar. 18, 2009) "aldehyde dehydrogenase 1 family, member A1 [Rattus norvegicus]". Accession No. AAH61526.1, 2 pages.
GenBank (Jul. 15, 2006) "aldehyde dehydrogenase 2 family (mitochondrial) [*Homo sapiens*]", Accession No. AAH02967.1.2 pages.
GenBank (Jun. 9, 2008) "aldehyde dehydrogenase 3 family, member A1 [Rattus norvegicus]", Accession No. AAH70924.1, 2 pages.
GenBank (Aug. 4, 2008) "aldehyde dehydrogenase 5 family, member A1 [*Homo sapiens*]", Accession No. AAH34321.1,2pages.
GenBank (Jul. 23, 1993) "aldehyde Dehydrogenase Isozyme 3 [*Homo sapiens*]", Accession No. AAB26658.1,2 pages.
GenBank (Dec. 12, 2020) "aldehyde dehydrogenase X, mitochondrial precursor [Homo sapiens]", Accession No. NP_000683.3, 3 pages.
GenBank (Dec. 7, 2020) "aldehyde dehydrogenase, dimeric NADP-preferring isoform 1 [Mus muscuius]", Accession No. NP_001106196.1,3 pages.
GenBank (Jan. 18, 2021) "aldehyde dehydrogenase, mitochondrial isoform 1 precursor [*Homo sapiens*]", Accession No. NP_000681.2,4 Pages.
GenBank (Jan. 18, 2021) "aldehyde dehydrogenase, mitochondrial isoform 1 precursor [Mus muscuius]", Accession No. NP_033786.1, 4 Pages.
GenBank (Feb. 3, 2021) "aldehyde dehydrogenase, mitochondrial precursor [Rattus norvegicus]", Accession No. NP_115792.2, 3 pages.
GenBank (Feb. 13, 1997) "mp44a.12.r1 Barstead MPLRB1 Mus muscuius cDNA clone IMAGE:572062 5' similar to GB:M31690 Mouse argininosuccinate synthetase (MOUSE), mRNA sequence", Accession No. AA105194.1,2 pages.
Gould et al. (Nov. 1986) "Salt Selection for Basic Drugs", International Journal of Pharmaceutics, 33(1-3):201-217.
Larson et al., (Aug. 26, 2005) "Disruption of the Coenzyme Binding Site and Dimer Interface Revealed in the Crystal Structure of Mitochondrial Aldehyde Dehydrogenase "Asian" Variant", The Journal of Biological Chemistry, 280 (34):30550-30556.
Li et al. (2006) "Mitochondrial Aldehyde Dehydrogenase-2 (ALDH2) Glu504Lys Polymorphism Contributes to the Variation in Efficacy' of Sublingual Nitroglycerin", The Journal of Clinical Investigation, 116:506-511.
Marchitt et al. (Jun. 2007) "Neurotoxicity and Metabolism of the Catecholamine-Derived 3,4-Dihydroxyphenylacetaldehyde and 3,4-Dihydroxyphenylglycolaldehyde: The Role of Aldehyde Dehydrogenase", Pharmacological Reviews, 59(2): 125-50.
Marchitt et al. (Jun. 2008) "Non-P450 Aldehyde Oxidizing Enzymes: The Aldehyde Dehydrogenase Superfamily", Expert Opinion on Drug Metabolism & Toxicology, 4(6):697-720 (37 pages).
McClements et al. (Oct. 2007) "Emulsion-based delivery systems for lipophilic bioactive components", Journal of Food Science, 72(8):R109-R124.
Nema et al. (May-Jun. 2011) "Excipients and their Role in Approved Injectable Products: Current Usage and Future Directions", PDA Journal of Pharmaceutical Science and Technology, 65{3}:287-332.
Porter et al. (2007) "Lipids and Lipid-based Formulations: Optimizing the Oral Delivery of Lipophilic Drugs", Nature Reviews Drug Discovery. 6(3)231-248.
Powell et al. (Sep./Oct. 1993) "Compendium of Excipients for Parenteral Formulations", PDA Journal of Pharmaceutical Science and Technology, 52(5):238-311.
Takeshita et al. (Sep. 2004) "Characterization of the Three Genotypes of Low Km Aldehyde Dehydrogenase in a Japanese Population", Human Genetics, 94(3):217-223.

(56) References Cited

OTHER PUBLICATIONS

Wey et al. (Feb. 2012) "Neurodegeneration and Motor Dysfunction in Mice Lacking Cytosolic and Mitochondriai Aldehyde Dehydrogenases: Implications far Parkinson's Disease", PLoS One, 7(2):e31522 (11 pages).
Yu et al. (Nov. 2009) "Characteristics of Aldehyde Dehydrogenase 2 (Aldh2) Knockout Mice", Toxicology Mechanismsand Methods, 19(9)535-540.
Zheng et al. (2016) "Impact of Lipid Content on the Ability of Excipient Emulsions to Increase Carotenoid Bioaccessibility from Natural Sources (Raw and Cooked Carrots)", Food Biophysics, 11:71-80.

* cited by examiner

1A

1B

1C

FIG. 7
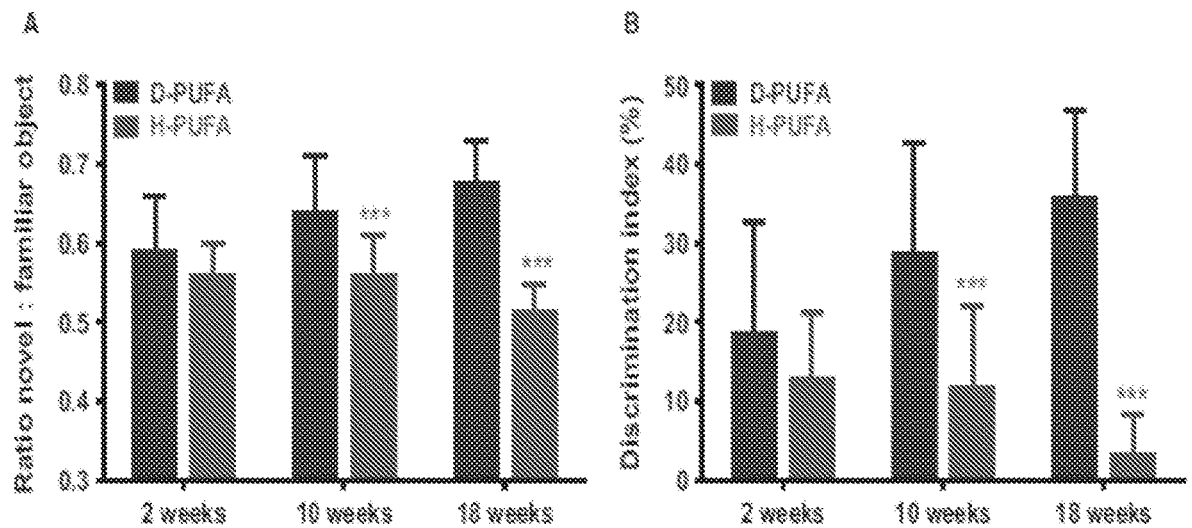
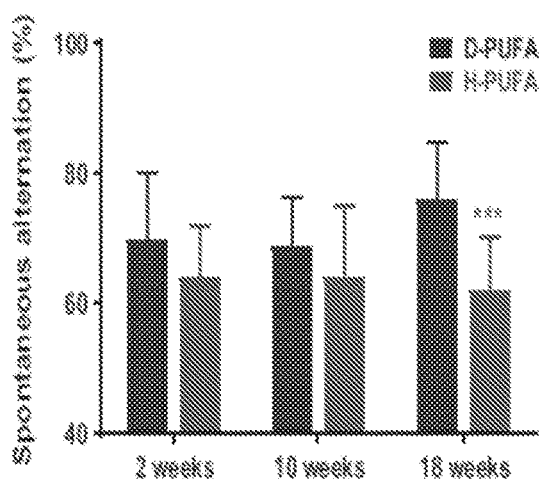
FIG. 8
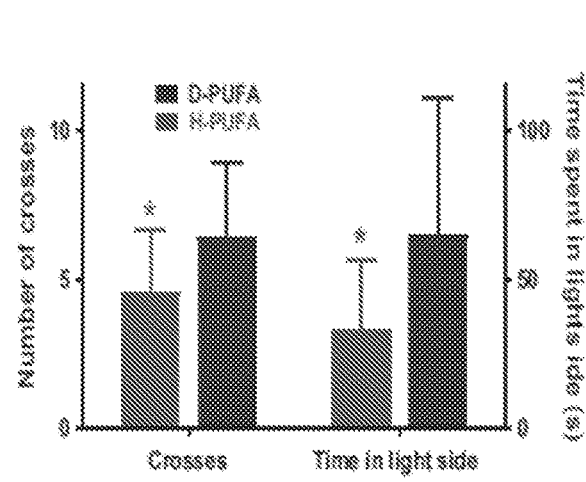
FIG. 9

ISOTOPICALLY MODIFIED COMPONENTS AND THERAPEUTIC USES THEREOF

INCORPORATION BY REFERENCE TO ANY PRIORITY APPLICATIONS

This application is the U.S. national phase under 35 U.S.C. § 371 of International Application No. PCT/US2017/062107, entitled "Isotopically Modified Components and Therapeutic Uses Thereof," filed Nov. 16, 2017, which claims the benefit of U.S. Provisional Application No. 62/423,699, filed Nov. 17, 2016, the disclosure of which is incorporated herein by reference in its entirety.

BACKGROUND

Field

Isotopically modified compounds and their pharmaceutical or nutritional uses in preventing or treating disease such as neuropathy are provided.

Description of the Related Art

Aldehyde dehydrogenases (ALDH) constitute a family of enzymes that play a critical role in detoxification of various cytotoxic xenogenic and biogenic aldehydes. There are at least 19 members/isozymes of the ALDH family, where the various isozymes may exhibit different substrate specificity and/or cellular location relative to other members of the family.

Cytotoxic aldehydes derive from a variety of sources. For example, environmental (external) sources of aldehydes include those that result from ethanol consumption, from consumption of food sources, from ingestion of hazardous materials such as vinyl chloride, pesticides, herbicides, etc., or from inhalation of hazardous materials such as those found in cigarette smoke, industrial pollution, etc. Aldehydes that may be cytotoxic can also be produced biologically (e.g., endogenously), e.g., as a result of oxidative stress such as occurs in ischemia, irradiation, or metabolism or bioconversion of cellular precursors such as neurotransmitters and drugs. Accumulation of cytotoxic levels of aldehydes, and/or defects in the ALDH enzyme, have been implicated in a variety of diseases and conditions, or in increased risk of disease development.

SUMMARY OF INVENTION

Some embodiments relate to a method, the method including identifying a subject having impaired aldehyde dehydrogenase activity, and administering to the subject a compound comprising an isotopically-modified polyunsaturated fatty acid, an isotopically-modified polyunsaturated fatty acid ester, an isotopically-modified polyunsaturated fatty acid thioester, an isotopically-modified polyunsaturated fatty acid amide, a polyunsaturated fatty acid mimetic, or an isotopically-modified polyunsaturated fatty acid pro-drug, the compound having an isotopic or chemical modification that reduces oxidation of the compound, thereby reducing production in the subject of substrate for aldehyde dehydrogenase.

Some embodiments relate to a method of preventing or ameliorating a side effect of an isotopically modified polyunsaturated lipid in a subject, comprising administering the isotopically modified polyunsaturated lipid and an oxylipin to the subject.

Some embodiments relate to a method of reversing, preventing or reducing a disruption to a metabolic pathway involving cyclooxygenase in a subject, comprising administering the isotopically modified polyunsaturated lipid and an oxylipin to the subject.

Some embodiments relate to a method of reversing, preventing or reducing an inhibition to an enzymatic process involving cyclooxygenase in a subject, comprising administering the isotopically modified polyunsaturated lipid and an oxylipin to the subject.

Some embodiments relate to a method, comprising performing a variable magnetic resonance procedure on a patient after receiving a course of isotopically modified polyunsaturated lipid therapy to measure post-treatment neuronal oxidative stress in the patient.

Some embodiments relate to a method of treating a subject having a neuropathy or neurodegenerative disease comprising: 1) identifying the subject having an impaired aldehyde dehydrogenase activity; and 2) administering to the identified subject an effective amount of a compound comprising an isotopically-modified polyunsaturated fatty acid, an isotopically-modified polyunsaturated fatty acid ester, an isotopically-modified fatty acid thioester, an isotopically-modified polyunsaturated fatty acid amide, a polyunsaturated fatty acid mimetic, or an isotopically-modified polyunsaturated fatty acid pro-drug, the compound having an isotopic or chemical modification that reduces oxidation, thereby reducing accumulation of one or more metabolic products associated with the aldehyde dehydrogenase.

Some embodiments relate to a method of treating a subject having an oxidative retinal disease comprising: 1) identifying the subject having an impaired retinol dehydrogenase activity; and 2) administering to the identified subject an effective amount of a compound comprising an isotopically-modified polyunsaturated fatty acid, an isotopically-modified polyunsaturated fatty acid ester, an isotopically-modified fatty acid thioester, an isotopically-modified polyunsaturated fatty acid amide, a polyunsaturated fatty acid mimetic, or an isotopically-modified polyunsaturated fatty acid pro-drug, the compound having an isotopic or chemical modification that reduces oxidation, thereby reducing accumulation of one or more metabolic products associated with the retinol dehydrogenase.

Some embodiments relate to a therapeutically effective amount of a compound for use in reducing or preventing accumulation of one or more metabolic products associated with the aldehyde dehydrogenase, wherein the compound comprising an isotopically-modified polyunsaturated fatty acid, an isotopically-modified polyunsaturated fatty acid ester, an isotopically-modified polyunsaturated fatty acid thioester, an isotopically-modified fatty acid amide, a polyunsaturated fatty acid mimetic, or an isotopically-modified polyunsaturated fatty acid pro-drug, the compound having an isotopic or chemical modification that reduces oxidation.

Some embodiments relate to a therapeutically effective amount of a compound for use in treating or inhibiting the progression of a neuropathy or neurodegenerative disease associated with a mutated form of a aldehyde dehydrogenase, wherein the compound comprising an isotopically-modified polyunsaturated fatty acid, an isotopically-modified polyunsaturated fatty acid ester, an isotopically-modified polyunsaturated fatty acid thioester, an isotopically-modified fatty acid amide, a polyunsaturated fatty acid mimetic, or an isotopically-modified polyunsaturated fatty acid pro-drug, the compound having an isotopic or chemical modification that reduces oxidation.

BRIEF DESCRIPTION OF THE DRAWINGS

FIG. 7A-7B show superior performance in the in the novel object recognition (NOR) task in Aldh2$^{-/-}$ mice fed the D-PUFA diet.

FIG. 8 shows the performance in the Y-maze task by Aldh2$^{-/-}$ mice fed the D-PUFA diet.

FIG. 9 shows time spent in, and number of crosses into, the illuminated chamber of the Light/Dark Box by Aldh2$^{-/-}$ mice fed the D-PUFA diet for 10 weeks.

DETAILED DESCRIPTION OF THE PREFERRED EMBODIMENT

Figure 1:
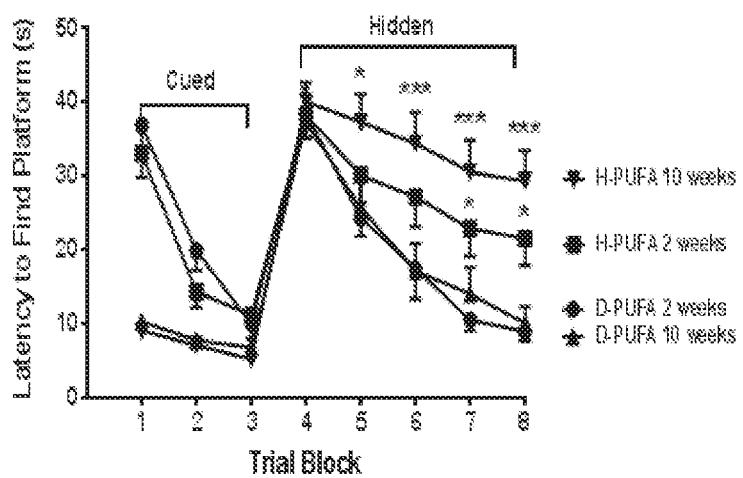
FIG. 1A shows the latency to find platforms for the Aldh2$^{-/-}$ mice in the group being fed with D-PUFA and in the group being fed with H-PUFA.
FIG. 1B shows the time in the target quadrant for the Aldh2$^{-/-}$ mice in the group being fed with D-PUFA and in the group being fed with H-PUFA.
FIG. 1C shows the number of crosses made by the Aldh2$^{-/-}$ mice in the group being fed with D-PUFA and in the group being fed with H-PUFA
Figure 1:
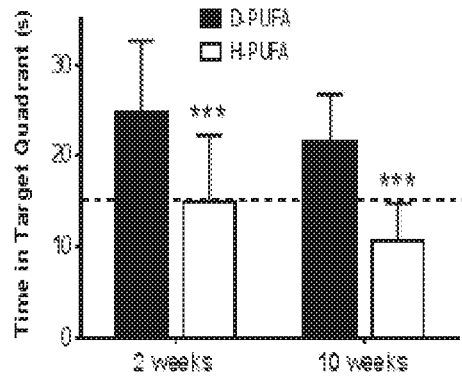
Figure 1:
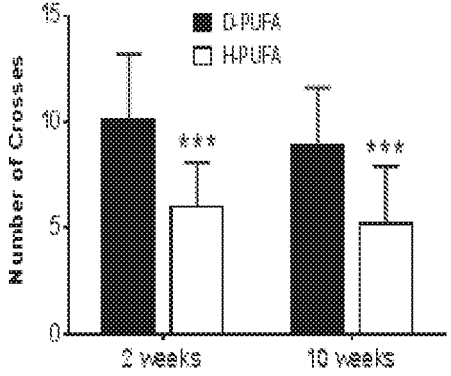

As used herein, the term "aldehyde dehydrogenase" or "ALDH" refers to an enzyme that oxidizes an aldehyde (e.g., a xenogenic aldehyde, a biogenic aldehyde, or an aldehyde produced from a compound that is ingested, inhaled, or absorbed) to its corresponding acid in an NAD$^+$-dependent or an NADP$^+$-dependent reaction. The ALDH can includes NAD(P)+-dependent enzymes catalyzing the oxidation of a wide spectrum of aliphatic and aromatic aldehyde substrates generated from various endogenous and exogenous precursors. Endogenous aldehydes are formed during metabolism of alcohols, amino acids, biogenic amines, vitamins, steroids, retinol, cholesterols, and lipids. Exogenous aldehydes are often generated from the metabolism of a number of drugs and environmental factors. For example, ALDH oxidizes aldehydes derived from the breakdown of compounds, e.g., toxic compounds that are ingested, that are absorbed, that are inhaled, that are produced as a result of oxidative stress, or that are produced during normal metabolism, e.g., conversion of retinaldehyde or retinol to retinoic acid. An example of a biogenic aldehyde is acetaldehyde produced as a product of alcohol dehydrogenase activity on ingested ethanol. An aldehyde dehydrogenase can also exhibit esterase activity and/or reductase activity. The term "ALDH" encompasses ALDH found in the cytosol, in the mitochondria, microsome, or other cellular compartment. ALDH also encompass the retinol dehydrogenase and the mitochondrial aldehyde dehydrogenase. The term "ALDH" encompasses ALDH found primarily in one or a few tissues, e.g., retinal, cornea, saliva, liver, etc., or in stem cells and embryos. The term "ALDH" encompasses any of the known ALDH isozymes, including ALDH1, ALDH1A1, ALDH1A2, ALDH1A3, ALDH1B1, ALDH1L1, ALDH1L2, ALDH2, ALDH3, ALDH3B1, ALDH3B2, ALDH4, ALDH4A1, ALDH5, ALDH5A1, ALDH6A1, ALDH7A1, ALDH8A1, ALDH9A1, ALDH16A1, ALDH18A1, AKR1b1, etc.

As used herein, "ALDH1" refers to a cytosolic aldehyde dehydrogenase that oxidizes an aldehyde (e.g., a xenogenic aldehyde, a biogenic aldehyde, or an aldehyde produced from a compound that is ingested, inhaled, or absorbed) to its corresponding acid in an NAD$^+$-dependent reaction.

The term "ALDH1" encompasses ALDH1 from various species. Amino acid sequences of ALDH1 from various species are publicly available. See, e.g., GenBank Accession Nos. AAC51652 (Homo sapiens ALDH1); NP_000680 (Homo sapiens ALDH1); AAH61526 (Rattus norvegicus ALDH1); AAI05194 (Bos taurus ALDH1); and NP_036051 (Mus musculus ALDH1). The term "ALDH1" as used herein also encompasses fragments, fusion proteins, and variants (e.g., variants having one or more amino acid substitutions, addition, deletions, and/or insertions) that retain ALDH1 enzymatic activity. The term "ALDH1" encompasses an aldehyde dehydrogenase that oxidizes aromatic aldehydes, including those of the naphthaldehyde, phenanthrenealdehyde, and coumarinaldehyde series, as well as complex polyaromatic aldehydes. The term "ALDH1" encompasses a cytosolic aldehyde dehydrogenase including but are not limited to ALDH1A1, ALDH1A2, ALDH1A3, ALDH1B1, ALDH1B1, ALDH1L1.

The term "ALDH1" encompasses an enzymatically active polypeptide having at least about 75%, at least about 80%, at least about 85%, at least about 90%, at least about 95%, at least about 98%, at least about 99%, or 100%, amino acid sequence identity to the amino acid sequence set forth in SEQ ID NO:3 or SEQ ID NO:4 (depicted in FIGS. 2A and 2B, respectively).

As used herein, the term "aldehyde dehydrogenase-2" or "ALDH2" refers to an enzyme that oxidizes an aldehyde (e.g., a xenogenic aldehyde, a biogenic aldehyde, or an aldehyde produced from a compound that is ingested, inhaled, or absorbed) to its corresponding acid in an NAD$^-$-dependent reaction. For example, ALDH2 oxidizes aldehydes derived from the breakdown of compounds, e.g., toxic compounds that are ingested, that are absorbed, that are inhaled, or that are produced during normal metabolism. Mitochondrial ALDH2 is naturally found in mitochondria.

The term "ALDH2" encompasses ALDH2 from various species. Amino acid sequences of ALDH2 from various species are publicly available. For example, a human ALDH2 amino acid sequence is found under GenBank Accession Nos. AAH02967 and NP_000681; a mouse ALDH2 amino acid sequence is found under GenBank Accession No. NP_033786; and a rat ALDH2 amino acid sequence is found under GenBank Accession No. NP_115792. The term "ALDH2" encompasses an aldehyde dehydrogenase that exhibits substrate specificity, e.g., that preferentially oxidizes aliphatic aldehydes. The term "ALDH2" encompasses an enzymatically active polypeptide having at least about 75%, at least about 80%, at least about 85%, at least about 90%, at least about 95%, at least about 98%, at least about 99%, or 100%, amino acid sequence identity to amino acids 18-517 of the amino acid sequence set forth in SEQ ID NO:1 (FIG. 1A) or SEQ ID NO:2 (FIG. 1B).

The term "ALDH2" as used herein also encompasses fragments, fusion proteins, and variants (e.g., variants having one or more amino acid substitutions, addition, deletions, and/or insertions) that retain ALDH2 enzymatic activity. Specific enzymatically active ALDH2 variants, fragments, fusion proteins, and the like can be verified by adapting the methods described herein. An example of an ALDH2 variant is an ALDH2 polypeptide that comprises a Glu-to-Lys substitution at amino acid position 487 of human ALDH2, as depicted in FIG. 1B (amino acid 504 of SEQ ID NO:2), or at a position corresponding to amino acid 487 of human ALDH2. This mutation is referred to as the "E487K mutation"; the "E487K variant"; or as the "Glu504Lys polymorphism". See, e.g., Larson et al. (2005) *J. Biol. Chem.* 280:30550; and Li et al. (2006) *J. Clin. Invest.* 116:506. An ALDH2 variant retains at least about 1% of the enzymatic activity of a corresponding wild-type ALDH2 enzyme. For example, the E487K variant retains at least about 1% of the activity of an enzyme comprising the amino acid sequence depicted in FIG. 1A (SEQ ID NO:1). "ALDH2" includes an enzyme that converts acetaldehyde into acetic acid, e.g., where the acetaldehyde is formed in vivo by the action of alcohol dehydrogenase on ingested ethanol.

The term "ALDH3" encompasses ALDH3 from various species. Amino acid sequences of ALDH3 from various species are publicly available. See, e.g., GenBank Accession Nos. AAB26658 (*Homo sapiens* ALDH3), NP_000683 (*Homo sapiens* ALDH3), P30838 (*Homo sapiens* ALDH3), NP-001106196 (*Mus musculus* ALDH3), and AAH70924 (*Rattus norvegicus* ALDH3). The term "ALDH3" as used herein also encompasses fragments, fusion proteins, and variants (e.g., variants having one or more amino acid substitutions, addition, deletions, and/or insertions) that retain ALDH3 enzymatic activity. The term "ALDH3" encompasses an aldehyde dehydrogenase that exhibits specificity toward aromatic aldehydes, e.g., oxidizing aromatic aldehydes of the 2-naphthaldehyde series, but inactive toward 1-naphthaldehydes and higher polyaromatic aldehydes. The term "ALDH3" encompasses an aldehyde dehydrogenase that can use both $NAD^+$ and $NADP^+$ as co-substrate. The term "ALDH3" encompasses aldehyde dehydrogenase found naturally in saliva and in the cornea.

The term "ALDH3" encompasses an enzymatically active polypeptide having at least about 75%, at least about 80%, at least about 85%, at least about 90%, at least about 95%, at least about 98%, at least about 99%, or 100%, amino acid sequence identity to the amino acid sequence encoded by the ALDH3A1 gene.

The term "ALDH4" refers to a mitochondrial matrix dehydrogenase enzyme catalyzing the second step in the proline degradation pathway—the irreversible conversion of 1-pyrroline-5-carboxylate (P5C) derived either from proline or ornithine to glutamate. Mutations in ALDH4A1 can be associated with type II hyperprolinemia, an autosomal recessive disorder characterized by accumulation of P5C and proline resulting in neurological manifestations including seizures and mental retardation.

The term "ALDH5" (also referred to as "succinic semialdehyde dehydrogenase") encompasses an $NAD^+$-dependent enzyme that oxidizes succinic semialdehyde to succinate. ALDH5 is involved in the catabolism of 4-aminobutyric acid (GABA). Naturally-occurring ALDH5 can be found in the mitochondria of eukaryotic cells. The term "ALDH5" encompasses an enzymatically active polypeptide having at least about 75%, at least about 80%, at least about 85%, at least about 90%, at least about 95%, at least about 98%, at least about 99%, or 100%, amino acid sequence identity to the amino acid sequence set forth in GenBank Accession No. AAH34321.

The term "ALDH6" refers to a mitochondrialdehydrogenase enzyme (also known as acetyl CoA-dependent methylmalonate semialdehyde dehydrogenase) that is responsible for catalyzing the irreversible oxidative decarboxylation of malonate and methylmalonate semialdehydes to acetyl- and propionyl-CoA. ALDH6A1 is unique among ALDH\'s because it is CoA-dependent. Like other ALDH\'s ALDH6A1 also retains esterase activity allowing it to hydrolyze p-nitrophenyl acetate with concomitant formation of an S-acyl enzyme and in the presence of CoA will generate acetyl-CoA. A deficiency in ALDH6A1 activity is characterized by elevated levels in urine of beta-alanine, 3-hydroxypropionic acid, and both isomers of 3-amino and 3-hydroxyisobutyric acids.

The term "ALDH7" refers to a cytosol, nucleus, mitochondria aldehyde dehydrogenase that catalyze the detoxification of α-Aminoadipic semi-aldehyde. Mammalian ALDH7A1 can play a major role in the detoxification of aldehydes generated by alcohol metabolism and lipid peroxidation.

The term "ALDH8" refers to a cytosolic dehydrogenase enzyme that can oxidize retinaldehyde to retinoic acid. It plays a role in the 9-cis-retinoic acid biosynthesis pathway in vivo by converting 9-cis-retinal into the retinoid X receptor ligand 9-cis-retinoic acid, ALDH8A1 has approximately a 40-fold higher activity with 9-cis-retinal than with all-trans-retinal. ALDH8A1 is the first known aldehyde dehydrogenase to show a preference for 9-cis-retinal relative to all-trans-retinal. Two transcript variants encoding distinct isoforms have been identified for this gene.

The term "ALDH8" refers to a cytosolic dehydrogenase enzyme catalyzing the dehydrogenation of gamma-aminobutyraldehyde and aminoaldehydes derived from polyamines. ALDH9A1 has also been identified as a betaine aldehyde dehydrogenase. ALDH9A1 is highly expressed in the liver, skeletal muscle, and kidney.

The term "ALDH8" refers to a mitochondiraldehydrogenase enzyme catalyzing the dehydrogenation of Glutamic γ-semi-aldehyde. The ALDH18A1 gene encodes for a bifunctional ATP- and NAD(P)H-dependent mitochondrial inner membrane enzyme (~87.1 kDa subunits) with both gamma-glutamyl kinase and gamma-glutamyl phosphate reductase activities. Also known as Δ1-pyrroline-5-carboxylate synthetase, ALDH18A1 catalyzes the reduction of L-glutamate to Δ1-pyrroline-5-carboxylate, a critical step in the de novo biosynthesis of proline, ornithine and arginine. Individuals with an allelic variant in the ALDH18A1 gene (a G-to-A transition at position 251) exhibit hyperammonemia, hypoornithinemia, hypocitrullinemia, hypoargininemia and hypoprolinemia and associated neurodegeneration, cataracts and connective tissue diseases secondary to the impaired functions of the long and short isoforms of the enzyme.

The term "retinol dehydrogenase" or "RDH" refers to enzymes in the ALDH family that catalyze reduction of aldehydic substrates, including retinaldehydes such as all-trans-retinal and medium-chain aldehydes such as 4-HNE. The term "RDH" encompasses any of the known isozymes, including but are not limited to RDH 11, RDH 12, ALDH1A1, ALDH1A2, ALDH1A3, ALDH2, ALDH8A1, and AKR1b1.

The term "neuropathy" as used herein, refers to any disease or abnormality of the neurons of the nervous system. In particular "neuropathy" means a disorder of the peripheral nervous system, affecting nerves anywhere except brain and the spinal cord. A non-limiting example for neuropathy is alcoholic polyneuropahy which is characterized by numbness, abnormal sensations called dysesthesias and allodynias that occur either spontaneously or in reaction to external stimuli, and a characteristic form of pain, called neuropathic pain or neuralgia.

The term "neurodegenerative disease" as used herein, refers to any disease or abnormality of the of the nervous system caused by deterioration of neurons, which include death of neurons and functional loss of neurotransmitters. Non-limiting examples for a neurodegenerative disease are Alzheimer's disease and Parkinson's disease. The term "food composition" as used herein, refers to any kind of composition which is eatable and/or drinkable without causing toxic symptoms in the subject eating or drinking the respective composition.

The term "late-onset Alzheimer's Disease" as used herein, refers to the onset of Alzheimer's Disease in elderly people, in particular in people being 65 years old and older.

The term "early-onset Alzheimer's Disease" as used herein, refers to the onset of Alzheimer's Disease in people younger than 65 years old.

The term "bis-allylic position," as used herein, refers to the position of the compound, such as polyunsaturated fatty acid or ester thereof, that corresponds to the methylene groups of 1,4-diene systems. Examples of compound having deuterium at one or more bis-allylic positions include but are not limited to 11,11-Dideutero-cis,cis-9,12-Octadecadienoic acid (11,11-Dideutero-(9Z,12Z)-9,12-Octadecadienoic acid; D2-LA); and 11,11,14,14-Tetradeutero-cis,cis,cis-9,12,15-Octadecatrienoic acid (11,11,14,14-Tetradeutero-(9Z,12Z,15Z)-9,12,15-Octadecatrienoic acid; D4-ALA).

The term "pro-bis-allylic position," as used herein, refers to the methylene group that becomes the bis-allylic position upon desaturation. Some sites which are not bis-allylic in the precursor PUFAs will become bis-allylic upon biochemical transformation. The pro-bis-allylic positions, in addition to deuteration, can be further reinforced by carbon-13, each at levels of isotope abundance above the naturally-occurring abundance level. For example, the pro-bis-allylic positions, in addition to existing bis-allylic positions, can be reinforced by isotope substitution as shown below in Formula (2), wherein $R^1$ is alkyl, cation, or H; m=1-10; n=1-5; and p=1-10. In Formula (2), the position of the X atom represents the pro-bis-allylic position, while the position of the Y atom represents the bis-allylic position, each of $X^1$ and $X^2$ (for each m) can be independently a hydrogen or deuterium, and each of $Y^1$ and $Y^2$ (for each n) can be independently a hydrogen or deuterium, and one or more of $X^1$, $X^2$, $Y^1$, or $Y^2$ atoms can be deuterium atoms. In some embodiments, at least one or more of $X^1$, $X^2$, $Y^1$, or $Y^2$ atoms can be deuterium atoms.

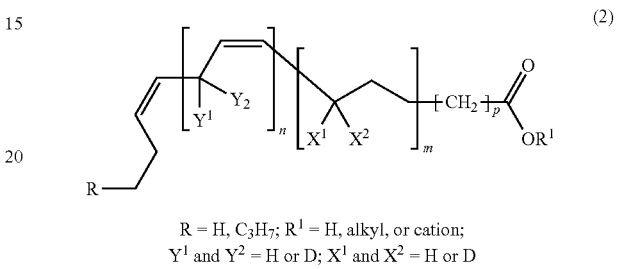

(2)

R = H, C$_3$H$_7$; R$^1$ = H, alkyl, or cation;
Y$^1$ and Y$^2$ = H or D; X$^1$ and X$^2$ = H or D Another example of a compound having bis-allylic and pro-bis-allylic positions is shown in Formula (3), wherein any of the pairs of $Y^1$-$Y^n$ and/or $X^1$-$X^m$ represent the bis-allylic and pro-bis-allylic positions of PUFAs respectively and these positions may contain deuterium atoms. In some embodiments, each $Y^1$-$Y^n$ and/or $X^1$-$X^m$ can independently be hydrogen or deuterium. In some embodiments, at least one $Y^1$-$Y^n$ and/or $X^1$-$X^m$ is a deuterium.

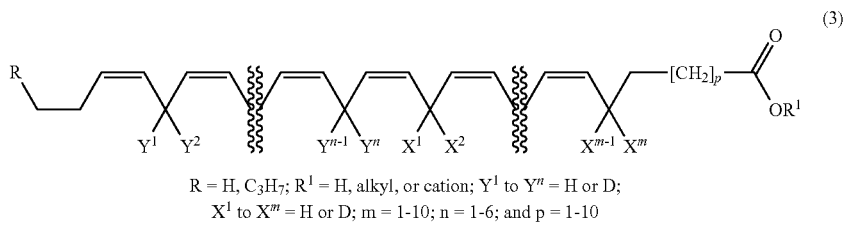

(3)

R = H, C$_3$H$_7$; R$^1$ = H, alkyl, or cation; Y$^1$ to Y$^n$ = H or D;
X$^1$ to X$^m$ = H or D; m = 1-10; n = 1-6; and p = 1-10

As used herein, the term "polyunsaturated fatty acid mimetic" or "PUFA mimetic" refers to a compound having one or more bis-allylic position in the PUFA chemically modified to remove one or more hydrogens at the bis-allylic positions. The PUFA mimetic is less prone to oxidation when compared with the unmodified PUFA.

As used herein, the term "thioester" refers to a structure in which a carboxylic acid and a thiol group are linked by an ester linkage or where a carbonyl carbon forms a covalent bond with a sulfur atom —COSR, wherein R may include hydrogen, $C_{1-30}$ alkyl (branched or straight) and optionally substituted $C_{6-10}$ aryl, heteroaryl, cyclic, or heterocyclic structure. "Polyunsaturated fatty acid thioester" refers to a structure P—COSR, wherein P is a polyunsaturated fatty acid described herein. Examples include but are not limited to thioesters of mercaptoethanol, cysteine, homocysteine, propanethiol, dithioerythritol, thiophenyl, 2-butenethiol, furfurvithiol, 6-mercaptopurine, 2-mercapto-benzothiazole.

As used herein, the term "amide" refers to compounds or moieties that contain a nitrogen atom bound to the carbon of a carbonyl or a thiocarbonyl group such as compounds containing —C(O)NR$^1$R$^2$ or —S(O)NR$^1$R$^2$, and R$^1$ and R$^2$ can independently be C$_{1-30}$ alkyl (branched or straight), optionally substituted C$_{6-10}$ aryl, heteroaryl, cyclic, heterocyclic, or C$_1$-20 hydroalkyl. "Polyunsaturated fatty acid amide" refers to a structure wherein the amide group is attached to the polyunsaturated fatty acid described herein through the carbon of the carbonyl moiety. Examples of polyunsaturated fatty acid amide include but are not limited to amide of ethanolamine, lysine, arginine, diethanolamine, morpholine, glucamine, N,N-dimethylglucamine, N-methylglucamine, and ornithine.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rodents, rats, mice guinea pigs, or the like.

An "effective amount" or a "therapeutically effective amount" as used herein refers to an amount of a therapeutic agent that is effective to relieve, to some extent, or to reduce the likelihood of onset of, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

"Treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

Isotopically or Chemically Modified Compound

The compound described herein comprises an isotopically modified polyunsaturated fatty acid, isotopically modified polyunsaturated fatty acid ester, isotopically modified polyunsaturated fatty acid thioester, isotopically modified polyunsaturated fatty acid amide, polyunsaturated fatty acid mimetic, or isotopically modified polyunsaturated fatty acid pro-drug. In some embodiments, the compound is an isotopically modified polyunsaturated fatty acid. In some embodiments, the compound is an isotopically modified polyunsaturated fatty acid thioester. In some embodiments, the compound is an isotopically modified polyunsaturated fatty acid amide. In some embodiments, the compound is a polyunsaturated fatty acid mimetic. In some embodiments, the compound is an isotopically modified polyunsaturated fatty acid pro-drug.

In some embodiments, the polyunsaturated fatty acid, polyunsaturated fatty acid ester, polyunsaturated fatty acid thioester, polyunsaturated fatty acid amide, polyunsaturated fatty acid mimetic, or polyunsaturated fatty acid pro-drug can be a naturally occurring PUFA. In some embodiments, the polyunsaturated fatty acid, polyunsaturated fatty acid ester, polyunsaturated fatty acid thioester, polyunsaturated fatty acid amide, polyunsaturated fatty acid mimetic, or polyunsaturated fatty acid pro-drug can have conjugated double bonds.

In some embodiments, the compound is deuterated at one or more positions. In some embodiments, the compound is deuterated at one or more bis-allylic positions. In some embodiments, the polyunsaturated fatty acid, polyunsaturated fatty acid ester, polyunsaturated fatty acid thioester, polyunsaturated fatty acid amide, polyunsaturated fatty acid mimetic, or polyunsaturated fatty acid pro-drug is deuterated at one or more positions. In some embodiments, the polyunsaturated fatty acid, polyunsaturated fatty acid ester, polyunsaturated fatty acid thioester, polyunsaturated fatty acid amide, polyunsaturated fatty acid mimetic, or polyunsaturated fatty acid pro-drug is deuterated at one or more bis-allylic positions.

In some embodiments, wherein the polyunsaturated fatty acid ester is triglyceride, diglyceride, or monoglyceride.

In some embodiments, the polyunsaturated fatty acid ester is an ethyl ester.

In some embodiments, the compound is a ω-3 or ω-6 fatty acid, ω-3 or ω-6 fatty acid ester, ω-3 or ω-6 fatty acid amide, ω-3 or ω-6 fatty acid thioester, or prodrug thereof. In some embodiments, the compound is a linoleic acid, linolenic acid, arachidonic acid, eicosapentaenoic acid, docosahexaenoic acid, or their ester, amide, thioester, and prodrug thereof.

In some embodiments, the compound is administered to a patient with non-modified polyunsaturated fatty acids or polyunsaturated fatty acid ester. In some embodiments, the compound is administered to a patient with non-modified polyunsaturated fatty acid, polyunsaturated fatty acid ester, polyunsaturated fatty acid thioester, polyunsaturated fatty acid amide, polyunsaturated fatty acid mimetic, or polyunsaturated fatty acid pro-drug.

In some embodiments, the compound comprises a therapeutically active dose in the range of about 0.01%-400%, 0.01%-95%, 0.05%-90%, 0.05%-80%, 0.05%-75%, 0.05%-70%, 0.05%-60%, 0.05%-50%, 0.05%-40%, 0.05%-30%, 0.05%-20%, 0.05%-10%, 0.5%-90%, 0.5%-80%, 0.5%-75%, 0.5%-70%, 0.5%-60%, 0.5%-50%, 0.5%-40%, 0.5%-30%, 0.5%-20%, 0.5%-10%, 1%-90%, 1%-80%, 1%-75%, 1%-70%, 1%-60%, 1%-50%, 1%-40%, 1%-30%, 1%-20%, 1%-10%, 2.5%-90%, 2.5%-80%, 2.5%-75%, 2.5%-70%, 2.5%-60%, 75%-50%, 7.5%-40%, 2.5%-30%, 2.5%-20%, 2.5%-10%, 4%-90%, 4%-80%, 4%-75%, 4%-70%, 4%-60%, 4%-50%, 4%-40%, 4%-30%, 4%-20%, 4%-10%, 5%-90%, 5%-80%, 5%-75%, 5%-70%, 5%-60%, 5%-50%, 5%-40%, 5%-30%, 5%-20%, 5%-10%, 7.5%-90%, 7.5%-80%, 7.5%-75%, 7.5%-70%, 7.5%-60%, 7.5%-50%, 7.5%-40%, 7.5%-30%, 7.5%-20%, 7.5%-10%, 9%-90%, 9%-80%, 9%-75%, 9%-70%, 9%-60%, 9%-50%, 9%-40%, 9%-30%, 9%-20%, 9%-10%, 10%-90%, 10%-80%, 10%-75%, 10%-70%, 10%-60%, 10%-50%, 10%-40%, 10%-30%, 10%-20%, about 0.1%-100%, or about 1%-100% of the total amount of polyunsaturated fatty acid, polyunsaturated fatty acid ester, polyunsaturated fatty acid thioester, polyunsaturated fatty acid amide, polyunsaturated fatty acid mimetic, and polyunsaturated fatty acid pro-drug administered to the patient. In some embodiments, the compound comprises at least about 0.01%, 0.05%, 0.1%, 0.5%, 1%, 2%, 3%, 4%, 5%, 6%, 7%, 8%, 9%, 10%, 17.5%, 1517.5%, 70%, 75%, 30%, 35%, 40%, 45%, 50%, 55%, 60%, 65%, 70%, 75%, 80%, 85%, 90%, or 95%, of the total amount of polyunsaturated fatty acid, polyunsaturated fatty acid ester, polyunsaturated fatty acid thioester, polyunsaturated fatty acid amide, polyunsaturated fatty acid mimetic, and polyunsaturated fatty acid pro-drug administered to the patient. In some embodiments, the compound comprises less than about 10%, 12.5%, 1517.5%, 20%, 30%, 35%, 40%, 45%, 50%, 55%, 60%, 65%, 70%, 75%, 80%, 85%, 90%, 95%, 99%, or 100% of the total amount of polyunsaturated fatty acid, polyunsaturated fatty acid ester, polyunsaturated fatty acid thioester, polyunsaturated fatty acid amide, polyunsaturated fatty acid mimetic, and polyunsaturated fatty acid pro-drug administered to the patient. In some embodiments, the compound comprises between 0.01% and 90%, about 0.1% and 90%, or about 5% and 90% of the total amount of polyunsaturated fatty acid, polyunsaturated fatty acid ester, polyunsaturated fatty acid thioester, polyunsaturated fatty acid amide, polyunsaturated fatty acid mimetic, and polyunsaturated fatty acid pro-drug administered to the patient. In some embodiments, the compound comprises between about 20% and 80% of the total amount of polyunsaturated fatty acid, polyunsaturated fatty acid ester, polyunsaturated fatty acid thioester, polyunsaturated fatty acid amide, polyunsaturated fatty acid mimetic, and polyunsaturated fatty acid pro-drug administered to the patient. In some embodiments, the compound comprises between about 10% and 40% of the total amount of polyunsaturated fatty acid, polyunsaturated fatty acid ester, polyunsaturated fatty acid thioester, polyunsaturated fatty acid amide, polyunsaturated fatty acid mimetic, and polyunsaturated fatty acid pro-drug administered to the patient. In some embodiments, the compound comprises about 20% or more of the total amount of polyunsaturated fatty acid, polyunsaturated fatty acid ester, polyunsaturated fatty acid thioester, polyunsaturated fatty acid amide, polyunsaturated fatty acid mimetic, and polyunsaturated fatty acid pro-drug administered to the patient.

In some embodiments the compound represents a therapeutically active dose given as an initial loading dose and a subsequent lower maintenance dose, each sufficient to elicit therapeutically beneficial effects in a subject requiring treatment. In some embodiments, the initial loading dose can be in the range of about 0.1 mg to about 20 mg, about 0.5 mg to about 15 mg, or about 1 mg to about 12 mg. In some embodiments, the maintenance dose can be in the range of about 0.1 mg to about 20 mg, about 0.5 mg to about 15 mg, or about 1 mg to about 12 mg. In some embodiments, the initial loading dose is greater than the maintenance dose. In some embodiments, the initial loading dose is less than the maintenance dose.

In some embodiments, a cell or tissue of the subject maintains a sufficient concentration of the compound to prevent or reduce autoxidation of the naturally occurring non-modified polyunsaturated fatty acid or polyunsaturated fatty acid ester.

In some embodiments, the compound comprises an amount of deuterium that is significantly above the naturally-occurring abundance level of the deuterium. In some embodiments, the compound comprises an amount of $^{13}C$ that is significantly above the naturally-occurring abundance level of the $^{13}C$ in the molecule.

In some embodiments, the compound is selected from the group consisting of 11, 11, D2-linolenic acid, 14, 14, D2-linolenic acid, 11, 11, 14, 14. D4-linolenic acid, 11, 11, D2-linoleic acid, 14, 14, D2-linoleic acid, and 11, 11, 14, 14, D4-linoleic acid.

In some embodiments, the compound is an omega-3 fatty acid. In some embodiments, the omega-3 fatty acid is alpha linolenic acid.

In some embodiments, the compound is an omega-6 fatty acid. In some embodiments, the omega-6 fatty acid is linoleic acid. In some embodiments, the omega-6 fatty acid is gamma linolenic acid, dihomo gamma linolenic acid, arachidonic acid, or docosatetraenoic acid.

In some embodiments, the compound is administered with an antioxidant.

In some embodiments, the compound is administered to a patient with non-modified fatty acids or fatty acid esters.

In some embodiments, a cell or tissue of the patient maintains a sufficient concentration of the deuterated fatty acid or fatty acid ester to prevent or reduce autoxidation of the naturally occurring non-deuterated fatty acid or fatty acid ester.

The compound isotopically reinforced at oxidation sensitive positions as described by way of the structures above are heavy isotope enriched at the positions as compared to the natural abundance of the appropriate isotope. In some embodiments, the compound has the deuterium atom present at a level greater than its natural abundance level. In some embodiments, deuterium has a natural abundance of roughly 0.0156% of all naturally occurring hydrogen in the oceans on earth. Thus, a compound having greater that the natural abundance of deuterium may have greater than this level or greater than the natural abundance level of roughly 0.0156% of its hydrogen atoms reinforced with deuterium, such as 0.02%, but preferably about 5%, 10%, 15%, 20%, 25%, 30%, 35%, 40%, 45%, 50%, 65%, 60%, 65%, 70%, 75%, 80%, 85%, 90%, 95%, or 100% of deuterium with respect to one or more hydrogen atoms in each compound molecule. In other embodiments, the percentage of total hydrogen atoms reinforced with deuterium is at least 0.02%, 0.05%, 0.1%, 1%, 2%, 5%, 10%, 15%, 20%, 25%, 30%, 35%, 40%, 45%, 50%, 65%, 60%, 65%, 70%, 75%, 80%, 85%, 90%, 95%, or 100%. In other embodiments, the percentage of total hydrogen atoms reinforced with deuterium is less than 2%, 5%, 10%, 15%, 20%, 25%, 30%, 35%, 40%, 45%, 50%, 65%, 60%, 65%, 70%, 75%, 80%, 85%, 90%, 95%, or 100%.

In some aspects, a composition contains both isotopically modified compound and isotopically unmodified compound. The isotopic purity is a comparison between a) the relative number of molecules of isotopically modified compound, and b) the total molecules of both isotopically modified compound and compound with no heavy atoms. In some embodiments, the isotopic purity refers to compound that are otherwise the same except for the heavy atoms.

In some embodiments, isotopic purity refers to the percentage of molecules of an isotopically modified compound in the composition relative to the total number of molecules of the isotopically modified compound plus compound with no heavy atoms. For example, the isotopic purity may be about 5%, 10%, 15%, 20%, 25%, 30%, 35%, 40%, 45%, 50%, 65%, 60%, 65%, 70%, 75%, 80%, 85%, 90%, 95%, or 100% of the molecules of isotopically modified compound relative to the total number of molecules of both the isotopically modified compound plus compound with no heavy atoms. In other embodiments, the isotopic purity is at least 5%, 10%, 15%, 20%, 25%, 30%, 35%, 40%, 45%, 50%, 65%, 60%, 65%, 70%, 75%, 80%, 85%, 90%, 95%, or 100%. In some embodiments, isotopic purity of the compound may be from about 10%-100%, 10%-95%, 10%-90%, 10%-85%, 10%-80%, 10%-75%, 0%-70%, 10%-65%, 10%-60%, 10%-55%, 10%-50%, 10%-45%, 10%-40%, 10%-35%, 10%-30%, 10%-25%, or 10%-20% of the total number of molecules of the compound in the composition. In other embodiments, isotopic purity of the compound may be from about 15%-100%, 15%-95%, 15%-90%, 15%-85%, 15%-80%, 15%-75%, 15%-70%, 15%-65%, 15%-60%, 15%-55%, 15%-50%, 15%-45%, 15%-40%, 15%-35%, 15%-30%, 15%-25%, or 15%-20% of the total number of molecules of the compound in the composition. In some embodiments, isotopic purity of the compound may be from about 20%-100%, 20%-95%, 20%-90%, 20%-85%, 20%-80%, 20%-75%, 20%-70%, 20%-65%, 20%-60%, 20%-55%, 20%-50%, 20%-45%, 20%-40%, 20%-35%, 20%-30%, or 20%-25% of the total number of molecules of the compound in the composition. Two molecules of an isotopically modified compound out of a total of 100 total molecules of isotopically modified compound plus compound with no heavy atoms will have 2% isotopic purity, regardless of the number of heavy atoms the two isotopically modified molecules contain.

In some aspects, an isotopically modified PUFA molecule may contain one deuterium atom, such as when one of the two hydrogens in a methylene group is replaced by deuterium, and thus may be referred to as a "D1" PUFA. Similarly, an isotopically modified PUFA molecule may contain two deuterium atoms, such as when the two hydrogens in a methylene group are both replaced by deuterium, and thus may be referred to as a "D2" PUFA. Similarly, an isotopically modified PUFA molecule may contain three deuterium atoms and may be referred to as a "D3" PUFA. Similarly, an isotopically modified PUFA molecule may contain four deuterium atoms and may be referred to as a "D4" PUFA. In some embodiments, an isotopically modified PUFA molecule may contain five deuterium atoms or six deuterium atoms and may be referred to as a "D5" or "D6" PUFA, respectively.

The number of heavy atoms in a molecule, or the isotopic load, may vary. For example, a molecule with a relatively low isotopic load may contain about 1, 2, 3, 4, 5, or 6 deuterium atoms. A molecule with a moderate isotopic load may contain about 10, 11, 12, 13, 14, 15, 16, 17, 18, 19, or 20 deuterium atoms. In a molecule with a very high load, every hydrogen may be replaced with a deuterium. Thus, the isotopic load refers to the percentage of heavy atoms in each compound molecule. For example, the isotopic load may be about 5%, 10%, 15%, 20%, 25%, 30%, 35%, 40%, 45%, 50%, 65%, 60%, 65%, 70%, 75%, 80%, 85%, 90%, 95%, or 100% of the number of the same type of atoms in comparison to a compound with no heavy atoms of the same type (e.g. hydrogen would be the "same type" as deuterium). In some embodiments, the isotopic load is at least 5%, 10%, 15%, 20%, 25%, 30%, 35%, 40%, 45%, 50%, 65%, 60%, 65%, 70%, 75%, 80%, 85%, 90%, 95%, or 100%. Unintended side effects are expected to be reduced where there is high isotopic purity in a compound composition but low isotopic load in a given molecule. For example, the metabolic pathways will likely be less affected by using a composition with high isotopic purity but low isotopic load.

One will readily appreciate that when one of the two hydrogens of a methylene group is replaced with a deuterium atom, the resultant compound may possess a stereocenter. In some embodiments, it may be desirable to use racemic compounds. In other embodiments, it may be desirable to use enantiomerically pure compounds. In additional embodiments, it may be desirable to use diastereomnerically pure compounds. In some embodiments, it may be desirable to use mixtures of compounds having enantiomeric excesses and/or diastereomeric excesses of about 5%, 10%, 15%, 20%, 25%, 30%, 35%, 40%, 45%, 50%, 65%, 60%, 65%, 70%, 75%, 80%, 85%, 90%, 95%, or 100%. In other embodiments, the enantiomneric excesses and/or diastereomeric excesses is at least 5%, 10%, 15%, 20%, 25%, 30%, 35%, 40%, 45%, 50%, 65%, 60%, 65%, 70%, 75%, 80%, 85%, 90%, 95%, or 100%. In some embodiments, it may be preferable to utilize stereochemically pure enantiomers and/or diastereomers of embodiments—such as when contact with chiral molecules is being targeted for attenuating oxidative damage. However, in many circumstances, non-chiral molecules are being targeted for attenuating oxidative damage. In such circumstances, embodiments may be utilized without concern for their stereochemical purity. Moreover, in some embodiments, mixtures of enantiomers and diastereomers may be used even when the compounds are targeting chiral molecules for attenuating oxidative damage.

In some aspects, isotopically modified compound impart an amount of heavy atoms in a particular tissue. Thus, in some aspects, the amount of heavy molecules will be a particular percentage of the same type of molecules in a tissue. For example, the number of heavy molecules may be about 1%-100% of the total amount of the same type of molecules. In some aspects, 10-50% the molecules are substituted with the same type of heavy molecules.

In some embodiments, the compound is deuterated at one or more bis-allylic positions. One example of compound such as an essential PUFAs isotopically modified at bis-allylic positions is shown below in Formula (I), whereas $R^1$=alkyl, H, or cation; m=1-10; n=1-5. The bis-allylic positions, in addition to deuteration, can be further reinforced by carbon-13, each at levels of isotope abundance above the naturally-occurring abundance level. At each bis-allylic position in Formula (I), one or both $Y^1$, $Y^2$ atoms are deuterium atoms. Each of the $Y^1$ and $Y^2$ in each —[$CY^1Y^2$—$CH_2$=$CH_2$]— unit can be independently H or D. In some embodiments, at least one $Y^1$ and $Y^2$ (among all —[$CY^1Y^2$—$CH_2$=$CH_2$]n-units) is a deuterium. For example, when n is 2, each $Y^1$ and $Y^2$ in each of the two —[$CY^1Y^2$—$CH_2$=$CH_2$]— units can be independently H or D; when n is 3, each $Y^1$ and $Y^2$ in each of the three [$CY^1Y^2$—$CH_2$=$CH_2$] units can be independently H or D; when n is 4, each $Y^1$ and $Y^2$ in each of the four —[$CY^1Y^2$—$CH_2$=$CH_2$]— units can be independently H or D; and when n is 5, each $Y^1$ and $Y^2$ in each of the five —[$CY^1Y^2$—$CH_2$=$CH_2$]— units can be independently H or D.

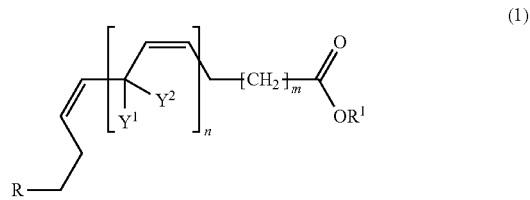

(1)

R = H, $C_3H_7$, $R^1$ = H, alkyl or cation; each $Y^1$ and $Y^2$ can be indepednently H or D Exact structures of compounds illustrated above are shown below that provide for both isotope reinforced n-3 (omega-3) and n-6 (omega-6) essential polyunsaturated fatty acids, and the PUFAs made from them biochemically by desaturation/elongation. Any one of these compounds may be used to slow oxidation. In the following compounds, the PUFAs are isotopically reinforced at oxidation sensitive sites and/or sites that may become oxidation sensitive upon biochemical desaturation/elongation. $R^1$ may be H, alkyl, or cation; $R^2$ may be H or D; * represents either $^{12}C$ or $^{13}C$.

D-Linoleic acids include:

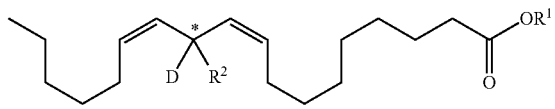

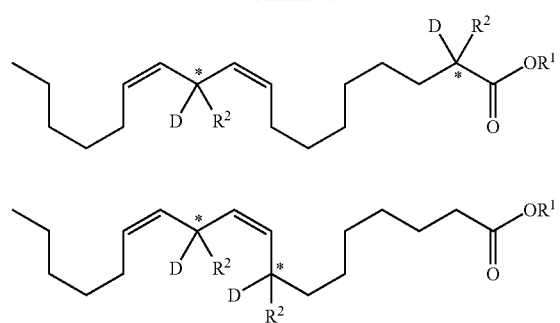
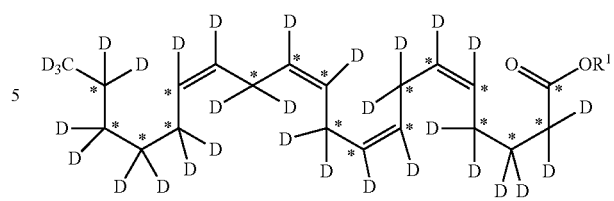
D-Linolenic acids include:
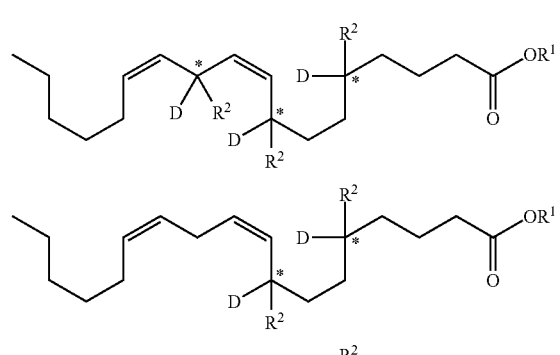
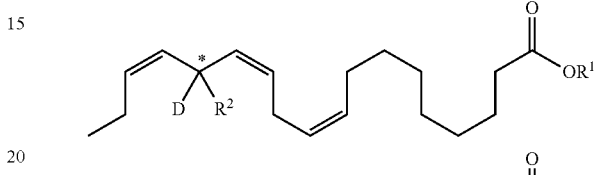
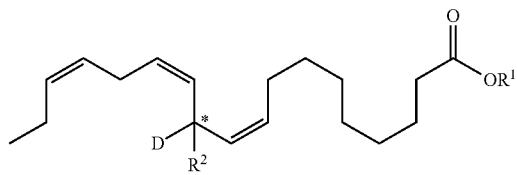
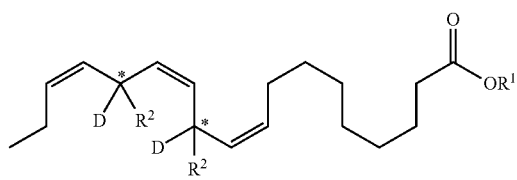
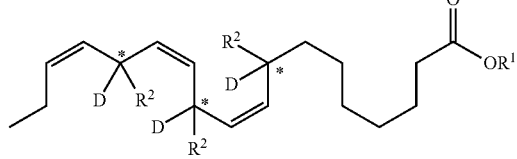
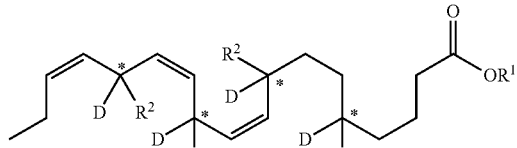
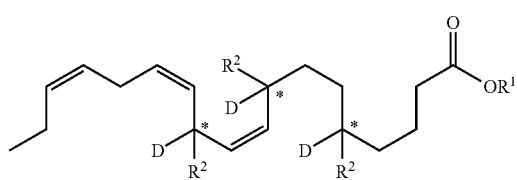
The per-deuterated linoleic acid below may be produced by microbiological methods, for example by growing in media containing deuterium and/or carbon-13.
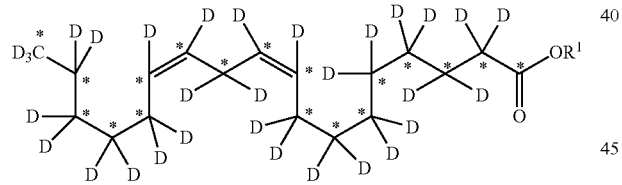
D-Arachidonic acids include:
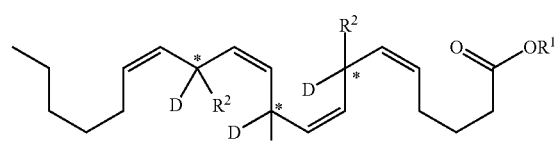
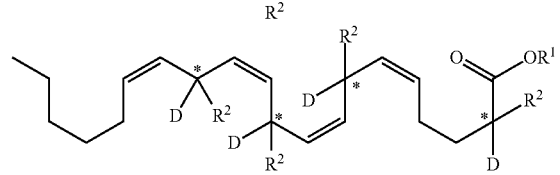
The per-deuterated arachidonic acid below may be produced by microbiological methods, such as by growing in media containing deuterium and/or carbon-13.
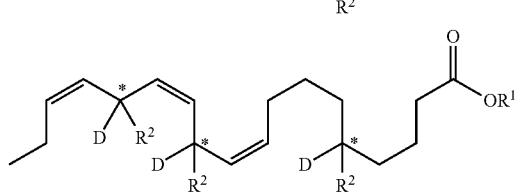

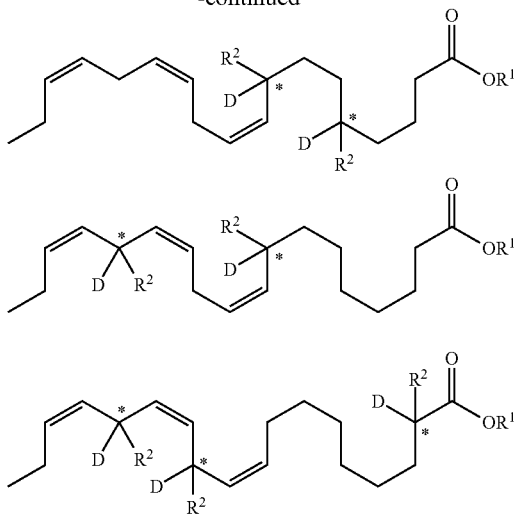

Some examples of some isotopically modified polyunsaturated fatty acid and ester thereof can include the following compounds.

moving bis-allylic hydrogen-activating double bonds further apart, thus eliminating the bis-allylic positions while retaining certain PUFA fluidity as shown below. These PUFA mimetics have no bis-allylic positions.

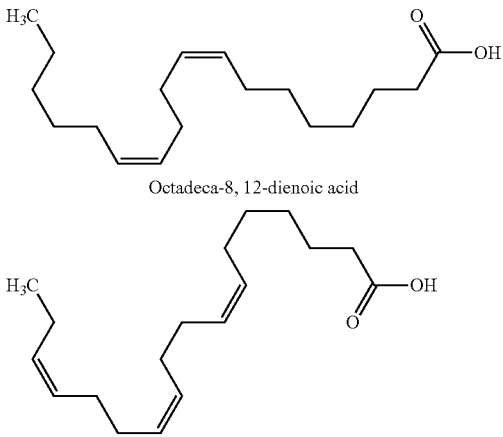

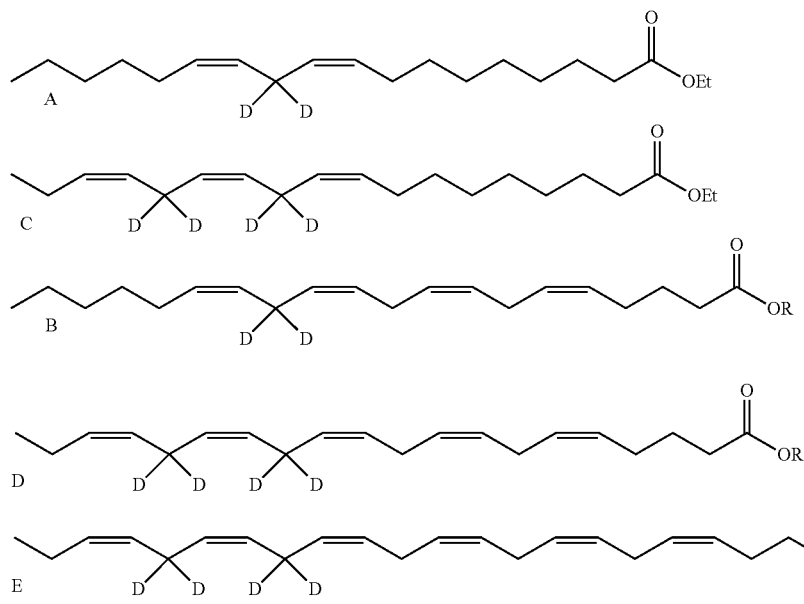

Per-deuterated linolenic acid below may be produced by microbiological methods, such as growing in media containing deuterium and/or carbon-13.

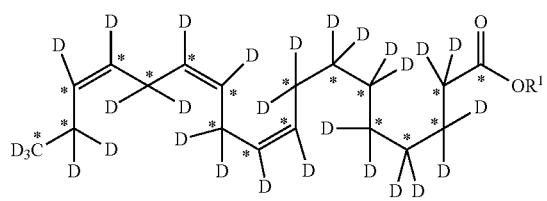

In a further embodiment, oxidation-prone bis-allylic sites of PUFAs can be protected against hydrogen abstraction by using heteroatoms with valence thus eliminating the bis-allylic hydrogens as shown below. These PUFA mimetics also have no bis-allylic hydrogens.

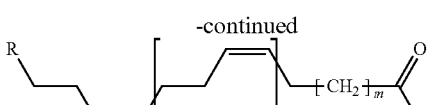

R = H, C$_3$H$_7$; R$^1$ = H; alkyl; n = 1-4; m = 1-12

In a further embodiment, oxidation-prone bis-allylic sites of PUFAs can be protected against hydrogen abstraction by using heteroatoms with valence thus eliminating the bis-allylic hydrogens as shown below. These PUFA mimetics also have no bis-allylic hydrogens.

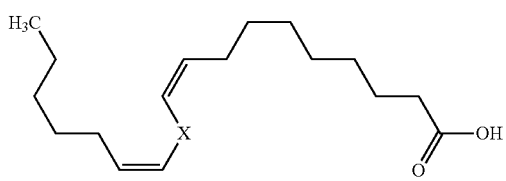

X = S: 10-Hept-1-enylsulfanyl-dec-9-enoic acid
X = O: 10-Hept-1-enyloxy-dec-9-enoic acid

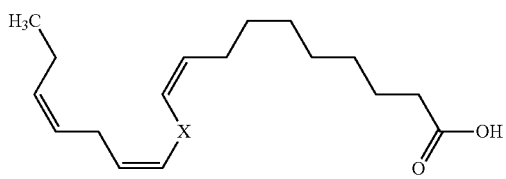

X = S: 10-(2-But-1-enylsulfanyl-vinylsulfanyl)-dec-9-enoic acid
X = O: 10-(2-But-1-enyloxy-vinyloxy)-dec-9-enoic acid

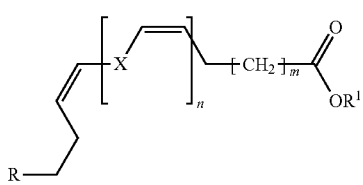

R = H, $C_3H_7$; $R^1$ = H; alkyl; X = O; S; n = 1-5; m = 1-12

In a further embodiment, PUFA mimetics, i.e. compounds structurally similar to natural PUFAs but unable to get oxidized because of the structural differences, can be employed for the above mentioned purposes. Oxidation-prone bis-allylic sites of PUFAs can be protected against hydrogen abstraction by di-methylation or halogenation as shown below. The hydrogen atoms on the methyl groups may optionally be halogens, such as fluorine, or deuterium. These PUFA mimetics are dimethylated at bis-allylic sites.

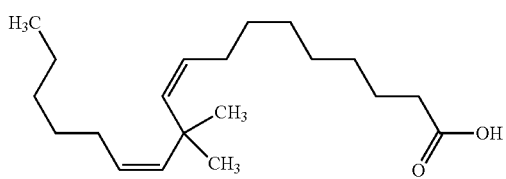

11,11-Dimethyl-octadeca-9,12-dienoic acid

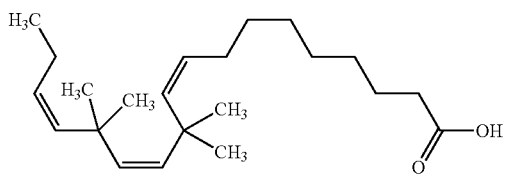

11,11,14,14-Tetramethyl-octadeca-9,12,15-trienoic acid

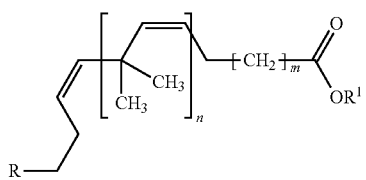

R = H, $C_3H_7$; $R^1$ = H; alkyl; n = 1-5; m = 1-12

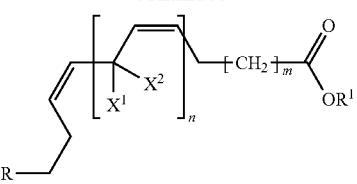

R = H, $C_3H_7$; $R^1$ = H; alkyl; n = 1-5; m = 1-12; $X^1$, $X^2$ = F, Cl., Br, or I In a further embodiment, oxidation-prone bis-allylic sites of PUFAs can be protected against hydrogen abstraction by alkylation as shown below. These PUFA mimetics are dialkylated at bis-allylic sites.

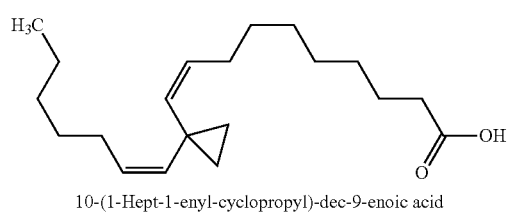

10-(1-Hept-1-enyl-cyclopropyl)-dec-9-enoic acid

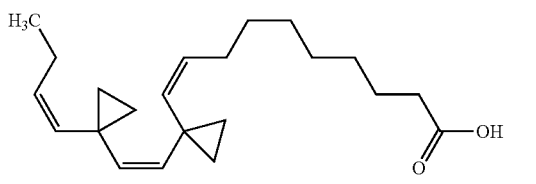

10-(1-[2-(1-But-1-enyl-cyclopropyl)-vinyl]-cyclopropyl)-dec-9-enoic acid

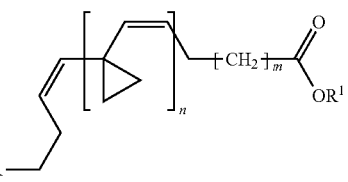

R = H, $C_3H_7$; $R^1$ = H; alkyl; n = 1-5; m = 1-12

In a further embodiment, cyclopropyl groups can be used instead of double bonds, thus rendering the acids certain fluidity while eliminating the bis-allylic sites as shown below. These PUFA mimetics have cyclopropyl groups instead of double bonds.

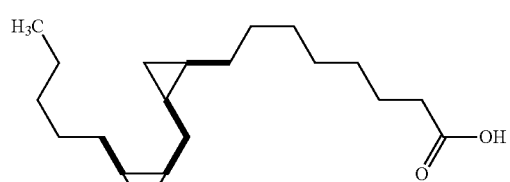

8-[2-(2-Pentyl-cyclopropylmethyl)-cyclopropyl]-octanoic acid

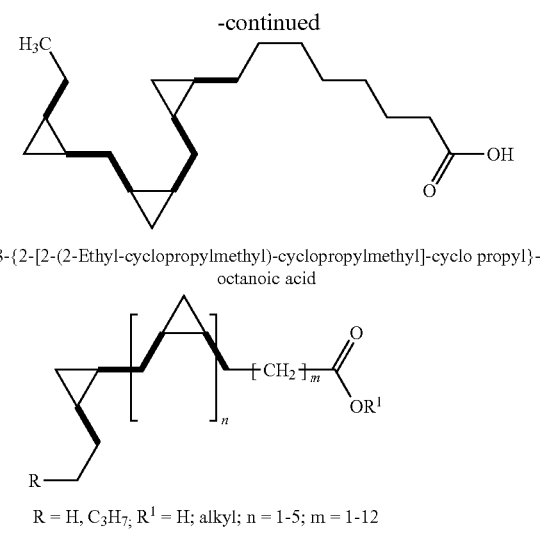

8-{2-[2-(2-Ethyl-cyclopropylmethyl)-cyclopropylmethyl]-cyclo propyl}-octanoic acid R = H, C₃H₇; R¹ = H; alkyl; n = 1-5; m = 1-12

In a further embodiment, 1,2-substituted cyclobutyl groups in appropriate conformation can be used instead of double bonds, thus rendering the acids certain fluidity while eliminating the bis-allylic sites as shown below. These PUFA mimetics have 1,2-cyclobutyl groups instead of double bonds.

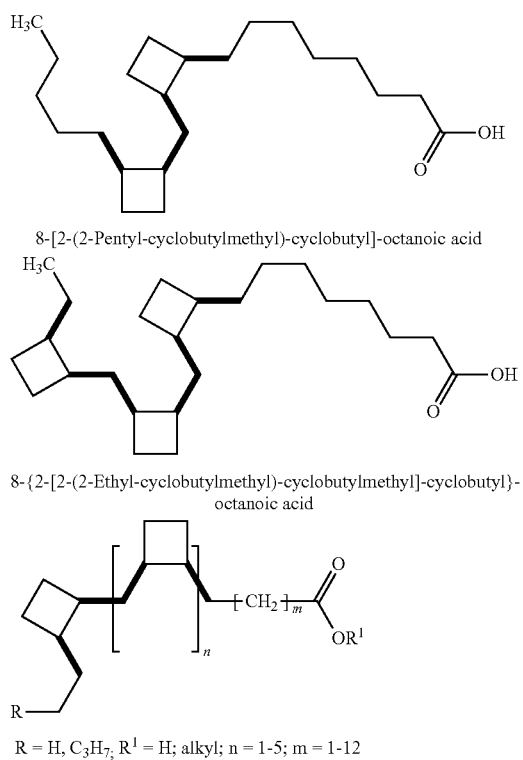

8-[2-(2-Pentyl-cyclobutylmethyl)-cyclobutyl]-octanoic acid

8-{2-[2-(2-Ethyl-cyclobutylmethyl)-cyclobutylmethyl]-cyclobutyl}-octanoic acid

R = H, C₃H₇; R¹ = H; alkyl; n = 1-5; m = 1-12

In a modification of the previous embodiment of mimetics with 1,2-cyclobutyl groups instead of double bonds, 1,3-substituted cyclobutyl groups in appropriate conformation can be used instead of double bonds, thus rendering the acids certain fluidity while eliminating the bis-allylic sites. The following PUFA mimetics have 1,3-cyclobutyl groups instead of double bonds.

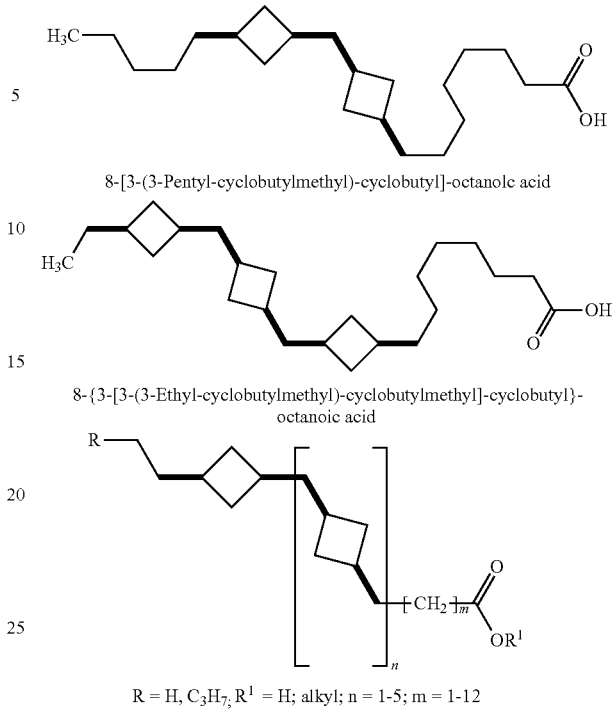

8-[3-(3-Pentyl-cyclobutylmethyl)-cyclobutyl]-octanoic acid

8-{3-[3-(3-Ethyl-cyclobutylmethyl)-cyclobutylmethyl]-cyclobutyl}-octanoic acid

R = H, C₃H₇; R¹ = H; alkyl; n = 1-5; m = 1-12

It is a well-known principle in medicinal chemistry that certain functional groups are isosteric and/or bioisosteric with certain other functional groups. Bioisosteres are substituents or groups with similar physical or chemical properties which produce broadly similar biological properties to a chemical compound. For example, well known isosteres and/or bioisosteres for hydrogen include halogens such as fluorine; isosteres and/or bioisosteres of alkenes include alkynes, phenyl rings, cyclopropyl rings, cyclobutyl rings, cyclopentyl rings, cyclohexyl rings, thioethers, and the like; isosteres and/or bioisosteres of carbonyls include sulfoxides, sulfones, thiocarbonyls, and the like; isosteres and/or bioisosteres of esters include amides, sulfonic acid esters, sulfonamides, sulfinyl acid esters, sulfinylamindes, and the like. Consequently, PUFA mimetics also include compounds having isosteric and/or bioisosteric functional groups.

It is contemplated that it may be useful to formulate PUFAs and/or PUFA mimetics as a pro-drug for use in certain embodiments. A pro-drug is a pharmacological substance may itself have biological activity, but upon administration the pro-drug is metabolized into a form that also exerts biological activity. Many different types of pro-drugs are known and they can be classified into two major types based upon their cellular sites of metabolism. Type I pro-drugs are those that are metabolized intracellularly, while Type II are those that are metabolized extracellularly. It is well-known that carboxylic acids may be converted to esters and various other functional groups to enhance pharmacokinetics such as absorption, distribution, metabolism, and excretion. Esters are a well-known pro-drug form of carboxylic acids formed by the condensation of an alcohol (or its chemical equivalent) with a carboxylic acid (or its chemical equivalent). In some embodiments, alcohols (or their chemical equivalent) for incorporation into pro-drugs of PUFAs include pharmaceutically acceptable alcohols or chemicals that upon metabolism yield pharmaceutically acceptable alcohols. Such alcohols include, but are not limited to, propylene glycol, ethanol, isopropanol, 2-(2-ethoxyethoxy)ethanol (Transcutol®, Gattefosse, Westwood, N.J. 07675), benzyl alcohol, glycerol, polyethylene glycol 200, polyethylene glycol 300, or polyethylene glycol 400; polyoxyethylene castor oil derivatives (for example, polyoxyethyleneglyceroltriricinoleate or polyoxyl 35 castor oil (Cremophor®EL, BASF Corp.), polyoxyethyleneglycerol oxystearate (Cremophor®RH 40 (polyethyleneglycol 40 hydrogenated castor oil) or Cremophor®RH 60 (polyethyleneglycol 60 hydrogenated castor oil), BASF Corp.)); saturated polyglycolized glycerides (for example, Gelucire® 35/10, Gelucire® 44/14, Gelucire® 46/07, Gelucire® 50/13 or Gelucire® 53/10, available from Gattefosse, Westwood, N.J. 07675); polyoxyethylene alkyl ethers (for example, cetomacrogol 1000); polyoxyethylene stearates (for example, PEG-6 stearate, PEG-8 stearate, polyoxyl 40 stearate NF, polyoxyethyl 50 stearate NF, PEG-12 stearate, PEG-20 stearate, PEG-100 stearate, PEG-12 distearate, PEG-32 distearate, or PEG-150 distearate); ethyl oleate, isopropyl palmitate, isopropyl myristate; dimethyl isosorbide; N-methylpyrrolidinone; paraffin; cholesterol; lecithin; suppository bases; pharmaceutically acceptable waxes (for example, carnauba wax, yellow wax, white wax, microcrystalline wax, or emulsifying wax); pharmaceutically acceptable silicon fluids; soribitan fatty acid esters (including sorbitan laurate, sorbitan oleate, sorbitan palmitate, or sorbitan stearate); pharmaceutically acceptable saturated fats or pharmaceutically acceptable saturated oils (for example, hydrogenated castor oil (glyceryl-tris-12-hydroxystearate), cetyl esters wax (a mixture of primarily C14-C18 saturated esters of C14-C18 saturated fatty acids having a melting range of about 43°-47° C.), or glyceryl monostearate).

In some embodiments, the fatty acid pro-drug is represented by the ester P—B, wherein the radical P is a PUFA and the radical B is a biologically acceptable molecule. Thus, cleavage of the ester P—B affords a PUFA and a biologically acceptable molecule. Such cleavage may be induced by acids, bases, oxidizing agents, and/or reducing agents. Examples of biologically acceptable molecules include, but are not limited to, nutritional materials, peptides, amino acids, proteins, carbohydrates (including monosaccharides, disaccharides, polysaccharides, glycosaminoglycans, and oligosaccharides), nucleotides, nucleosides, lipids (including mono-, di- and tri-substituted glycerols, glycerophospholipids, sphingolipids, and steroids).

In some embodiments, alcohols (or their chemical equivalent) for incorporation into pro-drugs of PUFAs include polyalcohols such as dials, triols, tetra-ols, penta-ols, etc. Examples of polyalcohols include ethylene glycol, propylene glycol, 1,3-butylene glycol, polyethylene glycol, methylpropanediol, ethoxydiglycol, hexylene glycol, dipropylene glycol glycerol, and carbohydrates. Esters formed from polyalcohols and PUFAs may be mono-esters, di-esters, tri-esters, etc. In some embodiments, multiply esterified polyalcohols are esterified with the same PUFAs. In other embodiments, multiply esterified polyalcohols are esterified with different PUFAs. In some embodiments, the different PUFAs are stabilized in the same manner. In other embodiments, the different PUFAs are stabilized in different manners (such as deuterium substitution in one PUFA and $^{13}C$ substitution in another PUFA). In some embodiments, one or more PUFAs is an omega-3 fatty acid and one or more PUFAs is an omega-6 fatty acid.

It is also contemplated that it may be useful to formulate PUFAs and/or PUFA mimetics and/or PUFA pro-drugs as salts for use in certain embodiments. For example, the use of salt formation as a means of tailoring the properties of pharmaceutical compounds is well known. See Stahl et al., Handbook of pharmaceutical salts: Properties, selection and use (2002) Weinheim/Zurich: Wiley-VCH/VHCA; Gould, Salt selection for basic drugs, Int. J. Pharm. (1986), 33:201-217. Salt formation can be used to increase or decrease solubility, to improve stability or toxicity, and to reduce hygroscopicity of a drug product.

Formulation of PUFAs and/or PUFA esters and/or PUFA mimetics and/or PUFA pro-drugs as salts can include any PUFA salt described herein.

It may be unnecessary to substitute all isotopically unmodified PUFAs, such as non-deuterated PUFAs, with isotopically modified PUFAs such as deuterated PUFAs. In some embodiments, is preferable to have sufficient isotopically modified PUFAs such as D-PUFAs in the membrane to prevent unmodified PUFAs such as H-PUFAs from sustaining a chain reaction of self-oxidation. During self-oxidation, when one PUFA oxidizes, and there is a non-oxidized PUFA in the vicinity, the non-oxidized PUFA can get oxidized by the oxidized PUFA. This may also be referred to as autoxidation. In some instances, if there is a low concentration, for example "dilute" H-PUFAs in the membrane with D-PUFAs, this oxidation cycle may be broken due to the distance separating H-PUFAs. In some embodiments, the concentration of isotopically modified PUFAs is present in a sufficient amount to maintain autoxidation chain reaction. To break the autoxidation chain reaction, for example, 1-60%, 5-50%, or 15-35% of the total molecules of the same type are in the membrane.

Antioxidants

The compound can be administered with an antioxidant. In some embodiments, the antioxidant is selected from Coenzyme Q, idebenone, mitoquinone, mitoquinol, vitamin E, vitamin C, or any combination thereof.

Some examples of the antioxidants include, but are not limited to, vitamin E and derivative thereof, sodium metabisulfite, sodium thiosulfate, acetylcysteine, butylated hydroxyanisole and butylated hydroxytoluene. In some embodiments, the antioxidant is Vitamin E.

Although antioxidants cannot cancel the negative effects of PUFA peroxidation due to the stochastic nature of the process and the stability of PUFA peroxidation products (reactive carbonyls) to antioxidant treatment, co-administration of antioxidants with compositions resistant to oxidation, such as those described herein, may prove beneficial for treating oxidative stress-related disorders.

Certain antioxidants contemplated as useful for co-administration include the following: vitamins, such as vitamin C and vitamin E; glutathione, lipoic acid, uric acid, carotenes, lycopene, lutein, anthocyanins, oxalic acid, phytic acid, tannins, coenzyme Q, melatonin, tocopherols, tocotrienols, polyphenols including resveratrol, flavonoids, selenium, eugenol, idebenone, mitoquinone, mitoquinol, ubiquinone, Szeto-Schiller peptides, and mitochondrial-targeted antioxidants. When not explicitly mentioned, quinone derivatives of the aforementioned antioxidants are also contemplated as useful for co-administration.

In some embodiments, stabilized compounds are administered with compounds that upregulate antioxidant genes. In other embodiments, stabilized compounds are administered with compounds that affect signaling pathways, such as the Keap1/Nrf2/ARE signaling pathway, thereby resulting in the production of anti-inflammatory and/or antioxidant proteins, such as here oxygenase-1 (HO-1). In some embodiments, stabilized compounds are administered with antioxidant inflammation modulators. Antioxidant inflammation modulators suppress pro-oxidant and/or pro-inflammatory transcription factors. In some embodiments, antioxidant inflammation modulators are activators of the transcription factor Nrf2. Nrf2 activation promotes the antioxidant, detoxification, and anti-inflammatory genes upregulation. In other embodiments, antioxidant inflammation modulators suppress NF-κB. In some embodiments, antioxidant inflammation modulators suppress STAT3. In other embodiments, stabilized compounds are administered with compounds that affect histone deacetylase activity. In some embodiments, stabilized compounds are administered with compounds that bind to antioxidant response elements (ARE). In other embodiments, stabilized compounds are administered with bardoxolone methyl (2-cyano-3,12-dioxooleane-1,9(11)-dien-28-oic acid methyl ester) as the antioxidant inflammation modulator. In some embodiments, the antioxidant inflammation modulator is 2-cyano-3,12-dioxooleane-1,9(11)-dien-28-oic acid, or a pharmaceutically acceptable ester thereof. In other embodiments, the antioxidant inflammation modulator is an amide of 2-cyano-3,12-dioxooleane-1,9(11)-dien-28-oic acid. In some embodiments, the antioxidant inflammation modulator is a triterpenoid. In other embodiments, the antioxidant inflammation modulator is selected from the following compounds:

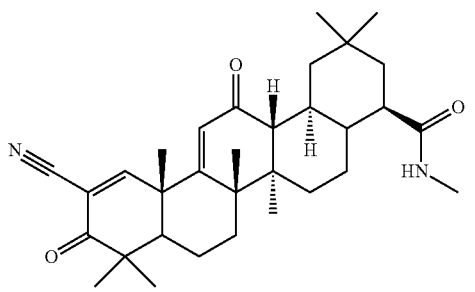

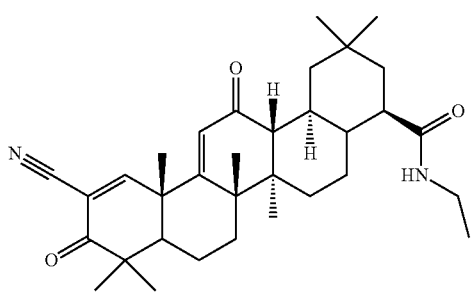

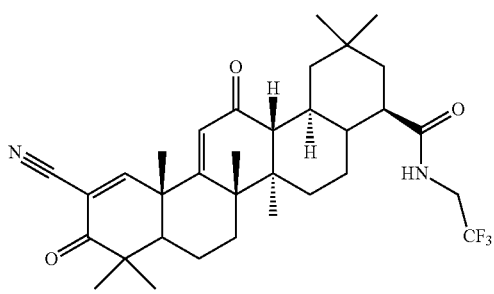

-continued

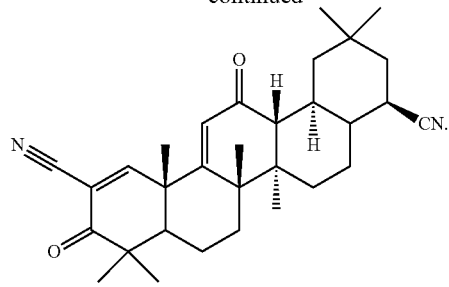

Additional antioxidants believed to be useful in co-administration therapies include those compounds disclosed in U.S. Pat. Nos. 6,331,532; 7,179,928; 7,232,809; 7,888,334; 7,888,335; 7,432,305; 7,470,798; and 7,514,461; and U.S. Patent Publication Nos. 20020052342; 20030069208; 20040106579; 20050043553; 20050245487; 20060229278; 20070238709; 20070270381; 20080161267; 20080275005; 20090258841; 20100029706; and 20110046219; in which the compounds disclosed therein are incorporated by reference. These compounds are mitochondria-targeted compounds and include, but are not limited to:

Compounds of Formulas I or II

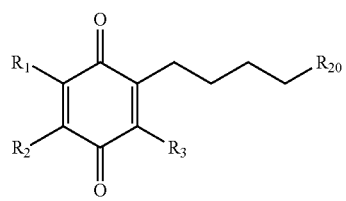

Formula I or

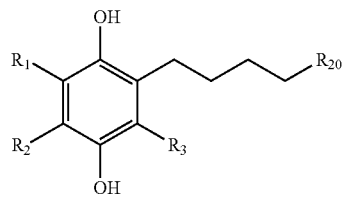

Formula II wherein $R^1$ and $R^2$ are independently selected from —$C_1$-$C_4$ alkyl, —$C_1$-$C_4$ haloalkyl, —CN, —F, —Cl, —Br, and —I; $R_3$ is selected from —$C_1$-$C_4$ alkyl, —$C_1$-$C_4$ haloakyl, —CN, —F, —Cl, and —I, and $R_{20}$ is independently selected from —$C_1$-$C_{20}$ alkyl, —$C_1$-$C_{20}$ alkenyl, —$C_1$-$C_{20}$ alkynyl, and —$C_1$-$C_{20}$ containing at least one double bond and at least one triple bond.

Compounds such as: 3-(6-Hydroxy-2-methyl-3,4,7,8,9,10-hexahydro-7,10-methano-2H-benzo[h]chromen-2-yl-propionic acid methyl ester; 3-(6-Hydroxy-2-methyl-3,4,7,8,9,10-hexahydro-7,10-methano-2H-benzo[h]chroman-2-yl)-propionic acid; 2,2,-Dimethyl-3,4,7,8,9,10-hexahydro-7,10-methano-2H-benzo[h]chromen-6-ol; 3-(6-Hydroxy-2-methyl-3,4,7,8,9,10-hexahydro-7,10-propano-2H-benzo[h]chromen-2-yl)-propionic acid methyl ester; 2-Methyl-2-[3-(thiazol-2-ylsulfanyl)-propyl]-3,4,7,8,9,10-hexahydro-7,10-methano-2H-benzo[h]chromen-6-ol, [3-(6-Hydroxy-2-methyl-3,4,7,8,9,10-hexahydro-7,10-methano-2H-benzo[h]chromen-2-yl)-propyl]-phosphonic acid dimethyl ester; [3-(6-Hydroxy-2-methyl-3,4,7,8,9,10-hexahydro-7,10-methano-2H-benzo[h]chromen-2-yl)-propyl]-phosphonic acid; 3-(6-Hydroxy-2-methyl-3,4,7,8,9,10-hexahydro-7,10- methano-2H-benzo[h]chromen-2-yl)-propionic acid methyl ester; 4-(6-Hydroxy-2-methyl-3,4,7,8,9,10-hexahydro-7,10-methano-2H-benzo[h]chromen-2-yl)-butane-1-sulfonic acid dimethylamide; 2-(3-Hydroxy-propyl)-2-methyl-3,4,7,8,9,10-hexahydro-7,10-methano-2H-benzo[h]chromen-6-ol; 2-(3-Chloro-propyl)-2-methyl-3,4,7,8,9,10-hexahydro-7,10-methano-2H-benzo[h]chromen-6-ol 2,2-Dimethyl-3,4,7,8,9,10-hexahydro-7,10-methano-2H-benzo[h]chromen-6-ol; -(2-Chloro-ethyl)-2-methyl-3,4,7,8,9,10-hexahydro-7,10-methano-2H-benzo[h]chromen-6-ol; 2-Methyl-2-thiazol-2-yl-3,4,7,8,9,10-hexahydro-7,10-methano-2H-benzo[h]chromen-6-ol 2,2-Dimethyl-3,4,7,8,9,10-hexahydro-7,10-ethano-2H-benzo[h]chromen-6-ol 3-(6-Hydroxy-2-methyl-3,4,7,8,9,10-hexahydro-7,10-ethano-2H-benzo[h]chromen-2-yl)-propionic acid; 2-(3-Chloro-propyl)-2-methyl-3,4,7,8,9,10-hexahydro-7,10-ethano-2H-benzo[h]chromen-6-ol; 4-(6-Hydroxy-2,2-dimethyl-3,4,7,8,9,10-hexahydro-7,10-methano-2H-benzo[h]chromen-5-ylmethylene)-2-methyl-5-propyl-2,4-dihydro-pyrazol-3-one:

Compounds such as: 2,2,7,8-Tetramethyl-5-phenyl-chroman-6-ol; 4-(6-Hydroxy-2,2,7,8-tetramethyl-chroman-5-yl)-benzoic acid methyl ester; 4-(6-Hydroxy-2,2,7,8-tetramethyl-chroman-5-yl)-benzoic acid; 2,2,7,8-Tetramethyl-5-pyridin-4-yl-chroman-6-ol; 2,2,7,8-Tetramethyl-5-pyridin-3-yl-chroman-6-ol; 5-(4-Methanesulfonyl-phenyl)-2,2,7,8-tetramethyl-chroman-6-ol; 5-(4-Dimethylamino-phenyl)-2,2,7,8-tetramethyl-chroman-6-ol; 5-(4-Chloro-phenyl)-2,2,7,8-tetramethyl-chroman-6-ol; 4-(6-Hydroxy-2,2,7,8-tetramethyl-chroman-5-yl)-benzenesulfonamide; 5-(4-Methoxy-phenyl)-2,2,7,8-tetramethyl-chroman-6-ol; (6-Hydroxy-2,2,7,8-tetramethyl-chroman-5-ylmethyl)-1-hydroxyurea; 2,2,7,8-Tetramethyl-5-(3-nitro-phenyl)-chroman-6-ol, 2,2,7,8-Tetramethyl-5-(4-trifluoromethyl-phenyl)-chroman-6-ol; 5-(4-tert-Butyl-phenyl)-2,2,7,8-tetramethyl-chroman-6-ol; 2,2,7,8-Tetramethyl-5-(3,4,5-trimethoxy-phenyl)-chroman-6-ol; 4-(6-Hydroxy-2,2,7,8-tetramethyl-chroman-5-yl)-benzonitrile; 5-(2,5-Dimethoxy-3,4-dimethyl-phenyl)-2,2,7,8-tetramethyl-chroman-6-ol; 5-(6-Hydroxy-2,2,7,8-tetramethyl-chroman-5-yl)-benzene-1,2,3-triol; 6-Hydroxy-2,2,7,8-tetramethyl-chroman-5-yl)-2, 3-dimethyl-benzene-1,4-diol; 5-(2-Chloro-phenyl)-2,2,7,8-tetramethyl-chroman-6-ol; 5-Furan-2-yl-2,2,7,8-tetramethyl-chroman-6-ol; 5-Allylsulfanylmethyl-2,2,8-trimethyl-7-(3-methyl-butyl)-chroman-6-ol; 5-Cyclopentylsulfanylmethyl-2,2,7,8-tetramethyl-chroman-6-ol; 5-Hexylsulfanylmethyl-2,2,7,8-tetramethyl-chroman-6-ol; 5-Allylsulfanylmethyl-2,2,7,8-tetramethyl-chroman-6-ol; 5-(4,6-Dimethyl-pyrimidin-2-ysulfanylmethyl)-2,2,7,8-tetramethyl-chroman-6-ol; 1-[3-(6-Hydroxy-2,2,7,8-tetramethyl-chroman-5-yl-methylsulfanyl)-2-methyl-propionyl]-pyrrolidine-2-carboxylic acid; 4-(6-Hydroxy-2,2,7,8-tetramethyl-chroman-5-ylmethylene)-5-methyl-2-phenyl-2,4-dihydro-pyrazol-3-one; 4-(6-Hydroxy-2,2,7,8-tetramethyl-chroman-5-yl-methylene)-3-phenyl-4H-isoxazol-5-one; 4-[4-(6-Hydroxy-2,2,7,8-tetramethyl-chroman-5-yl-methylene)-3-methyl-5-oxo-4,5-dihydro-pyrazol-1-yl]-benzoic acid; 4-(6-Hydroxy-2,2,7,8-tetramethyl-chroman-5-yl-methylene)-2-methyl-5-propyl-2,4-dihydro-pyrazol-3-one; 5-Hydroxy-3-(6-hydroxy-2,2,7,8-tetramethyl-chroman-5-yl-methylene)-3H-benzofuran-2-one; 2,5,7,8-Tetramethyl-2-thiophen-2-yl-chroman-6-ol; 2-(2,5-Dimethyl-thiophen-3-yl)-2,5,7,8-tetramethyl-chroman-6-ol; 2-(2,5-Dimethyl-thiophen-3-yl)-2,7,8-trimethyl-chroman-6-ol; 8-Chloro-2-(2,5-dimethyl-thiophen-3-yl)-2,5,7-trimethyl-chroman-6-ol; 5-Chloro-2,7,8-trimethyl-2-thiophen-2-yl-chroman-6-ol; 5-[3-(6-Methoxymethoxy-2,7,8-trimethyl-chroman-2-yl)-propylidene]-thiazolidine-2,4-dione; 5-[3-(6-Hydroxy-2,7,8-trimethyl-chroman-2-yl)-propylidene]-thiazolidine-2,4-dione; 3-[6-Hydroxy-2,7,8-trimethyl-2-(4,8,12-trimethyl-tridecyl)-chroman-5-yl-methylsulfanyl]-2-methyl-propionic acid; 2,7,8-Trimethyl-5-(5-methyl-1H-benzoimidazol-2-yl-sulfanylmethyl)-2-(4,8,12-trimethyl-tridecyl)-chroman-6-ol; 2-[6-Hydroxy-2,7,8-trimethyl-2-(4,8,12-trimethyl-tridecyl)-chroman-5-ylmethylsulfanyl]-ethanesulfonic acid; 5-(4,6-Dimethyl-pyrimidin-2-ylsulfanylmethyl)-2,7,8-trimethyl-2-(4,8,12-trimethyl-tridecyl)-chroman-6-ol; 4-[2-(4,8-Dimethyl-tridecyl)-6-hydroxy-2,7,8-trimethyl-chroman-5-ylmethylsulfanyl]-benzoic acid; 1-{3-[6-Hydroxy-2,7,8-trimethyl-2-(4,8,12-trimethyl-tridecyl)-chroman-5-ylmethylsulfanyl]-2-methyl-propionyl}-pyrrolidine-2-carboxylic acid; 2-(2,2-Dichloro-vinyl)-2,5,7,8-tetramethyl-chroman-6-ol; 2-(2,2-Dibromo-vinyl)-2,5,7,8-tetramethyl-chroman-6-ol; 5-(5-Chloro-3-methyl-pent-2-enyl)-2,2,7,8-tetramethyl-chroman-6-ol; 5-Chloro-2-(2,5-dimethyl-thiophen-3-yl)-2,7,8-trimethyl-chroman-6-ol; 2-(3-Chloro-propyl)-5,7-dimethyl-2-thiophen-2-yl-chroman-6-ol; 5-Chloro-2-(2,5-dimethyl-thiazol-4-yl)-2,7,8-trimethyl-chroman-6-ol; 5-Chloro-2-(2,5-dimethyl-thiazol-4-yl)-2,7,8-trimethyl-2H-chromen-6-ol; and 5-Chloro-2-(2,5-dim-ethyl-thiazol-4-yl)-2,7,8-trimethyl-chroman-6-ol.

Compounds such as: dimebolin (2,8-dimethyl-5-(2-(6-methylpyridin-3-yl)ethyl)-2,3,4,5-tetrahydro-1H-pyrido[4,3b]indole), 8-chloro-2-methyl-5-(2-(6-methylpyridin-3-yl)ethyl)-2,3,4,5-tetrahydro-1H-pyrido[4,3-b]indole), mebhydroline (5-benzyl-2-methyl-2,3,4,5-tetrahydro-1H-pyrido[4,3-b]indole), 2,8-dimethyl-1,3,4,4a,5,9b-hexahydro-1H-pyrido[4,3-b]indole, 8-fluoro-2-(3-(pyridin-3-yl)propyl)-2,3,4,5-tetrahydro-1H-pyrido[4,3-b]indole, and 8-methyl-1,3,4,4a,5,9b-tetranydro-1H-pyrido[4,3-b]indole.

Compounds such as: 2-(3-hydroxy-3-methylbutyl)-3,5-dimethyl-6-(4-(trifluoromethyl)phenyl)cyclohexa-2,5-diene-1,4-dione; 2-(3-hydroxy-3-methylbutyl)-6-(4-methoxyphenyl)-3,5-dimethylcyclohexa-2,5-diene-1,4-dione; 4-(5-(3-hydroxy-3-methylbutyl)-2,4-dimethyl-3,6-dioxocyclohexa-1,4-dienyl)benzonitrile; 2-(3-hydroxy-3-methylbutyl)-3,5-dimethyl-6-(naphthalen-2-yl)cyclohexa-2,5-diene-1,4-dione; 2-(3,4-difluorophenyl)-6-(3-hydroxy-3-methylbutyl)-3,5-dimethylcyclohexa-2,5-diene-1,4-dione; 2-(4-fluorophenyl)-6-(3-hydroxy-3-methylbutyl)-3,5-dim-ethylcyclohexa-2,5-diene-1,4-dione; 2-(4-chlorophenyl)-6-(3-hydroxy-3-methylbutyl)-3,5-dimethylcyclohexa-2,5-diene-1,4-dione; 2-(2,3-dihydrobenzofuran-2-yl)-6-(3-hydroxy-3-methylbutyl)-3,5-dimethylcyclohexa-2,5-diene-1,4-dione; 2-(3-hydroxy-3-methylbutyl)-5,6-dimethyl-3-phenethylcyclohexa-2,5-diene-1,4-dione; 2-(3-hydroxy-3-methylbutyl)-5,6-dimethyl-3-phenylcyclohexa-2,5-diene-1,4-dione; 2-benzyl-3-(3-hydroxy-3-methylbutyl)-5,6-dimethylcyclohexa-2,5-diene-1,4-dione; 2-(3-hydroxy-3-methylbutyl)-5,6-dimethyl-3-(3-phenylpropyl)cyclohexa-2,5-diene-1,4-dione; 2-(1-hydroxy-2-phenylethyl)-3-(3-hydroxy-3-methylbutyl)-5,6-dimethylcyclohexa-2,5-diene-1,4-dione; 2-(3-hydroxy-3-methylbutyl)-3-(4-methoxyphenyl)-5,6-dimethyl-cyclohexa-2,5-diene-1,4-dione 2-(3-hydroxy-3-methylbutyl)-5,6-dimethyl-3-(4-(trifluoromethyl)-phenyl)cyclohexa-2,5-diene-1,4-dione; 2-(3-hydroxy-3-methylbutyl)-5,6-dimethyl-3-(naphthaten-2-yl)cyclohexa-2,5-diene-1,4-dione; 2-(benzofuran-2-yl)-3-(3-hydroxy-3-methylbutyl)-5,6-dimethylcyclohexa-2,5-diene-1,4-dione; 2-(4-chlorophenyl)-3-(3-hydroxy-3-methylbutyl)-5,6-dimethylcyclohexa-2,5-diene-1,4-dione; 2-(4-ethylphenyl)-3-(3-hydroxy-3-methylbutyl)-5,6-dim-ethylcyclohexa-2,5-diene-1,4-dione, 2-(3-hydroxy-3-methylbutyl)-5,6-dimethyl-3-(3-(trifluoromethyl)phenyl)-cyclohexa-2,5-diene-1,4-dione; 2-(4-tert-butylphenyl)-3-(3-hydroxy-3-methylbutyl)-5,6-dimethyl-cyclohexa-2,5-diene-1,4-dione; 2-(4-fluorophenyl)-3-(3-hydroxy-3-methylbutyl)-5,6-dimethyleydohexa-2,5-diene-1,4-dione; 2-(3-fluorophenyl)-3-(3-hydroxy-3-methylbutyl)-5,6-dimethylcyclohexa-2,5-diene-1,4-dione; 4-(2-(3-hydroxy-3-methylbutyl)-4,5-dimethyl-3,6-dioxocyclohexa-1,4-dienyl)benzonitrile; 2-(3,4-difluorophenyl)-3-(3-hydroxy-3-methylbutyl)-5,6-dimethyl-cyclohexa-2,5-diene-1,4-dione, 2-(2-fluorophenyl)-3-(3-hydroxy-3-methylbutyl)-5,6-dimethylcyclohexa-2,5-diene-1,4-dione; 2-(3-hydroxy-3-methylbutyl)-3-(3-methoxyphenyl)-5,6-dimethyl-cyclohexa-2,5-diene-1,4-dione; 2-(4-fluoro-2-methoxyphenyl)-3-(3-hydroxy-3-methylbutyl)-5,6-dimethylcyclohexa-2,5-diene-1,4-dione; 2-(benzo[d][1,3]dioxol-5-yl)-3-(3-hydroxy-3-methylbutyl)-5,6-dimethylcyclohexa-2,5-diene-1,4-dione; 2-(2,4-difluorophenyl)-3-(3-hydroxy-3-methylbutyl)-5,6-dimethylcyclohexa-2,5-diene-1,4-dione; 2-(3-hydroxy-3-methylbutyl)-3-(4-methoxyphenyl)-5,6-dimethylcyclohexa-2,5-diene-1,4-dione; 2-(3,5-bis(trifluoromethyl)phenyl)-3-(3-hydroxy-3-methylbutyl)-5,6-dimethylcyclohexa-2,5-diene-1,4-dione; 2-(4-chlorophenyl)-6-(3-hydroxy-3-methylbutyl)-3,5-dimethylcyclohexa-2,5-diene-1,4-dione; 2-(3-hydroxy-3-methylbutyl)-5,6-dimethyl-3-(2-(thiazol-2-yl)ethyl)cyclohexa-2,5-diene-1,4-dione; 2-(3-hydroxy-3-methylbutyl)-5,6-dimethyl-3-(2-thiazol-5-yl)ethyl)cyclohexa-2,5-diene-1,4-dione; 2-(3-hydroxy-3-methylbutyl)-5,6-dimethyl-3-(2-(pyridin-2-yl)ethyl)cyclohexa-2,5-diene-1,4-dione; 2-(3-hydroxy-3-methylbutyl)-5,6-dimethyl-3-(2-(pyridazin-4-yl)ethyl)cyclohexa-2,5-diene-1,4-dione; 2-(3-hydroxy-3-methylbutyl)-5,6-dimethyl-3-(2-(thiophen-2-yl)ethyl)cyclohexa-2,5-diene-1,4-dione; 2-(3-hydroxy-3-methylbutyl)-5,6-dimethyl-3-(2-(thiophen-3-yl)ethyl)cyclohexa-2,5-diene-1,4-dione; 2-(2-(furan-2-yl)ethyl)-3-(3-hydroxy-3-methylbutyl)-5,6-dimethylcyclohexa-2,5-diene-1,4-dione; 2-(2-(furan-3-yl)ethyl)-3-(3-hydroxy-3-methylbutyl)-5,6-dimethylcyclohexa-2,5-diene-1,4-dione; 2-(2-(1H-pyrazol-5-yl)ethyl)-3-(3-hydroxy-3-methyl butyl)-5,6-dimethylcyclohexa-2,5-diene-1,4-dione; 2-(2-(1H-pyrazol-4-yl)ethyl)-3-(3-hydroxy-3-methylbutyl)-5,6-dimethylcyclohexa-2,5-diene-1,4-dione; 2-(2-1H-pyrazol-1-yl)ethyl)-3-(3-hydroxy-3-methylbutyl)-5,6-dimethylcyclohexa-2,5-diene-1,4-dione; 2-(2-(1H-imidazol-5-yl)ethyl)-3-(3-hydroxy-3-methylbutyl)-5,6-dimethylcyclohexa-2,5-diene-1,4-dione; 2-(2-(1H-imidazol-2-yl)ethyl)-3-(3-hydroxy-3-methylbutyl)-5,6-dimethylcyclohexa-2,5-diene-1,4-dione; 2-(3-hydroxy-3-methylbutyl)-5,6-dimethyl-3-(2-(oxazol-5-yl)ethyl)cyclohexa-2,5-diene-1,4-dione; 2-(3-hydroxy-3-methylbutyl)-5,6-dimethyl-3-(2-(oxazol-2-yl)ethyl)cyclohexa-2,5-diene-1,4-dione; 2-(3-hydroxy-3-methylbutyl)-5,6-dimethyl-3-(2-(oxazol-4-yl)ethyl)cyclohexa-2,5-diene-1,4-dione; and 2-(2-(1H-indol-3-yl)ethyl)-3-(3-hydroxy-3-methylbutyl)-5,6-dimethylcyclohexa-2,5-diene-1,4-dione.

Compounds such as:

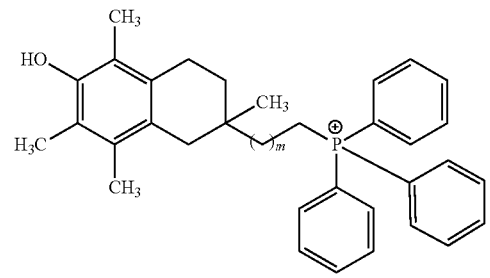

wherein m is —$C_1$-$C_{20}$ alkyl, —$C_1$-$C_{20}$ alkenyl, alkynyl, or —$C_1$-$C_{20}$ containing at least one double bond and at least one triple bond, and the counterion is a pharmaceutically acceptable anion.

Compounds such as: 3-(4,5-dimethoxy-2-methyl-3,6-dioxo-1,4-cyclohexadien-1-yl)propyl triphenylphosphonium salts; 4-(4,5-dimethoxy-2-methyl-3,6-dioxo-1,4-cyclohexadien-1-yl)butyl triphenylphosphonium salts; 5-(4,5-dimethoxy-2-methyl-3,6-dioxo-1,4-cyclohexadien-1-yl)pentyl triphenylphosphonium salts; 6-(4,5-dimethoxy-2-methyl-3,6-dioxo-1,4-cyclohexadien-1-yl)hexyl triphenylphosphonium salts; 7-(4,5-dimethoxy-2-methyl-3,6-dioxo-1,4-cyclohexadien-1-yl)heptyl triphenylphosphonium salts; 8-(4,5-dimethoxy-2-methyl-3,6-dioxo-1,4-cyclohexadien-1-yl)octyl triphenylphosphonium salts; 9-(4,5-dimethoxy-2-methyl-3,6-dioxo-1,4-cyclohexadien-1-yl)nonyl triphenylphosphonium salts; 10-(4,5-dimethoxy-2-methyl-3,6-dioxo-1,4-cyclohexadien-1-yl)decyl triphenylphosphonium salts; 11-(4,5-dimethoxy-2-methyl-3,6-dioxo-1,4-cyclohexadien-1-yl)undecyl triphenylphosphonium salts; 12-(4,5-dimethoxy-2-methyl-3,6-dioxo-1,4-cyclohexadien-1-yl)dodecyl triphenylphosphonium salts; 13-(4,5-dimethoxy-2-methyl-3,6-dioxo-1,4-cyclohexadien-1-yl)propyldecyl triphenylphosphonium salts; 14-(4,5-dimethoxy-2-methyl-3,6-dioxo-1,4-cyclohexadien-1-yl)butyldecyl triphenylphosphonium salts; 15-(4,5-dimethoxy-2-methyl-3,6-dioxo-1,4-cyclohexadien-1-yl)pentadecyl triphenylphosphonium salts; 16-(4,5-dimethoxy-2-methyl-3,6-dioxo-1,4-cyclohexadien-1-yl)hexadecyl triphenylphosphonium salts; 17-(4,5-dimethoxy-2-methyl-3,6-dioxo-1,4-cyclohexadien-1-yl)heptadecyl triphenylphosphonium salts; 18-(4,5-dimethoxy-2-methyl-3,6-dioxo-1,4-cyclohexadien-1-yl)octadecyl triphenylphosphonium salts; 19-(4,5-dimethoxy-2-methyl-3,6-dioxo-1,4-cyclohexadien-1-yl)nonadecyl triphenylphosphonium salts; 20-(4,5-dimethoxy-2-methyl-3,6-dioxo-1,4-cyclohexadien-1-yl)icosyl triphenylphosphonium salts; 3-(4,5-dimethoxy-2-methyl-3,6-dihydroxyphenyl)propyl triphenylphosphonium salts; 4-(4,5-dimethoxy-2-methyl-3,6-dihydroxyphenyl)butyl triphenylphosphonium salts; 5-(4,5-dimethoxy-2-methyl-3,6-dihydroxyphenyl)pentyl triphenylphosphonium salts; 6-(4,5-dimethoxy-2-methyl-3,6-dihydroxyphenyl)hexyl triphenylphosphonium salts; 7-(4,5-dimethoxy-2-methyl-3,6-dihydroxyphenyl)heptyl triphenylphosphonium salts; 8-(4,5-dimethoxy-2-methyl-3,6-dihydroxyphenyl)octyl triphenylphosphonium salts; 9-(4,5-dimethoxy-2-methyl-3,6-dihydroxyphenyl)nonyl triphenylphosphonium salts; 10-(4,5-dimethoxy-2-methyl-3,6-dihydroxyphenyl)decyl triphenylphosphonium salts; 11-(4,5-dimethoxy-2-methyl-3,6-dihydroxyphenyl)undecyl triphenylphosphonium salts; 12-(4,5-dimethoxy-2-methyl-3,6-dihydroxyphenyl)dodecyl triphenylphosphonium salts; 13-(4,5-dimethoxy-2-methyl-3,6-dihydroxybenzyl)propyldecyl triphenylphosphonium salts; 14-(4,5-dimethoxy-2-methyl-3,6-dihydroxyphenyl)

butyldecyl triphenylphosphonium salts; 15-(4,5-dimethoxy-2-methyl-3,6-dihydroxyphenyl)pentadecyl triphenylphosphonium salts; 16-(4,5-dimethoxy-2-methyl-3,6-dihydroxyphenyl)hexadecyl triphenylphosphonium salts; 17-(4,5-dimethoxy-2-methyl-3,6-dihydroxyphenyl)heptadecyl triphenylphosphonium salts; 18-(4,5-dimethoxy-2-methyl-3,6-dihydroxyphenyl)octadecyl triphenylphosphonium salts; 19-(4,5-dimethoxy-2-methyl-3,6-dihydroxyphenyl)nonadecyl triphenylphosphonium salts; 20-(4,5-dimethoxy-2-methyl-3,6-dihydroxyphenyl)icosyl triphenylphosphonium salts; wherein the counterion of the salt is a pharmaceutically acceptable anion such as bromide, methanesulfonate ethanesulfonate, propanesulfonate, benzenesulfonate, p-toluenesulfonate, or 2-naphthylene sulfonate.

Additionally, it is contemplated that co-administration of antioxidants could take the form of consuming foods known to have increased levels of beneficial antioxidants. Such foods include both regular foods and "superfoods" which contain antioxidants. These foods include fruits, vegetables, and other foodstuffs such as strawberries, blackcurrants, blackberries, oranges, blueberries, pomegranates, tea, coffee, olive oil, chocolate, cinnamon, herbs, red wine, grain cereals, eggs, meat, legumes, nuts, spinach, turnip, rhubarb, cocoa beans, maize, beans, cabbage, and the like.

Administration and Compositions

The compounds are preferably administered at a therapeutically effective dosage. While human dosage levels for the compounds described herein may vary, generally, a daily dose (or dosing 2, 3, or 4 times a day) of the isotopically modified polyunsaturated fatty acid substance (e.g., isotopically-modified polyunsaturated fatty acid, an isotopically-modified polyunsaturated fatty acid ester, an isotopically-modified polyunsaturated fatty acid thioester, an isotopically-modified polyunsaturated fatty acid amide, a polyunsaturated fatty acid mimetic, or an isotopically-modified fatty acid pro-drug) may be about the same as or 0.1, 0.15, 0.2, 0.3, 0.4, 0.5, 0.6, 0.7, 0.8, 0.9, 1.2, 1.4, 1.5, 1.75, 2, 3, 4, 5 or more times as much of the corresponding unmodified compound the subject would typically ingest in their diet, displacing some or most or all of the unmodified compound. Thus, for an adult with a normal intake of 15-20 g of PUFA per day, a daily dosage of isotopically-modified polyunsaturated fatty acid substance preferably ranges from 1, 1.5, or 2 g up to 15, 20, 30, 40 g or more. It is preferred that the isotopically-modified polyunsaturated fatty acid substance comprise at least 10, 15, or 20% of the subject's daily PUFA intake, and may comprise up to 90%, 95%, 99% or more of the subject's daily PUFA intake. An objective of the therapy is to replace a significant amount of the PUFA in the body with isotopically-modified PUFA or metabolites thereof, such that about 10%, 15%, 20%, 25%, 30%, 35%, 40%, 50% or more of PUFA or PUFA metabolites in the body is isotopically modified. Put another way, by repeatedly administering the isotopically-modified polyunsaturated fatty acid substances to the patient, such that a significant percentage of the PUFA or metabolites thereof in the body (or at a local site of interest) is isotopically-modified, the modified compound will be resistant to oxidiation in its own right but will also be present in an amount effective to reduce oxidation of the unmodified PUFA or metabolites thereof present in the body.

In some embodiments, the amount of the isotopically modified polyunsaturated fatty acid substance administered to the subject is a therapeutically active dose at about 0.01%, 0.05%, 0.075%, 0.1%, 0.5%, 1.0%, 1.5%, 2%, 3%, 4%, 5%, 6%, 7%, 8%, 9%, 10%, 20%, 30%, 40%, 50%, 60%, 70%, 80%, 90%, 100%, 120%, 150%, 180%, or 200% of the amount of the unmodified polyunsaturated fatty acid substance ingested by the subject. In some embodiments, the amount of the isotopically modified polyunsaturated fatty acid substance administered to the subject is more than about 0.01%, 0.05%, 0.075%, 0.1%, 0.5%, 1.0%, 1.5%, 2%, 3%, 4%, 5%, 6%, 7%, 8%, 9%, 10%, 20%, 30%, 40%, 50%, 60%, 70%, 80%, 90%, 100%, 120%, 150%, 180%, or 200% of the amount of the unmodified polyunsaturated fatty acid substance ingested by the subject. In some embodiments, the amount of the isotopically modified polyunsaturated fatty acid substance administered to the subject is less than about 0.01%, 0.05%, 0.075%, 0.1%, 0.5%, 1.0%, 1.5%, 2%, 3%, 4%, 5%, 6%, 7%, 8%, 9%, 10%, 20%, 30%, 40%, 50%, 60%, 70%, 80%, 90%, 100%, 120%, 150%, 180%, or 200% of the amount of the unmodified polyunsaturated fatty acid substance ingested by the subject. In some embodiments, the amount of the isotopically modified polyunsaturated fatty acid substance administered to the subject is in the range of about 0.01%-20%, 0.1%-20%, 1-50%, 10-50%, 50%-80%, 50%-100%, 1-200%, 10%-200%, 10%-100%, or 20%-100% of the amount of the unmodified polyunsaturated fatty acid substance ingested by the subject.

In some embodiments, the amount of the isotopically modified polyunsaturated fatty acid substance administered to the subject meets a daily dietary requirement referenced for the unmodified polyunsaturated fatty acid substance. In some embodiments, the amount of isotopically modified linoleic acid administered to the subject is in the range of about 1 g to 100 g per day. In some embodiments, the amount of isotopically modified omega 6 polyunsaturated fatty acid is in the range of about 3 g to about 10 g per day. In some embodiments, the amount of isotopically modified omega 3 polyunsaturated fatty acid is in the range of about 0.2 g to about 5 g per day. In some embodiments, the amount of isotopically modified arachidonic acid is about 2.5 g per day. In some embodiments, the amount of isotopically modified arachidonic acid is about 0.5 g to about 5 g per day. In some embodiments, the amount of isotopically modified. Docosahexaenoic acid is about 0.5 g per day. In some embodiments, the amount of isotopically modified Docosahexaenoic acid is in the range of about 0.1 g to about 2 g per day.

The compounds or compositions can be formulated into various delivery systems for administration. Some examples of delivery system forms include but are not limited to solutions, colloids, biopolymer matrices, micelles, powders, emulsions (e.g., conventional emulsions, multiple emulsions, multilayer emulsions), solid lipid particles, and filled hydrogel particles. Each of these delivery systems can be produced from food-grade (GRAS) ingredients (e.g., lipids, proteins, polysaccharides, surfactants, or minerals) using various processing operations (e.g., mixing, homogenizing, or thermal processing). In some embodiments, the emulsion delivery system can be an excipient emulsion including an excipient nanoemulsion. In some embodiments, the delivery system can be a lipid-based delivery system. In some embodiments, the delivery system can be a colloidal system including vesicles or micelles (e.g., mixed micelles or uniform micelles). Other examples of delivery systems can be found in Porter C.; et al., *Nat Rev Drug Discov.* 2007 March; 6(3):231-48.; Ruojie Zheng, et al., *Food Biophysics* (2016) 11: 71; and McClements D J, et al.; *J Food Sci.* 2007 October; 72(8):R109-2; which are incorporated into the application for this purpose in their entireties.

Administration of the compounds or compositions disclosed herein can be via any of the accepted modes of administration for agents that serve similar utilities including, but not limited to, orally, subcutaneously, intravenously, intranasally, topically, transdermally, intraperitoneally, intramuscularly, intrapulmonarily, vaginally, rectally, or intraocularly. Oral and parenteral administrations are customary in treating the indications that are the subject of the preferred embodiments. In some embodiments, administration of the compounds or compositions described herein refer to administration through ingestion. In some embodiments, the compounds or compositions described herein are administered orally.

The compounds or compositions useful as described above can be formulated into pharmaceutical compositions, nutraceutical compositions, or food supplement. Standard pharmaceutical formulation techniques are used, such as those disclosed in Remington's The Science and Practice of Pharmacy, 21st Ed., Lippincott Williams & Wilkins (2005), incorporated by reference in its entirety. Accordingly, some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof; and (b) a pharmaceutically acceptable carrier, diluent, excipient or combination thereof.

In addition to the selected compound useful as described above, some embodiments include compositions containing a pharmaceutically-acceptable carrier. The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions comprise compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired PH, including but not limited to NaOH, sodium carbonate, sodium acetate, HCl, and citric acid. In various embodiments, the OH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

Method for Treatment

Some embodiments relate to a method including identifying a subject having impaired aldehyde dehydrogenase activity; and administering to the subject a compound comprising an isotopically-modified polyunsaturated fatty acid, an isotopically-modified polyunsaturated fatty acid ester, an isotopically-modified polyunsaturated fatty acid thioester, an isotopically-modified polyunsaturated fatty acid amide, a polyunsaturated fatty acid mimetic, or an isotopically-modified polyunsaturated fatty acid pro-drug, the compound having an isotopic modification that reduces oxidation of the compound, thereby reducing production in the subject of one or more metabolic products associated with the aldehyde dehydrogenase. In some embodiments, the metabolic product is an aldehyde. In some embodiments, the metabolic product is malondialdehyde. In some embodiments, the metabolic product is 4-hydroxynonenal. In some embodiments, the metabolic product is 4-hydroxyhexenal. In some embodiments, the metabolic product is 3,4-dihydroxyphenylacetaldehyde (DOPAL). In some embodiments, the metabolic product is retinol. In some embodiments, the metabolic product is retinal aldehyde.

In some embodiments, the subject has an impaired mitochondrial aldehyde dehydrogenase activity. In some embodiments, the subject has an impaired retinol dehydrogenase activity.

In some embodiments, the ALDH enzymes can be selected from those listed in Table 1 below and also for the ALDH enzymes in Marchitti et al., *Expert Opin Drug Metab Toxicol*. 2008 June; 4(6):697-720; and Marchitti et al., Pharmacol Rev. 2007 June; 59(2):125-50. Epub 2007, the disclosure of which are incorporated herein by reference in their entireties for this purpose.

TABLE 1

Non-limited examples of human ALDH isozymes

| ALDH | Subcellular location | Preferred substrate |
| --- | --- | --- |
| ALDH1A1 | cytosol | Retinal |
| ALDH1A2 | cytosol | Retinal |
| ALDH1A3 | cytosol | retinal |
| ALDH1B1 | mitochondria | Aliphatic aldehydes |
| ALDH1L1 | cytosol | 10-Formyl tetrahydrofolate |
| ALDH1L2 | Unknown | unknown |
| ALDH2 | Mitochondria | Acetaldehyde, 4-HNE and MDA |
| ALDH3A1 | Cytosol, nucleus | Aromatic, aliphatic aldehydes |
| ALDH3A2 | Microsomes, peroxisomes | Fatty aldehydes |
| ALDH3B1 | cytosol | unknown |
| ALDH3B2 | Unknown | Unknown |
| ALDH4A1 | Mitochondria | Glutamate γ-semi-aldehyde |
| ALDH5A1 | Mitochondria | Succinate semi-aldehyde |
| ALDH6A1 | Mitochondria | Malonate semi-aldehyde |
| ALDH7A1 | Cytosol, nucleus, mitochondria | α-Aminoadipic semi-aldehyde |
| ALDH8A1 | cytosol | retinal |
| ALDH9A1 | cytosol | γ-Aminobutyr-aldehyde |
| ALDH16A1 | unknown | Unknown |
| ALDH18A1 | mitochondria | Glutamic γ-semi-aldehyde |

In some embodiments, the subject has or is at risk for neuropathy and the amount of the compound administered is sufficient to prevent or inhibit the progression of neuropathy. In some embodiments, the neuropathy is Alzheimer disease.

In some embodiments, the subject has or is at risk for early onset of Alzheimer disease and the amount of the compound administered is sufficient to prevent or inhibit the progression of early onset of Alzheimer disease. In some embodiments, the subject has or is at risk for late onset of Alzheimer disease and the amount of the compound administered is sufficient to prevent or inhibit the progression of late onset of Alzheimer disease.

In some embodiments, the subject has or is at risk for an oxidative retinal disease. In some embodiments, the subject has or is at risk for retinopathy. In some embodiments, the subject has or is at risk for Stargarts disease, familial macular degeneration, and Liebers Congenital Amurosis. In some embodiments, the amount of the compound administered to the subject is sufficient to prevent, ameliorate, treat, or inhibit the progression of the oxidative disease or retinopathy. In some embodiments, the amount of the compound administered to the subject is sufficient to prevent, ameliorate, treat, or inhibit the progression of the Stargarts disease, familial macular degeneration, and Liebers Congenital Amurosis. In some embodiments, the subject has an oxidative retinal disease or retinopathy associated with expression of a mutant form of an aldehyde dehydrogenase protein. In some embodiments, the subject has an oxidative retinal disease or retinopathy associated with expression of a mutant form of a RDH protein. In some embodiments, the subject has a mutation or deletion in the ALDH gene. In some embodiments, the subject has a mutation or deletion in the RDH gene.

In some embodiments, the subject has or is at risk for Parkinson's Disease and the amount of the compound administered is sufficient to prevent or inhibit the progression of Parkinson's Disease. In some embodiments, the subject has or is at risk for Parkinson's Disease.

In some embodiments, the aldehyde dehydrogenase is aldehyde dehydrogenase-1, aldehyde dehydrogenase-2, aldehyde dehydrogenase-3, aldehyde dehydrogenase-4, or aldehyde dehydrogenase-5. In some embodiments, the aldehyde dehydrogenase is aldehyde dehydrogenase-2.

In some embodiments, the compound or composition described herein is administered orally. In some embodiments, the compound or composition described herein is administered intravenously or intramuscularly.

In some embodiments, the subject has or is at risk for cardiovascular diseases, diabetes, neurodegenerative diseases, stroke, or cancer and the amount of the compound administered is sufficient to prevent or inhibit the progression of cardiovascular diseases, diabetes, neurodegenerative diseases, stroke, and cancer.

Some embodiments relate to a method of treating a subject having a medical condition comprising: identifying the subject having an impaired aldehyde dehydrogenase or retinol dehydrogenase activity; and administering to the subject an effective amount of a compound comprising an isotopically-modified polyunsaturated fatty acid, an isotopically-modified polyunsaturated fatty acid ester, an isotopically-modified fatty acid thioester, an isotopically-modified fatty acid amide, an isotopically-modified fatty acid mimetic, or an isotopically-modified fatty acid pro-drug, the compound having an isotopic modification that reduces oxidation (e.g., lipid oxidation), thereby reducing accumulation of one or more metabolic products associated with the aldehyde dehydrogenase. In some embodiments, the medical condition is a neuropathy or a neurodegenerative disease. In some embodiments, the medical condition is an oxidative retinal disease or retinopathy.

In some embodiments, the medical condition is a retinopathy.

In some embodiments, a subject at risk of or having a neuropathy or neurodegenerative disease may also have an impaired aldehyde dehydrogenase activity. In some embodiments, a subject at risk of or having an oxidative retinal disease or retinopathy may also have an impaired retinol dehydrogenase activity.

Other embodiments relate to a method of treating a subject having a neuropathy or neurodegenerative disease comprising: identifying the subject having an impaired aldehyde dehydrogenase activity; and administering to the subject an effective amount of a compound comprising an isotopically-modified polyunsaturated fatty acid, an isotopically-modified polyunsaturated fatty acid ester, an isotopically-modified fatty acid thioester, an isotopically-modified fatty acid amide, an isotopically-modified fatty acid mimetic, or an isotopically-modified fatty acid pro-drug, the compound having an isotopic modification that reduces oxidation, thereby reducing accumulation of one or more metabolic products associated with the aldehyde dehydrogenase.

Some other embodiments relate to a method of treating a subject having an oxidative eye disease or retinopathy comprising: identifying the subject having an impaired retinol dehydrogenase activity; and administering to the subject an effective amount of a compound comprising an isotopically-modified polyunsaturated fatty acid, an isotopically-modified polyunsaturated fatty acid ester, an isotopically-modified fatty acid thioester, an isotopically-modified fatty acid amide, an isotopically-modified fatty acid mimetic, or an isotopically-modified fatty acid pro-drug, the compound having an isotopic modification that reduces oxidation, thereby reducing accumulation of one or more metabolic products associated with the retinol dehydrogenase.

In some embodiments, the administering is repeatedly administering or ingesting. In some embodiments, the compound described herein is administered orally.

In some embodiments, the amount of the compound administered is sufficient to prevent, ameliorate or inhibit a progression of the neuropathy or neurodegenerative disease. In some embodiments, the neuropathy or neurodegenerative disease is associated with a mutation or deletion in the ALDH gene.

In some embodiments, the amount of the compound administered is sufficient to prevent, ameliorate or inhibit a progression of the oxidative retinal disease or retinopathy. In some embodiments, the oxidative retinal disease or retinopathy is associated with a mutation or deletion in the ALDH gene. In some embodiments, the retinol dehydrogenase is a short chain dehydrogenase such as a 11-cis-retinol dehydrogenase and is preferably enzymatically active. In some embodiments, the retinol dehydrogenases is able to clean up retinol (e.g., 11-cis-retinol) and remove the toxic retinol from the retinal pigment epithelium (RPE). In some embodiments, the retinol dehydrogenases is able to clean up cholesterol and/or membrane lipid and remove them from the retinal pigment epithelium (RPE).

Patient Stratification

In some embodiments, the method includes stratifying the subject for treatment with the compound described herein. Stratification refers to the identification of a group of patients with shared "biological" characteristics by using molecular, genetic, biochemical or imaging diagnostic testing to select the optimal management for the patients and achieve the best possible outcome in terms of (based on the category and disease characteristics). Such stratification may occur prior to initiating a therapy and/or during the therapy.

In some embodiments, the method described herein can include identifying the subject having or is at risk for a neuropathy or neurodegenerative disease. In some embodiments, the method described herein includes assessing the severity of neuropathy or neurodegenerative disease for the subject.

In some embodiments, the method described herein can include identifying the subject having or is at risk for an oxidative retinal disease. In some embodiments, the method described herein includes assessing the severity of the oxidative retinal disease for the subject. In some embodiments, the oxidative retinal disease is Stargarts disease, familial macular degeneration, and Liebers Congenital Amurosis. In some embodiments, the retinopathy or retinal oxidative disease is associated with a mutation or deletion in the retinol dehydrogenase gene. In some embodiments, the retinopathy or retinal oxidative disease is associated with a mutation or deletion in the RDH 11, RDH 12, ALDH1A1, ALDH1A2, ALDH2, or AKR1b1 gene.

In some embodiments, the method described herein can include identifying the subject having or is at risk for Alzheimer disease. In some embodiments, the method described herein can include identifying the subject having or is at risk for cancer. In some embodiments, the method described herein can include identifying the subject having or is at risk for retinopathy or phospholipase deficiency. In some embodiments, the method described herein can include identifying the subject exposed to environmental factors that may cause accumulation of metabolic products (e.g., aldehyde) associated with the aldehyde dehydrogenase.

In some embodiments, the method described herein includes identifying a subject having an impaired ALDN activity. In some embodiments, the method described herein includes determining whether the subject has a ALDH gene mutation or deletion. In some embodiments, the method described herein includes determining whether the subject has ALDH gene mutation or deletion. In some embodiments, the method described herein includes determining whether the subject has ALDH2 gene mutation or deletion.

In some embodiments, a subject having the impaired aldehyde dehydrogenase activity can be identified by genotyping or by observation of symptoms or a phenotype characteristic of impaired aldehyde dehydrogenase activity. In some embodiments, a subject having such impaired aldehyde dehydrogenase activity can be identified by genetic testing. In some embodiments, a subject having impaired aldehyde dehydrogenase activity can be identified by alcohol-induced flushing. In some embodiments the subject can be identified by testing saliva for aldehyde content and ALDH activity. In some embodiments, a subject having impaired aldehyde dehydrogenase activity can be identified by inability to tolerate alcohol or by low alcohol tolerance. In some embodiments, a subject having impaired aldehyde dehydrogenase activity can be identified based on the family history of impaired aldehyde dehydrogenase condition. Some additional selecting criteria include people from the Southeast Asia geographic regions such as China, Japan, and Korea.

The method described herein can include a step of identifying a subject having or at risk of neuropathy or neurodegenerative disease. The identifying step can be achieved by any suitable methods known in the art. In some embodiments, the identifying step includes performing an assay to determine the presence or absence of one or more neurodegenerative disease diagnostic autoatibodies. In some embodiments, the identifying step includes analyzing the subject's genetic markers associated with of neuropathy or neurodegenerative disease. In some embodiments, a subject having or at risk of neuropathy or neurodegenerative disease can be identified based on physiological indicators.

Impaired Aldehyde Dehydrogenase Activity

In some embodiments, the accumulation of aldehyde is associated with an impaired ALDH activity. In some embodiments, an impaired ALDH activity can be genetic or caused by an environmental factor. In some embodiments, the accumulation of toxic compounds can be associated with the development of Alzheimer and/or Parkinson's disease. In some embodiments, the accumulation of toxic compounds due to impaired ALDH activity can be associated with the development of Alzheimer and/or Parkinson's disease.

The compound and method described herein can reduce the risk of neuropathy, neurodegenerative diseases including late-onset Alzheimer's disease and early-onset Alzheimer's disease. In this respect, certain embodiments also directed to a composition of matter, in particular a food composition, dietary or food supplementation, and pharmaceutical composition, respectively, which supports and/or moderates the alcohol degradation process within the human body. The methods and compositions of certain embodiments can address the problem of accumulation of acetaldehyde after rapid alcohol degradation i.e. alcohol metabolism as may occur in most people having impaired aldehyde activity. The methods and compositions of certain embodiments can also address the problem of accumulation of toxic aldehydes after peroxidation (e.g., lipid peroxidation) as may occur in most people having impaired aldehyde activity.

The compound and method described herein can be used to treat or ameliorate a medical condition associated with the accumulation of one or more toxic compounds in a subject. The compound and method described herein can be used to reverse or ameliorate the effect associated with the accumulation of one or more toxic compounds in a subject. In some embodiments, the compound and method described herein can be used to reduce the amount of one or more toxic compounds accumulated in a subject. In some embodiments, the compound and method described herein can be used to reduce the amount of one or more toxic compounds accumulated in a subject that is caused by an impaired ALDH activity. In some embodiments, the compound and method described herein can be used to reduce the amount of one or more toxic compounds accumulated in a subject that is associated with peroxidation in the subject. In some embodiments, toxic compound accumulated in a subject can be aldehyde or products of lipid peroxidation in a subject. In some embodiments, the products of lipid peroxidation can be malondialdehyde (MDA) and/or 4-hydroxynonenal (HNE) and/or 4-hydroxyhexenal (HHE) and/or DOPAL. Examples of toxic compound that can accumulate in a subject can be found in M. C.-Y. Wey, et al., *PloS One*, 2012, 7(2): e31522, which is incorporated by reference in its entirety.

The method described herein can be used to prevent or ameliorate myocardial damage or cardiomyopathy. The method described herein can be used to treat myocardial damage or cardiomyopathy. In some embodiments, the cardiomyopathy is alcoholic cardiomyopathy. Excessive alcohol ingestion in a subject having impaired ALDH function (e.g., ALDH2*2 carrier) can develop exacerbate myocardial damage including disruptions of the myofibrillar architecture associated with reduced myocardial contractility and decreased ejection volumes. Key features of alcoholic cardiomyopathy are cardiac hypertrophy and ventricular dilatation, causing cardiomegaly, congestive heart failure, and even cardiac death. Mitochondrial ALDH2 in the heart can be a key enzyme in cardioprotection.

The method described herein, which increases detoxification of reactive aldehydes, such as 4-HNE, 4-HHE, or DOPAL, can be effective in protecting against, ameliorating, or treating acute ischemia/reperfusion injury, nitroglycerine tolerance, diabetic and alcohol cardiomyopathy and progression of heart failure.

The method described herein can be effective in preventing, reducing the risk, treating, or inhibiting the progression of cancer. The method described herein can be effective in preventing or reducing the risk for esophageal and gastrointestinal cancers. The method described herein can be effective in preventing, treating, or inhibiting the progression of esophageal and gastrointestinal cancers. Individuals with impaired ALDH (e.g. ALDH2) activity are about 6-10 times more likely to develop esophageal cancer when compared to individuals with the fully active ALDH enzyme who drink similar amounts of alcohol. Individuals with the inactive ALDH2 variant who drink the equivalent of 33 or more U.S. standard drinks per week have a 89-fold increased risk of esophageal cancer compared to non-drinkers.

The compound and treatment method described herein can reduce the risk of cardiovascular diseases, diabetes, neurodegenerative diseases, stroke, and cancer.

ALDH2 is best known for its critical role in ethanol metabolism. The ethanol detoxifying pathway in humans occurs mainly in the liver and is carried out by two enzymatic steps. The first step is catalyzed by alcohol dehydrogenase (ADH), and the second step is mainly catalyzed by ALDH2, also known as ADH4, alcohol dehydrogenase 4 (class II). Among the 19 human ALDH isozymes. ALDH2 is the most efficient one for the metabolism of ethanol-derived acetaldehyde; it has the lowest Km (~0.2 µM) towards this substrate (72). This Km is 900-fold lower than that of the abundant cytosolic ALDH, ALDH1, and therefore, in humans, ALDH2 is probably the only ALDH enzyme that contributes significantly to acetaldehyde metabolism (149). Less known is that ALDH2 is also capable of metabolizing numerous other short-chain aliphatic aldehydes, as well as some aromatic and polycyclic aldehydes (148), thus providing an important protective enzymatic function against these toxic agents. In particular, ALDH2 plays a key role in oxidizing endogenous aldehyde products that arise from lipid peroxidation under oxidative stress, such as omega-6-derived 4-hydroxy-2-nonenal (4-HNE) omega-3-derived 4-hydroxy-2-hexenal (4-HHE), and malondialdehyde (MDA) as well as environmental aldehydes, such as acrolein (present, for example, in tobacco smoke and in car exhaust). Impaired ALDH function can also contribute to the development of cardiovascular diseases, diabetes, neurodegenerative diseases, stroke, and cancer.

Ethanol taken into the body is eliminated by its oxidation, mainly in the liver. Ethanol ($CH_3CH_2OH$) is first metabolized to acetaldehyde ($CH_3CHO$) by alcohol dehydrogenase (ADH), and then acetaldehyde ($CH_2CHO$) is further metabolized to acetic acid ($CH_3COOH$) by aldehyde dehydrogenase (ALDH), mainly by liver aldehyde dehydrogenase 2 (ALDH2), also known as ADH4, alcohol dehydrogenase 4 (class II).

$$CH_3CH_2OH + NAD \rightarrow CH_3CHO + NADH + H^+$$

$$CH_3CHO + NAD + H_2O \rightarrow CH_3COOH + NADH + H^+$$

Most of acetaldehyde generated during alcohol metabolism is promptly eliminated by ALDH2, the low Km ALDH. There are polymorphic isoforms of ALDH and class 2 ALDH (ALDH2), which has the lowest affinity constant (Km), is the most important enzyme for acetaldehyde oxidation. A mutant allele, ALDH2*2, has a single point mutation (G→A) in exon 12 of the active ALDH2*1 gene. This mutation results in a substitution of glutamic acid (Glu) at amino acid position 487 by lysine (Lys). ALDH2*2 encodes thus a catalytically inactive subunit and acts in a dominant negative fashion. Individuals with heterozygous ALDH2*1/2*2 genotype should have only 6% activity compared to those with normal homozygous ALDH2*1/2*1 genotype. Distribution of ALDH2*2 allele varies by race: it is prevalent in East Asia but has not been found in Caucasians and Africans, who have the active ALDH2*1 allele. 40-50% of East Asians have the inactive ALDH2*2 allele. The average peaks of blood acetaldehyde concentrations of ALDH2*1/2*2 heterozygotes and ALDH2*2/2*2 homozygotes after drinking of a small amount of ethanol (0.1 g/kg body weight) are five times and IS times, respectively, of that found in ALDH2*1/2*1 homozygotes after drinking of moderate amount of ethanol (0.8 g/kg body weight). The amount of acetaldehyde in saliva is increased in ALDH2*1/2*2 heterozygotes given alcohol, and its level falls when alcohol oxidation of active ALDH2*1/2*1 homozygotes is inhibited by an ALDH inhibitor 4-methylpyrazol. Therefore, acetaldehyde oxidation is strikingly impaired in individuals with ALDH2*2 allele.

ALDH2 deficiency can be associated with an increased risk of neuropathy and of late-onset Alzheimer's disease. Moreover, sensory conduction time is significantly longer in Japanese alcoholic patients with hypoactive ALDH2*2 allele than that in active ALDH2*1/2*1 homozygotes, indicating dysfunction of peripheral neurons of the formers. The experimental neuronal cell system, in which ALDH is genetically inactivated, becomes highly vulnerable to exogenously added aldehyde metabolite, indicating that oxidative stress caused by acetaldehyde considerably damage neuronal cells. These results collectively suggest that oxidative stress induced by acetaldehyde may damage mitochondrial energy production and modify proteins in the neuronal cells, leading to form the deposition of modified proteins. These changes further damage cellular function and finally cause cell death. Therefore, acetaldehyde may closely be involved in the pathogenesis of polyneuropathy and/or neurodegenerative diseases such as late-onset Alzheimer's disease.

The composition and compound described herein accelerate the disappearance of acetaldehyde and other aldehyde compounds produced during lipid oxidation process, such as 4-Hydroxynonenal (HNE), 4-hydroxy-2-hexenal (HHE), malondialdehyde (MDA), acrylic, methylglyoxal, and oxalic.

The composition of matter described herein accelerates the disappearance of alcohol and acetaldehyde after drinking. The composition is active preferably in ALDH2* 1/2*1 homozygote and ALDH2*1/2*2 heterozygote subjects. The composition described herein can effectively reduce the amount of acetaldehyde in the body. Therefore, the composition described herein can be used to diminish the risk of neuropathy, neurodegenerative diseases, e.g. late-onset Alzheimer's disease or early-onset Alzheimer's disease.

The composition described herein can be effective in ameliorating or treating the medical conditions associated with the accumulation of aldehydes. In some embodiments, the accumulation of aldehyde can be caused by an impaired aldehyde dehydrogenase activity. In some embodiments, the accumulation of aldehyde can be caused by a chemical agent inhibiting an aldehyde dehydrogenase activity. In some embodiments, the chemical agent can be an environmental stressor including Benomyl and S-methyl N-butylthiocarbamate sulfoxide. Examples of environmental stressor can be found in Fitzmaurice A G., et al., *Proc Natl Acad Sci USA*. 2013 110:636-41, which is incorporated herein by reference in its entirety.

Co-Administration of Polyunsaturated Lipid and Oxylipin

Some embodiments relate to a composition comprising an isotopically modified polyunsaturated lipid and one or more oxylipins. Some embodiments relate to a composition comprising an isotopically modified polyunsaturated lipid and one or more prostanoids. In some embodiments, the oxylipin is a metabolic product of arachidonic acid after it undergoes a COX enzyme catalyzed reaction.

In some embodiments, the oxylipin can include a compound formed by oxidizing a polyunsaturated fatty acid. In some embodiments, the oxylipin can include an oxygenated metabolite of a polyunsaturated fatty acid. In some embodiments, oxylipins can be enzymatically produced from PUFAs, for example, from C18; C20 PUFA (e.g., eicosanoids); and C22 PUFAs. In some embodiments, the oxylipin can be an eicosanoid. In some embodiments, the oxylipin can be a prostanoid. In some embodiments, the prostanoid is a prostaglandin. In some embodiments, the oxylipin can be a prostaglandin, such as, for example, in renal function decline with age.

Oxylipin can be administered with a maintenance dose of the isotopically modified polyunsaturated lipid. The dosage amount of oxylipin can be in any suitable amount approved for the specific oxylipin compound. The amount of the isotopically modified polyunsaturated lipid that is co-dosed with oxylipin can be in the range of about 0.1% to 40% by weight of the total dietary amount of the polyunsaturated fatty acid. In some embodiments, the amount of the isotopically modified polyunsaturated lipid that is co-dosed with oxylipin can be in the range of about 0.1%-99%, 0.1%-90%, 0.1%-80%, 0.1%-70%, 0.1%-60%, 0.1%-50%, 0.1%-45%, 0.1%-40%, 0.1%-35%, 0.1%-30%, 0.1%-25%, 0.1%-20%, 0.1%-15%, 01%-10%, 0.1%-5%, or 0.1%-2.5% by weight of what the total dietary amount of the polyunsaturated fatty acid is. In some embodiments, the amount of the isotopically modified polyunsaturated lipid that is co-dosed with oxylipin can be greater than 0.01%, 0.05%, 0.1% 0.2%, 0.3%, 0.4%, 0.5%, 0.6%, 0.7%, 0.8%, 0.9%, 1%, 1.5%, 2%, 3%, 4%, 5%, 6%, 7%, 8%, 9%, 10%, 12%, 15%, 17.5%, 20%, 25%, 30%, 35%, 40%, 45%, 50%, 55%, 60%, 65%, or 70% by weight of the total dietary amount of the polyunsaturated fatty acid. In some embodiments, the amount of the isotopically modified polyunsaturated lipid that is co-dosed with oxylipin can be less than 1%, 1.5%, 2%, 3%, 4%, 5%, 6%, 7%, 8%, 9%, 10%, 12%, 15%, 17.5%, 20%, 25%, 30%, 35%, 40%, 45%, 50%, 55%, 60%, 65%, 70%, 75%, 80%, 85%, 90%, 95%, or 99% by weight of the total dietary amount of the polyunsaturated fatty acid.

The amount of oxylipin can vary depending on the subject, the type of isotopically modified polyunsaturated lipid coadministered, and other factors. In some embodiments, the oxylipin amount can be an amount recommended by the physician. In some embodiments, the oxylipin amount can be 5%, 10%, 20%, 30%, 40%, 60%, 70%, 80%, 90%, or 100% of the daily recommended or approved dietary amount for the specific oxylipin. In some embodiments, the oxylipin amount can be 1%, 2.5%, 5%, 10%, 20%, 30%, 40%, 60%, 70%, 80%, 90%, 100%, 150%, 200%, or 300% of the amount of co-administered isotopically modified polyunsaturated lipid. In some embodiments, the oxylipin amount can be greater than about 0.01 µg, 0.05 µg, 0.1 µg, 0.25 µg, 0.5 µg, 1.0 µg, 2 µg, 3 µg, 4 µg, 5 µg, 6 µg, 7 µg, 8 µg, 9 µg, 10 µg, 20 µg, 30 µg, 40 µg, 50 µg, 60 µg, 70 µg, 80 µg, 90 µg, 100 µg, 200 µg, 300 µg, 400 µg, 500

µg, 600 µg, 700 µg, 800 µg, 900 µg, 1 mg, 1.5 mg, 2 mg, 4 mg, 5 mg, 6 mg, 7 mg, 8 mg, 9 mg, 10 mg, 20 mg, 30 mg, 40 mg, 50 mg, 60 mg, 70 mg, 80 mg, 90 mg, 100 mg, 200 mg, 300 mg, 400 mg, 500 mg, 600 mg, 700 mg, 800 mg, 900 mg, or 1 g. In some embodiments, the oxylipin amount can be less than 0.1 µg, 0.25 µg, 0.5 µg, 1.0 µg, 2 µg, 3 µg, 4 µg, 5 µg, 6 µg, µg, 8 µg, 9 µg, 10 µg, 20 µg, 30 µg, 40 µg, 50 µg, 60 µg, 70 pa, 80 µg, 90 µg, 100 µg, 200 µg, 300 µg, 400 µg, 500 µg, 600 µg, 700 µg, 800 µg, 900 µg, 1 mg, 1.5 mg, 2 mg, 4 mg, 5 mg, 6 mg, 7 mg, 8 mg, 9 mg, 10 mg, 20 mg, 30 mg, 40 mg, 50 mg, 60 mg, 70 mg, 80 mg, 90 mg, 100 mg, 200 mg, 300 mg, 400 mg, 500 mg, 600 mg, 700 mg, 800 mg, 900 mg, 1 g, 1.5 g, 2 g, 4 g, 5 g, 6 g, 7 g, 8 g, 9 g, 10 g, 20 g, 30 g, 40 g, 50 g, 60 g, 70 g, 80 g, 90 g, 100 g, 200 g, 300 g, 400 g, or 500 g. In some embodiments, for an oxylipin (e.g., prostaglandin) injection, (e.g., i.v. or muscle injection), the amount of oxylipin can be within the range of 0.1-1000 µg, 0.1-500 µg, 0.1-100 µg, 0.1-80 µg, 0.1-50 µg, 0.1-40 µg, 0.1-30 µg, 0.1-20 µg, 0.5-40 µg, 1-40 µg, 5-40 µg, 10-40 µg, 1-30 µg, 5-30 µg, 10-30 µg, 1-20 µg, 5-20 µg, 100-1000 µg, 100-500 µg, 200-1000 µg, 200-500 µg, or 250-500 µg. In some embodiments, the amount of oxylipin can be about 10-30 µg. In some embodiments, some oxylipin (e.g., lipoxin) can be infused at 100-1000 µg, more specifically 250-500 µg. In some embodiments, 100 mg of cream for topical delivery can contain 100-500 µg of a prostaglandin, or more specifically 200-300 µg. In some embodiments, the oxylipin amount in a tablet form for oral administration can be 1-1000 µg, 1-800 µg, 1-500 µg, 1-250 µg, 50-500 µg, 50-300 µg, 100-500 µg, or 100-300 µg. In some embodiments, the oxylipin amount in a tablet form for oral administration can be 100-300 µg, such as for treating duodenial ulcers. In some embodiments, when the oxylipin is a metabolic product of Omega-3, its amount can be 10-1000 times lower than the metabolic product that is derived from mega-6. In some embodiments, when the oxylipin is a metabolic product of Omega-3, its amount can be 1-1000 times, 10-1000 times, 100-1000 times, 200-1000 times, 500-1000 times, 800-1000 times, 10-500 times, 10-250 times, 10-100 times, or 50-250 times lower than the metabolic product that is derived from omega-6.

The oxylipin dosing can be administered prior to, concurrently with, or after the administration of the isotopically modified polyunsaturated lipid. In some embodiments, the oxylipin is administrated prior to the administration of the isotopically modified polyunsaturated lipid. In some embodiments, the oxylipin is administrated concurrently with the administration of the isotopically modified polyunsaturated lipid. In some embodiments, the oxylipin is administrated after the administration of the isotopically modified polyunsaturated lipid.

In some embodiments, the oxylipin can be co-administered with the isotopically modified polyunsaturated lipid intravenously, such as injection through Hickman or Groshong line. Alternatively, an oxylipin can be inhaled into lungs using a nebulizer. In some embodiments, the delivery method can be a subcutaneous delivery through a catheter. In some embodiments, the delivery method can include a topical cream. In some embodiments, the form of the delivery method can be solutions associated colloids, biopolymer matrices, micelles, powders, emulsions (e.g., conventional emulsions, multiple emulsions, multilayer emulsions), solid lipid particles, filled hydrogel particles, or the like. In some embodiments, the form of the eliveiy method can be produced from food-grade (GRAS) ingredients (e.g., lipids, proteins, polysactharides, surfactants, minerals, or the like) using various processing operations (e.g., mixing, homogenizing, thermal processing, or the like). In some embodiments, the emulsion delivery form can be an excipient emulsion, such as an excipient nanoemulsion. In some embodiments, the form of delivery method can be a lipid-based delivery system. In some embodiments, the form of delivery method can be a colloidal system including vesicles, mixed micelle, and micelles. In some embodiments, the form of the delivery method can be oral dosage forms, including but not limited to solid forms as tablets, capsules, granules and bulk powders.

In some embodiments, the composition comprises an isotopically modified polyunsaturated lipid and the corresponding oxygenated product of the unmodified polyunsaturated lipid. In some embodiments, the composition comprises an isotopically modified n-3 polyunsaturated fatty acid or ester and oxylipin that is an oxygenated metabolic product or derived from unmodified n-3 polyunsaturated fatty acid or ester. In some embodiments, the composition comprises an isotopically modified n-6 polyunsaturated fatty acid or ester and oxylipin that is an oxygenated metabolic product or derived from unmodified n-6 polyunsaturated fatty acid or ester. In some embodiments, the composition comprises an isotopically modified omega-3 polyunsaturated fatty acid or ester and oxylipin that is an oxygenated metabolic product or derived from unmodified omega-3 polyunsaturated fatty acid or ester. In some embodiments, the composition comprises an isotopically modified omega-6 polyunsaturated fatty acid or ester and oxylipin that is an oxygenated metabolic product or derived from unmodified omega-6 polyunsaturated fatty acid or ester.

Some embodiments relate to a method of preventing or ameliorating a side effect of an isotopically modified polyunsaturated lipid in a subject, comprising coadministering the isotopically modified polyunsaturated lipid and a prostanoid to the subject. Some embodiments relate to a method of preventing or ameliorating a side effect of a isotopically modified polyunsaturated lipid in a subject, comprising administering to the subject an effective amount of prostanoid.

Some embodiments relate to a method of reversing, preventing or reducing a disruption to a metabolic pathway involving cyclooxygenase in a subject, comprising administering to the subject an effective amount of prostanoid. Some embodiments relate to a method of reversing, preventing or reducing a disruption to a metabolic pathway involving cyclooxygenase in a subject, comprising coadministering the isotopically modified polyunsaturated lipid and prostanoid to the subject.

Some embodiments relate to a method of reversing, preventing or reducing an inhibition to an enzymatic process involving cyclooxygenase in a subject, comprising administering to the subject an effective amount of prostanoid. Some embodiments relate to a method of reversing, preventing or reducing an inhibition to an enzymatic process involving cyclooxygenase in a subject, comprising coadministering the isotopically modified polyunsaturated lipid and prostanoid to the subject.

Some embodiments relate to a method of enhancing or maintaining a cyclooxygenase activity in a subject, comprising administering to the subject an effective amount of prostanoid. Some embodiments relate to a method of enhancing or maintaining a cyclooxygenase activity in a subject, comprising coadministering the isotopically modified polyunsaturated lipid and prostanoid to the subject.

In some embodiments, the subject is being administered with an isotopically modified polyunsaturated lipid. In some embodiments, the subject has isotopically modified polyunsaturated lipid incorporated into the body.

In some embodiments, the prostanoid is a prostaglandin. In some embodiments, the prostaglandin is prostaglandin $I_2$ ($PGI_2$), prostaglandin $E_2$ ($PGE_2$), or prostaglandin $F_{2\alpha}$ ($PGF_{2\alpha}$). In some embodiments, the prostanoid is a thromboxane. In some embodiments, the prostanoid is a prostacyclin. In some embodiments, the prostanoid is a 5-, 11-, 12- or 15-hydroxyeicosatetraenoic acid (HETEs, DIHETEs). In some embodiments, the prostanoid is a hydroperoxyeicosatetraenoic acid. In some embodiments, the prostanoid is a leukotriene.

In some embodiments, the subject is ingesting more than 0.001 g, 0.005 g, 0.01 g, 0.05 g, 0.1 g, 0.2 g, 0.5 g, 0.6 g, 1 g, 2 g, 3 g, 4 g, 5 g, 6 g, 7 g, 8 g, 9 g, 10 g, 12 g, 15 g, 17.5 g, 20 g, 25 g, 30 g, 35 g, 40 g, 50 g, 60 g, 70 g, of the isotopically modified polyunsaturated lipid. In some embodiments, the subject has been administered with the isotopically modified polyunsaturated lipid for at least one day, 3 days, 1 week, 2 weeks, 3 weeks, 1 month or 2 months.

Reference to "the isotopically modified polyunsaturated lipid" herein should be understood to encompass all isotopically modified compound described herein, including without limitation an isotopically modified polyunsaturated fatty acid, isotopically modified polyunsaturated fatty acid ester, isotopically modified polyunsaturated fatty acid thioester, isotopically modified polyunsaturated fatty acid amide, isotopically modified polyunsaturated fatty acid mimetic, and isotopically modified polyunsaturated fatty acid pro-drug. In some embodiments, the isotopically modified polyunsaturated lipid is an isotopically modified polyunsaturated fatty acid. In some embodiments, the isotopically modified polyunsaturated lipid is an isotopically modified polyunsaturated fatty acid thioester. In some embodiments, the isotopically modified polyunsaturated lipid is an isotopically modified polyunsaturated fatty acid amide. In some embodiments, the isotopically modified polyunsaturated lipid is an isotopically modified polyunsaturated fatty acid mimetic. In some embodiments, the isotopically modified polyunsaturated lipid is an isotopically modified polyunsaturated fatty acid pro-drug. In some embodiments, the isotopically modified polyunsaturated lipid is an arachidonic acid deuterated at one or more positions. In some embodiments, the isotopically modified polyunsaturated lipid is a D6 arachidonic acid. In some embodiments, the isotopically modified polyunsaturated lipid is 13,13-D2 arachidonic acid. In some embodiments, the isotopically modified polyunsaturated lipid is 7, 7-D2 arachidonic acid, 10, 10-D2 arachidonic acid, 7, 10-D2 arachidonic acid, 7, 13-D2 arachidonic acid, 7, 10, 13-D6 arachidonic acid.

Method of Using Magnetic Resonance Imaging

Free radicals, such as superoxide and nitric oxide, have an unpaired electron, making them intrinsically paramagnetic and thus detectable by 1/T1 magnetic resonance imaging (MRI). Some neurons of interest produce free radicals continuously as either part of normal function or during oxidative stress. This steady stream of free radicals likely produces an endogenous, pseudo-constant, and highly localized paramagnetic relaxation mechanism detectable with 1/T1 MRI. To confirm a free radical contribution to the 1/T1 signal, data are collected in the absence and presence of a quenching condition. This quench-assisted. MRI approach are advantageous in that many antioxidants readily cross blood-brain/retina barriers, and are approved by the Food and Drug Administration for safe use in humans.

The efficacy of the isotopically modified polyunsaturated lipid (e.g., deuterated polyunsaturated fatty acid) treatment may be monitored in patients through D-PUFA-induced decrease in neuronal oxidative stress, employing variable magnetic resonance imaging (MRI)-based techniques without contrasting agents. In some embodiments, the technique based on measurement of longitudinal relaxation time (decay constant) T1. In some embodiments, a greater than normal 1/T1 parameter would signal an increased oxidative stress, while the decrease of 1/T1 can indicate the effectiveness of the isotopically modified polyunsaturated lipid in mitigating or reducing the continuously produced paramagnetic free radical levels, which can be measured in vivo using high-resolution (22-micro-m axial resolution) 1/T1 magnetic resonance imaging (MRI) without and with a confirmatory quench (quench-assisted MRI). The quench-assisted MRI has the laminar resolution and detection sensitivity to evaluate normal and pathologic production of free radicals in vivo.

Some embodiments relate to a method, comprising performing a variable magnetic resonance procedure on a patient after receiving a course of isotopically modified polyunsaturated lipid therapy to measure post-treatment neuronal oxidative stress in the patient.

Some embodiments relate to a method of monitoring the change of oxidative stress in a patient, the method comprising performing a variable magnetic resonance procedure on a patient after receiving a course of isotopically modified polyunsaturated lipid therapy to measure post-treatment neuronal oxidative stress in the patient; performing a variable magnetic resonance procedure on the patient prior to the course of D-PUFA therapy to obtain a first measure of neuronal oxidative stress in the patient; and correlating the decrease the decrease in the neuronal oxidative stress with an effectiveness in the therapy.

In some embodiments, the method described herein further includes performing a variable magnetic resonance procedure on the patient prior to the course of D-PUFA therapy to obtain a first measure of neuronal oxidative stress in the patient.

In some embodiments, the method described herein further includes comparing the first measure of neuronal oxidative stress to the post-treatment measurement of oxidative stress to determine the effectiveness of the isotopically modified polyunsaturated lipid therapy.

In some embodiments, the isotopically modified polyunsaturated lipid used in the therapy is an isotopically modified polyunsaturated fatty acid, an isotopically modified polyunsaturated fatty acid ester, an isotopically modified polyunsaturated fatty acid amide, an isotopically modified polyunsaturated fatty acid thioester, or an isotopically modified polyunsaturated fatty acid prodrug.

In some embodiments, the neuronal oxidative stress is determined through measuring a longitudinal relaxation time (decay constant) T1. In some embodiments, an increase in 1/T1 measured through the MRI is correlated with an increase in oxidative stress. In some embodiments, a decrease in 1/T1 is correlated with a decrease in oxidative stress. In some embodiments, the method described herein further includes comparing 1/T1 measured prior to the therapy and 1/T1 measured post therapy to determine a change in oxidative stress. In some embodiments, the method further includes continuing the therapy when a decrease in oxidative stress is detected through the MRI measurement. In some embodiments, the method further includes increasing the amount of the isotopically modified polyunsaturated lipid when an increase or no change in oxidative stress is detected through the MRI measurement.

In some embodiments, the amount of the continuously produced paramagnetic free radical can be measured in vivo using a variable magnetic resonance imaging (MRI) (e,g, 1/T1) without and/or with a confirmatory quench (quench-assisted MRI). In some embodiments, the quench-assisted MRI has the laminar resolution and detection sensitivity sufficient to evaluate normal and pathologic production of free radicals in vivo. In some embodiments, the method described herein further includes using a quench assisted magnetic resonance resolution to determine the amount of free radicals in vivo after the therapy.

In some embodiments, the method described herein comprises performing a variable magnetic resonance procedure on the patient's brain. In some embodiments, the method described herein comprises performing a variable magnetic resonance procedure on the patient's retina. In some embodiments, the method described herein comprises performing a variable magnetic resonance procedure on the patient's eye. In some embodiments, the 1/T1 in the brain section of the patient is measured. In some embodiments, the amount of free radicals from the brain section of the patient are measured. Examples of MRI measurement procedures can be found in Bruce A. Berkowitz; et al., *Investigative Ophthalmology & Visual Science* (December 2015) Vol. 56; No. 13, pp. 7931-38 and Bruce A. Berkowitz; et al., *Investigative Ophthalmology & Visual Science* (February 2016), Vol. 57, No. 2, pp. 577-85, which are incorporated for this purpose in their entireties.

Experimental studies show that antioxidant strategies protect neurons in AD models, but almost all clinical trials with antioxidants for the treatment or prevention of AD have been consistently negative. The importance of oxidative stress and LPO in the pathogenesis of AD, or the clinical potential of D-PUFA treatment is important. Studies claiming the ineffectiveness of antioxidant interventions suffer from variations in treatment regimens and trial duration, lack of therapeutic drug monitoring, lack of monitoring oxidative stress reduction caused by drug treatment, and choice and dosage of antioxidant. For example, under some conditions the lipophilic chain-terminating antioxidant, Vitamin E, can also act as a pro-oxidant, thus serving to increase LPO. Also the relative importance of enzymatic versus nonenzymatic, as well as two-electron versus one-electron processes in LPO should also be considered. Specific inhibition of nonenzymatic LPO by D-PUFAs may prove beneficial in a number of disease states involving LPO-induced damage, and that this mechanism for LPO reduction is likely superior to general antioxidant inhibition or enzymatic inhibition of LPO. DPUFAs are not antioxidants per se: they do not quench ROS nor do they affect cellular redox status or the antioxidant-ROS ratio, thus allowing normal ROS-mediated signaling pathways to remain intact. The relevance and importance of ALDH2 to antioxidant defense is suggested by a number of studies in which inhibition or lack of ALDH2 increases the vulnerability to HNE- and reactive aldehyde-induced datnag, whereas increased expression or activation of ALDH2 confers protective effects.

ALDH2 is expressed in numerous brain regions and its expression/activity is increased in the temporal cortex and putamen in AD brains and also in the putamen in PD brains, suggesting a protective response to AD- and PD-associated increases in LPO. In addition, some epidemiological studies have reported an increased risk for AD in individuals possessing the Glu504Lys loss of function mutation of ALDH2. The Glu504Lys ALDH2 polymorphism is also associated with an increased incidence of certain cancers, with an increased risk for developing schizophrenia, and for developing PD in some studies but not others. Increased striatal concentrations of the toxic dopamine metabolite, 3,4-dihydroxyphenylacetaldehyde are seen in Aldh1A1/Aldh2 double knockout mice. These mice exhibit age-related impairments in motor performance, and have been suggested as an animal model of PD, which is also associated with increased LPO and HNE protein adduct formation.

The development of Aldh2−/− mice as an alternative and complementary model to the numerous transgenic mouse models of AD that are dependent on overexpression of mutant human genes linked to early onset familial AD. The NMZ (4-methyl-5-(2-(nitrooxy)ethyl)thiazol-3-ium chloride), a neuroprotective agent that targets synaptic failure by a combination of 4-aminobutyrate-mitnetic activity and increased NO/cGMP/CREB signaling, memory can be improved in Aldh2−/− mice as well as in APP/PS1 and 3×Tg transgenic mice. The Aldh2−/− mice are characterized by age-related decreases in the performance of several hippocampus-dependent memory tasks, together with a number of AD-like pathological changes, including increases in amyloid b (Ab), phosphorylated tau protein, defective CREB signaling, synaptic loss, and several vascular pathologies.

The changes in the behavioral responses as an index of efficacy of the D-PUFA-enriched diet can be used. The improved cognitive performance exhibited by DPUFAs can also be monitored using quench-assisted MRI which demonstrated increased free radical production (and by extension increased LPO) in the dorsal CA1 region of the hippocampus of Aldh2−/− mice relative to wild-type mice. In rodents, this hippocampal subfield is associated with the encoding of spatial memory (which can be assessed by behavioral tests such as the MVM task), and is therefore consistent with the idea of a role for LPO in the impaired spatial reference memory exhibited by Aldh2−/− mice, and further, its amelioration by D-PUFA treatment.

EXAMPLES

Example 1

Pharmaceutical or nutritional formulations containing isotopically modified compound such as an isotopically-modified polyunsaturated fatty acid, an isotopically-modified polyunsaturated fatty acid ester, an isotopically-modified fatty acid thioester, an isotopically-modified fatty acid amide, an isotopically-modified fatty acid mimetic, or an isotopically-modified fatty acid pro-drug are prepared. Additional components such as isotopically unmodified polyunsaturated fatty acid, fatty acid ester, fatty acid thioester, fatty acid amide, fatty acid mimetic, and/or fatty acid pro-drug can be added to the composition.

Adult volunteers (both male and female volunteers, age 26-48) having impaired ALDH activity and normal ALDH function are selected and are given a dose of alcoholic beverage. The ALDH function of each volunteer is determined by genotyping. The genotype of the ALDH2 gene is determined by the mismatched PCR-RFLP method reported previously in Takeshita, T., et al, (1994) *Hum. Genet.* 94, 217-223 with minor modifications. In brief, 5 ng of DNA is amplified in 15 ml of PCR mixture with the following primers: sense primer: 59-TTACAGGGTCAACTGCTATG-39, and antisense primer: 59-CCACACTCACAG-FIITCTCTT-39, for the amplification of a 131 bp DNA fragment including exon 12 of the ALDH2 gene. The PCR product is digested with 1.5 unit of Earl in 100 mg/ml bovine serum albumin and the reaction buffer provided by the manufacturer (New England Biolab, Beverly, Mass.). Digested DNA is separated by 2.5% agarose electrophoresis, where the common ALDH2*1 allele show 108 and 23 bp, and the mutant ALDH2*2 allele 131 bp. Samples showing undigested patterns are repeatedly genotyped by the digestion using 2 units of Earl to verify the genotypes. Volunteers with mutant ALDH gene are divided into two groups, with one group (treatment group) being administered with compositions containing isotopically modified compound such as D2-LA, D4-ALA, or 1:1 combinations of both D2-LA and D4-ALA; and another group (positive control group) being administer with compositions containing isotopically unmodified compound such as LA, ALA, and 1:1 combinations of both LA and ALA. Volunteers with wild-type ALDH gene are assigned to the negative group.

Volunteers in all three groups are provided with four hundred ml of red wine which contains 12.5% of ethanol is used as alcohol, and this amount is exactly same as 50 gram of ethanol. Red wine is administered during the first interval of 30 minute from the start of experiments.

For all three groups of volunteers, blood samples are taken at the following times: before the alcohol administration (0), and 30 min, 60 min, 90 min, 6 h, 12 h, and 24 h after alcohol administration. Compositions containing isotopically modified compound are administered. For the ethanol measurement, whole blood is stored at 4° C. in heparin coated tube. For the acetaldehyde measurement, blood samples are immediately centrifuged by heparin coated tube at 1500 rpm×10 minutes, and serum are frozen at −50° C. Ethanol and acetaldehyde are measured, and statistical analysis of the results is conducted by r test. The treatment group shows low blood acetaldehyde level in comparison to the positive control group and comparable level of blood aldehyde with the negative control group at the time points 30 min, 60 min, 90 min, 6 h, 12 h, and 24 h after administration of the alcohol.

Example 2

Pharmaceutical or nutritional formulations containing isotopically modified compound such as an isotopically-modified polyunsaturated fatty acid, an isotopically-modified polyunsaturated fatty acid ester, an isotopically-modified fatty acid thioester, an isotopically-modified fatty acid amide, an isotopically-modified fatty acid mimetic, or an isotopically-modified fatty acid pro-drug are prepared. Additional components such as isotopically unmodified polyunsaturated fatty acid, fatty acid ester, fatty acid thioester, fatty acid amide, fatty acid mimetic, and/or fatty acid pro-drug can be added to the composition.

Adult volunteers (both male and female volunteers, age 26-48) having impaired ALDH activity and normal ALDH function are selected. The ALDH function of each volunteer is determined by genotyping. The genotype of the ALDH2 gene is determined by the mismatched PCR-RFLP method reported previously in Takeshita, T., et al, (1994) Hum. Genet. 94, 217-223 with minor modifications. In brief, 5 ng of DNA is amplified in 15 ml of PCR mixture with the following primers: sense primer: 59-TTACAGGGT-CAACTGCTATG-39, and antisense primer: 59-CCACACT-CACAGTTTCTCTT-39, for the amplification of a 131 bp DNA fragment including exon 12 of the ALDH2 gene. The PCR product is digested with 1.5 unit of Earl in 100 mg/ml bovine serum albumin and the reaction buffer provided by the manufacturer (New England Biolab, Beverly, Mass.). Digested DNA is separated by 2.5% agarose electrophoresis, where the common ALDH2*1 allele show 108 and 23 bp, and the mutant ALDH2*2 allele 131 bp. Samples showing undigested patterns are repeatedly genotyped by the digestion using 2 units of Earl to verify the genotypes. Volunteers with mutant ALDH gene are divided into two groups, with one group (treatment group) being administered compositions containing isotopically modified compound such as D2-LA, D4-ALA, or 1:1 combinations of both D2-LA and D4-ALA; and another group (positive control group) being administered compositions containing isotopically unmodified compound such as LA, ALA, and 1:1 combinations of both LA and ALA. In each case, 10 compound is administered each day for one month prior to alcohol administration. Volunteers with wild-type ALDH gene are assigned to the negative group.

For all three groups of volunteers, blood samples are taken at the following times after administration of the alcohol: (0) min, and 30 min, 60 min, 90 min, 6 h, 12 h, and 24 h after administration. For the measurement of aldehyde compounds, blood samples are immediately centrifuged by heparin coated tube at 1500 rpm×10 minutes, and serum are frozen at −50° C. Aldehyde compounds such as HNE, HHE, MDA, acrylic acid, methylglyoxal, oxalic acid are measured, and statistical analysis of the results is conducted by r test. The treatment group shows low blood aldehyde compound levels in comparison to the positive control group and a level of blood aldehyde comparable with the negative control group at the time points 30 min, 60 min, 90 min, 6 h, 12 h, and 24 h.

Example 3

Many manifestations of defects in alcohol metabolism, alcohol-induced pathology, and hypersensitivity to acetaldehyde observed in the ALDH2*2 East Asians can be reproduced in the ALDH2 knockout (denoted ALDH2$^{-/-}$) mouse model. Pronounced susceptibility to ischemia-reperfusion injuries and accumulation of aldehydic adducts are also demonstrated in the ALDH2$^{-/-}$ mice. Two independent ALDH2 knockout alleles, tagged with a neomycin-resistant marker within the ALDH2 gene, were introduced to the C57BL/6 mouse genome to disrupt the gene function. Western blot analyses confirmed that no immunoreactive ALDH2 protein was produced in the homozygous ALDH2$^{-/-}$ mice. ALDH2 knockout mice provided useful research tools to explore the physiology, phenotypes, and pathologies derived from a complete lack of ALDH2 function. However, these mice may not completely reflect the phenotype of the human ALDH2*2 population, since the ALDH2*2 allele in human carries residual enzyme activity. It is conceivable that subtle biological differences may exist between the genotypes of ALDH2−/−, ALDH2+/−, and ALDH2*1/*2, which represents the largest affected human population. A comprehensive review on the ALDH2 knockout mouse has been published recently by Yu et al. (Yu H S, et al., Characteristics of aldehyde dehydrogenase 2 (Aldh2) knockout mice. Toxicol Mech Methods 19: 535-540, 2009).

10 weeks old ALDH2 knockout mice and the wild-type mice are used for determining the efficacy of the compounds or compositions disclosed herein. The ALDH knockout mice and wild-type mice are divided into an active treatment group (ALDH knockout mice with administration of isotopically modified components), a positive control (ALDH knockout mice with administration of isotopically unmodified components), and a negative group (wild-type mice with administration of isotopically unmodified components), each group composed of eight animals. All groups receive a nonlethal dose of 20% ethanol solution comprising 0.1% of body weight, which is administered via intraperitoneal injection. After administration of ethanol, ethanol levels are collected at three time points: Point 0 at 30 minutes following ethanol administration, Point 1 at 1 hour following ethanol administration, and Point 3 at 2 hours following ethanol administration. The treatment group also receives compositions containing isotopically modified compound such as deuterated polyunsaturated fatty acid (0.01, 0.1, 1.0, 10.0, and 100 mg/kg D2-LA, D4-ALA, and 1:1 combinations of both D2-LA and D4-ALA). The control groups receive at the same time points undeuterated polyunsaturated lipid (0.01, 0.1, 1.0, 10.0, and 100 mg/kg LA, ALA, and 1:1 combinations of both LA and ALA). Prior to administration of the isotopically modified or unmodified compositions, there is not a statistically significant difference observed between the control and treatments groups. 30 minutes or 1 hour after administration of the isotopically modified composition (or 1 h after the administration of ethanol) the blood ethanol levels and acetaldehyde levels are measured. The results show a significant decrease of aldehyde levels in the treatment group when compared with the positive control group. The results also show a comparable aldehyde levels in the treatment group when compared with the positive control group.

Example 4

ALDH2 knockout mice and the wild-type mice were used for determining the efficacy of the compounds or compositions disclosed herein. The treatment group received daily doses of isotopically modified compound such as deuterated polyunsaturated fatty acid. The diet given to the mice was based on a composition containing 10% fat of which 65% was saturated fats (Coconut Oil 101 (Hydrogenated); 25% was ethyl oleate (monounsaturated); and the remaining 10% was either a 1:1 (i.e. 5% each) mixture of normal, hydrogenated linoleic and linolenic acid ethyl esters (the control diet), or a 1:1 (i.e. 5% each) mixture of 11,11-D2-Lin and 11,11,14,14-D4-Lnn ethyl esters (the D-diet).

Morris Water Maze experiments were performed on 6 months old wild type or Aldh2$^{-/-}$ mice on normal diet. (A) Escape latency (time to reach hidden platform) was determined in a 3 day cued trial block (4 trials/day) followed by a 5 day hidden trial block (6 trials/day). Day 9 was a probe trial: the time spent in the target quadrant (B) and number of platform crosses (C) were determined (total time: 60 s). The results indicated that between the wild type group and the Aldh2$^{-/-}$ group, the wild type group mice showed better latency to find platforms, used less time in the target quadrant, and made fewer number of platform crosses in the water mazes. The Aldh2$^{-/-}$ mice group showed memory decline when compared to the wild type group. Details of the Morris Water Maze test results of the wild type group and the Aldh2$^{-/-}$ group can be found in D'Souza et al. *Molecular Brain* (2015) 8:27, which is incorporated by reference for this purpose in its entirety.

D-PUFA supplementation dramatically mitigates this memory decline. Aldh2$^{-/-}$ mice, started on a D-PUFA or H-PUFA diet at 2 months and the Morris water maze test was performed after 2 or 10 weeks. FIG. 1A shows the latency to find platforms for the Aldh2$^{-/-}$ mice in the group being fed with D-PUFA and in the group being fed with H-PUFA; FIG. 1B shows the time in the target quadrant for the Aldh2$^{-/-}$ mice in the group being fed with D-PUFA and in the group being fed with H-PUFA; and FIG. 1C shows the number of crosses made by the Aldh2$^{-/-}$ mice in the group being fed with D-PUFA and in the group being fed with H-PUFA. The progressive impairment of performance in the H-PUFA cohort was observed and the marked improvement of performance in the D-PUFA was also noted.

Example 5

The Novel Object Recognition (NOR) task was performed on 6 months old wild type or Aldh2$^{-/-}$ male/female mice once a month from the third month. Time spent with each object was determined and the ratio of time spent with the novel object relative to the familiar object (upper) and discrimination index (DI, time difference exploring the novel and familiar object, divided by the total time spent exploring both) (lower) was calculated. At DI=0 mice cannot remember if an object is novel or familiar. (WT n=18, Aldh2$^{-/-}$ n=17), analyzed by 2-way ANOVA. For the mice in the wild group fed with normal diet and the Aldh2$^{-/-}$ group fed normal diet, the wild type group showed higher ratio of novel to familiar objects recognized by the mice; and also a higher the discrimination index. Overall, the ALDH knock out mice showed poor novel/old object recognition when compared with the wild type mice. Details of the novel object recognition and discrimination index of the wild type group and the Aldh2$^{-/-}$ group can be found in D'Souza et al. *Molecular Brain* (2015) 8:27, which is incorporated by reference for this purpose in its entirety.

Figure 2:
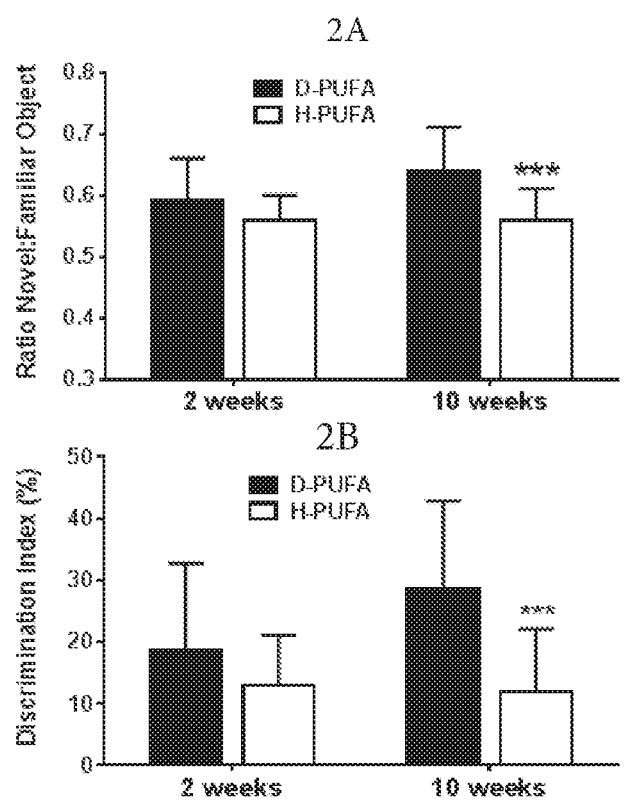
FIG. 2A shows the ratio of novel to familiar objects recognized by the Aldh2$^{-/-}$ mice in the group being fed with D-PUFA and in the group being fed with H-PUFA.
FIG. 2B shows the discrimination index of the Aldh2$^{-/-}$ mice in the group being fed with D-PUFA and in the group being fed with H-PUFA.

D-PUFA supplementation dramatically increased the difference in novel/old object recognition. Aldh2$^{-/-}$ mice, started on a D-PUFA (e.g., D2-LA, D4-ALA, or 1:1 combinations of both D2-LA and D4-ALA) or H-PUFA diet at 2 months performed NOR task after 2 or 10 weeks. The results are shown in FIG. 2. FIG. 2A shows the ratio of novel to familiar objects recognized by the Aldh2$^{-/-}$ mice in the group being fed with D-PUFA and in the group being fed with H-PUFA; and FIG. 2B shows the discrimination index of the Aldh2$^{-/-}$ mice in the group being fed with D-PUFA and in the group being fed with H-PUFA. In FIG. 2, the mice fed with nonmodified diet (e.g., H-PUFA) showed poor novel/old object recognition when compared with the mice fed with the isotopically modified diet (e.g., D-PUFA). An improved performance of the mice fed the D-PUFA diet was noted relative to mice fed the H-PUFA diet. (D-PUFA n=16, H-PUFA n=16). (analyzed by unpaired t-test).

Example 6

Figure 3:
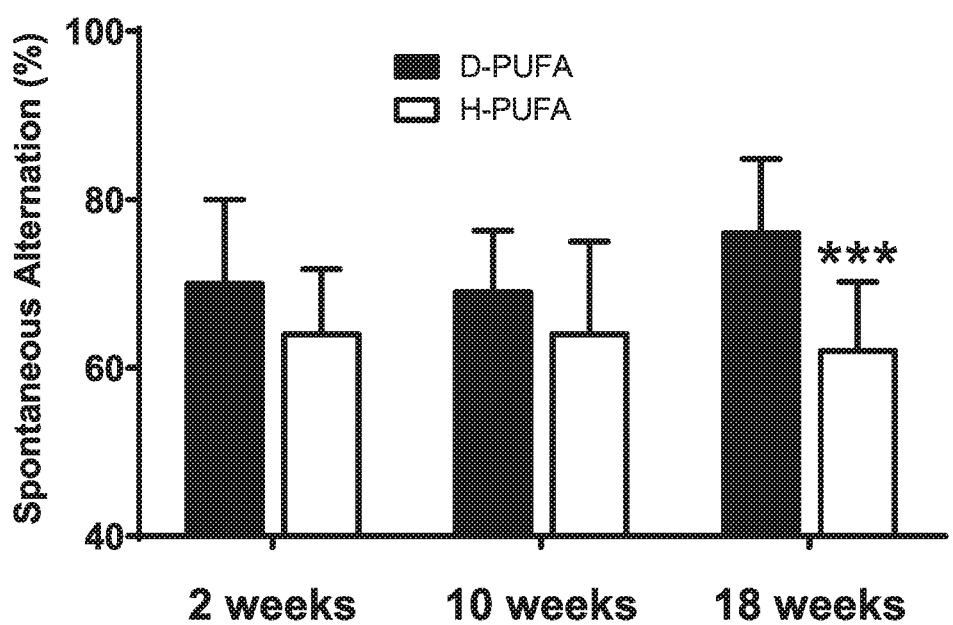
FIG. 3 shows the spontaneous alternation rate in the Y-maze task between the group being fed with isotopically fed with D-PUFA and the group being fed with H-PUFA.

The Y-maze task in 6 month old wildtype or Aldh2$^{-/-}$ mice was performed to test the age-dependent, progressive decline of the mice. Male and female mice were subjected to the Y-maze task and the spontaneous alternation rate was determined. Data were presented as the mean±S.D. (wild type n=18, Aldh2$^{-/-}$ n=17) and were analyzed by a two-way ANOVA, 4D: Aldh2 null mice were started on a D-PUFA D2-LA, D4-ALA, or 1:1 combinations of both D2-LA and D4-ALA) or H-PUFA diet at 2 months of age and the Y-maze task performed after 2, 10 and 18 weeks. For the mice in the wild group fed with normal diet and the Aldh2$^{-/-}$ group fed normal diet, Aldh2$^{-/-}$ mice showed a progressive decrease in performance in both memory tasks compared to their wildtype littermates. Details of the Y-maze test of the wild type group and the Aldh2$^{-/-}$ group can be found in D'Souza et al. *Molecular Brain* (2015) 8:27, which is incorporated by reference for this purpose in its entirety, FIG. 3 shows the results of the groups of Aldh2$^{-/-}$ mice fed with D-PUFA and fed with normal diet after 18 weeks. The results showed the improved performance of the mice fed the D-PUFA diet relative to mice fed the H-PUFA diet. (D-PUFA n=16, H-PUFA n=16). Data analyzed by unpaired t-test.

Example 7

Figure 4A:
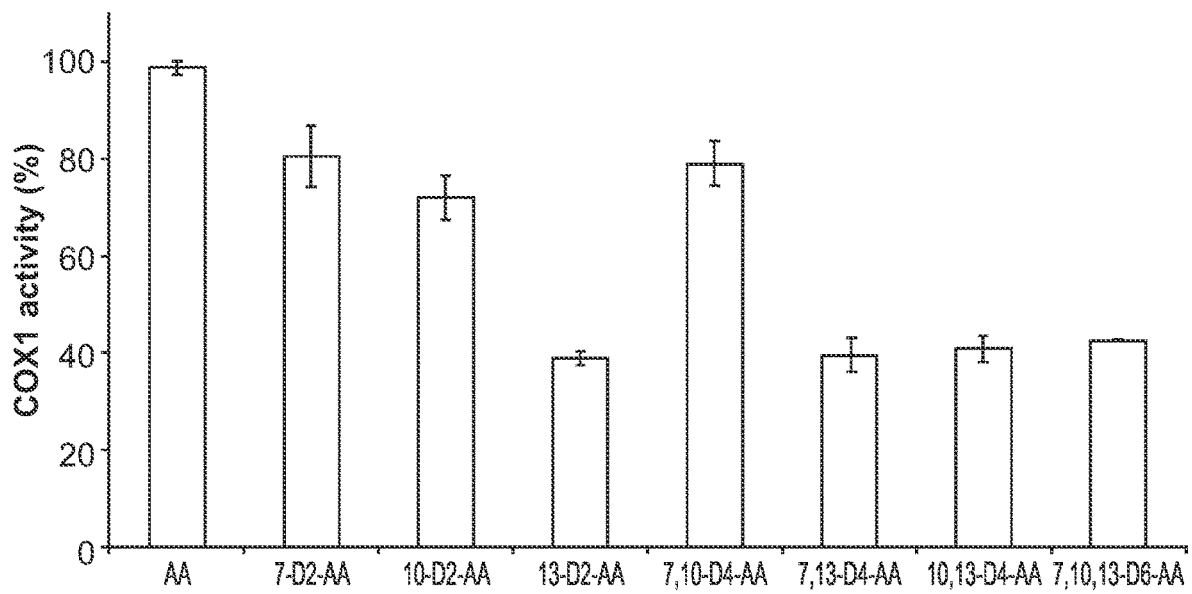
FIG. 4A shows the changes in COX1 enzyme activity when various deuterated arachidonic acids were added to the cells.
Figure 4B:
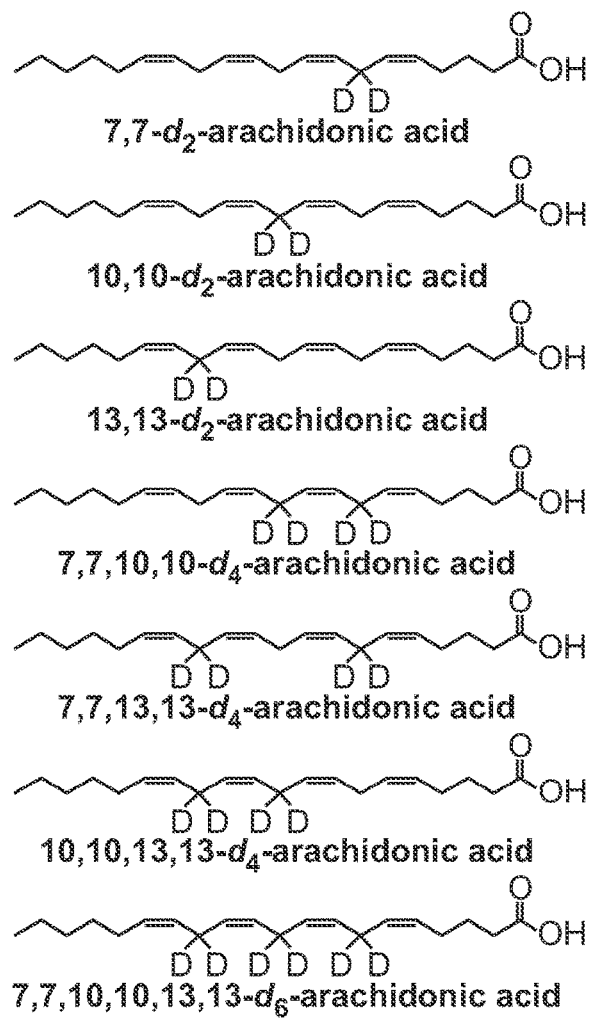
FIG. 4B shows the structure of the deuterated arachidonic acids being tested.

The effect of a high level of isotopically modified polyunsaturated lipid (e.g. arachidonic acids having deuterium at bis-allylic sites) on the enzymatic activity of cyclooxygenase (COX) was examined in vitro. The COX1 activity was measured by oxygen consumption (Clark electrode) in vitro. FIG. 4A shows the changes in COX1 enzyme activity when various deuterated arachidonic acids were added to the cells. FIG. 4B shows the structure of the deuterated arachidonic acids being tested. Arachidonic acid with no deuterium modification was used as a control. As shown in FIG. 4, the 13,13-D2-arachidonic acid was the most effective in reducing the activity of COX1 when compared with other types of deuterated arachidonic acid.

Example 8

Genetic and toxin (e,g, alcohol) induced animal model of Parkinson's Disease is used to study the effect of D-PUFA. Altered gait pattern, which is a shortened stride length and is symptomatic of PD, is studied in the group fed with H-PUFA. The progressive age-related impairment in rotarod performance in the animal models is studied. The effect of age and genotype on striatal dopamine and metabolites in the treatment group and control group are also measured. The results indicate that D-PUFA can be effective in improving, treating, and ameliorating the disease patterns when compared with the group fed with H-PUFA.

Example 9

An animal model is administered with the isotopically modified polyunsaturated lipid (e.g. arachidonic acids having deuterium at bis-allylic sites) and its corresponding metabolic product involved in the COX enzyme activity (e.g., prostaglandin with no isotopic modification) is monitored. One control group is fed with just isotopically modified polyunsaturated lipid, and another control group is fed with just non-modified polyunsaturated lipid. The results indicate that the co-administration of isotopically modified polyunsaturated lipid and its corresponding COX enzyme metabolic product can be effective in reversing, preventing or reducing a disruption to a metabolic pathway involving cyclooxygenase e.g. COX1) caused by isotopically modified polyunsaturated lipid.

Example 10

MRI is used to measure the change of oxidative stress in the animal model's retina prior to and after the isotopically modified polyunsaturated lipid therapy. In all groups, immediately before the MRI experiment, animals are anesthetized with urethane. Adults are treated topically with 1% atropine to ensure dilation of the iris during light exposure followed by 3.5% lidocaine gel to reduce sensation that might trigger eye motion, and to keep the ocular surface moist. High resolution 1/T1 data (details below) are acquired on a 7 T system (ClinScan; Bruker Corporation, Billerica, Mass., USA) using a receive-only surface coil (1.0 cm diameter) centered on the left eye. Each 1/T1 data set takes 15 minutes to collect. 1/T1 data were collected first in the dark and then at 13 minutes and 29 minutes (midpoint of acquisition) after turning on the light. Retinal partial saturation T1 data are acquired using a dual coil mode on a 7 T Bruker ClinScan system: Several single spin-echo (time to echo [TE] 13 ms, 7 37 mm2, matrix size 1603320, slice thickness 600 lm, in-plane resolution 21.9 lm) images are acquired. In other words, to compensate for reduced signal to noise ratios at shorter TRs, progressively more images are collected as the TR is decreased. During an MRI session, animals are studied in an alternating order between controls and experimental mice.

In each adult animal, the ocular dilation is based on the iris position on the MRI data. 1/T1 MRI data from the central retinal (61 mm from the center of the optic nerve) are analyzed. Single images are acquired with the same TR are first registered (rigid body) and then averaged. These averaged images are then coregistered across TRs. The central retinal regions-of-interest are analyzed by calculating 1/T1 maps by fitting to a three-parameter T1 equation (y ¼ a p b*(exp(_c *TR)), where a, b, and c are fitted parameters) on a pixel-by-pixel basis. The reciprocal (1/T1) values directly reflect paramagnetic free radical levels. Central intraretinal 1/T1 profiles are obtained as detailed elsewhere. Transretinal profiles from the superior and inferior retina are averaged.

A 22-μm axial resolution MRI that allows measurement of several rod cell compartment-specific functions in vivo with anatomical confirmation provided by coregistration with optical coherence tomography (OCT) images is obtained. Quench-assisted MRI is tested in two established oxidative stress based retinopathy models using a combination of clinically relevant antioxidants that operate with different quenching mechanisms: methylene blue (MB, an alternate electron transporter that effectively inhibits superoxide generation by mitochondria) and a-lipoic acid (LPA, a potent free radical scavenger). To evaluate measurement sensitivity, healthy photoreceptors and RPE are studied as well. One location measured is approximately 75% of the mitochondria in the retina, and another location is measured is in the brain. The quench condition in this portion of the study is light. In the light, rod cell ion channels close, thus negating the demand for as much ATP, and leading to a substantial reduction in free radical production compared with that in the dark. In contrast to rods, cone cells do not saturate with light, and are expected to continue to generate high levels of free radicals in the light.

The change of oxidative stress in the animal model's brain prior to and post therapy can also be measured using the above procedures. The test results can demonstrate the efficacy of isotopically modified polyunsaturated lipid therapy in reducing oxidative stress in the retina.

Example 11

Genetic and toxin (e,g, alcohol or other environmental stressor) induced animal model of oxidative retinal disease such as Stargarts disease, familial macular degeneration, and Liebers Congenital Amurosis is used to study the effect of D-PUFA. The generation and phenotypic characterization of mice with a null mutation or deletion in retinol dehydrogenase gene (e.g., RDH 11, RDH 12, ALDH1A1, ALDH1A2, ALDH2, and AKR1b1) is carried out, and these mice can be used for in vivo screening of D-PUFA effects on oxidative retinal diseases associated with retinol dehydrogenase mutation or deletion. The levels of cholesterol, membrane lipid, and/or retinol accumulation in the eye are measured and correlated with the change of the disease severity. The results indicate that D-PUFA can be used to treat, ameliorate, or improve the disease patterns when compared with the group fed with H-PUFA.

Example 12

The incorporation of D-PUFAs into tissues was studied. Aldh2$^{-/-}$ mice were treated with diets containing either deuterium-reinforced D-PUFAs or control H-PUFAs (see Table 1 for composition of the diets). At the end of the study, 18 weeks after Western-type diet feeding, efficient D-PUFA incorporation was confirmed by measuring deuterium content in brain sections of the mice. The difference between the D-PUFA (33 342±3223‰) and the H-PUFA (−140.7±12.5‰; P<0.001) groups corresponds to an approximate 35% D-PUFA incorporation (i.e., D-PUFA fraction of total PUFA). This level of D-PUFA substitution was biologically relevant as approximately 10-20% was sufficient to terminate LPO.

TABLE 2

Composition of H- and D-PUFA-containing diets. AIN-93M rodent-based diets were modified to contain 12% fat with 1.2% Dlinoleic:D-linolenic (1:1 weight ratio), or 1.2% H-linoleic:Hlinolenic (1:1 weight ratio). gm %, grams of each component per 100 grams of diet.

|  | H-diet | | D-diet | |
| --- | --- | --- | --- | --- |
|  | gm % | kcal % | gm % | kcal % |
| D-Linoleic acid, ethyl ester | — | — | 0.6 | 1.2 |
| D-Linolenic acid, ethyl ester | — | — | 0.6 | 1.2 |
| H-Linoleic acid, ethyl ester | 0.6 | 1.2 | — | — |
| H-Linolenic acid, ethyl ester | 0.6 | 1.2 | — | — |
| Oleate, ethyl | 2.9 | 6.2 | 2.9 | 6.2 |
| Coconut oil, 101 (hydrogenated) | 7.5 | 16.0 | 7.5 | 16.0 |
| Casein | 13.5 | 12.8 | 13.5 | 12.8 |
| L-cystine | 0.0 | 0.2 | 0.0 | 0.2 |
| Corn starch | 43.2 | 40.9 | 43.2 | 40.9 |
| Maltodextrin 10 | 12.1 | 11.4 | 12.1 | 11.4 |
| Sucrose | 9.7 | 9.1 | 9.7 | 9.1 |
| Cellulose | 4.8 | 0.0 | 4.8 | 0.0 |
| t-Butylhydroquinone | 0.0 | 0.0 | 0.0 | 0.0 |
| Mineral Mix S10022M | 3.4 | 0.0 | 3.4 | 0.0 |
| Vitamin Mix V10037 | 1.0 | 0.9 | 1.0 | 0.9 |
| Chlorine bitartrate | 0.2 | 0.0 | 0.2 | 0.0 |

Example 13

Figure 5:
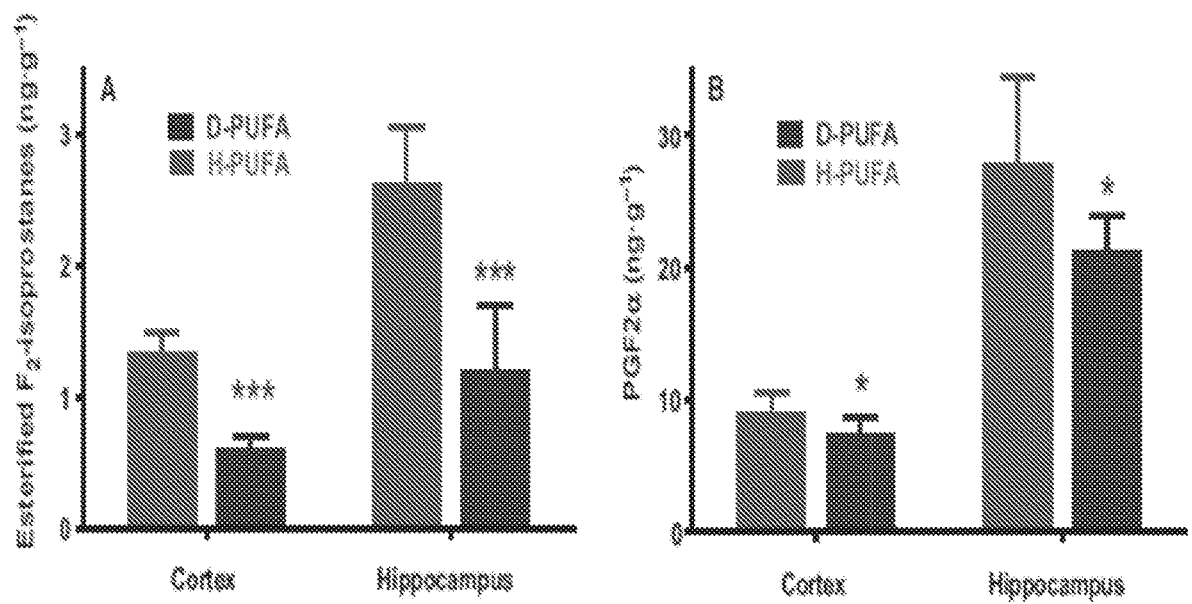
FIG. 5 shows decrease in F2-IsoPs (Panel A) and PGF2a (Panel B) in cortex and hippocampus from Aldh2$^{-/-}$ mice fed the D-PUFA diet.

The effect of D-PUFAs reducing lipid peroxidation products was studied. Since oxidative stress was considered an important factor in the development of AD, and since D-PUFAs have been shown to reduce LPO products in other models, whether D-PUFA treatment also reduces LPO was also studied in the Aldh2$^{-/-}$ mouse model of sporadic AD. D-PUFA treatment markedly decreased esterified F2-IsoPs by approximately 55% in both cortex and hippocampus, and prostaglandin F2a (PGF2a) levels by 20-25% (FIG. 5), indicating that DPUFAs effectively reduce brain LPO products in Aldh2$^{-/-}$ mice. FIG. 5 shows decrease in F2-IsoPs (Panel A) and PGF2a (Panel B) in cortex and hippocampus from Aldh2$^{-/-}$ mice fed the D-PUFA diet. Eighteen weeks after initiation of either the D-PUFA or H-PUFA diet, homogenates of cortex or hippocampus were analyzed for bound F2-IsoPs or PGF2a. Data are presented as means±SD (n=6-8) and were analyzed by Student's t-test for unpaired data.

Example 14

Figure 6:
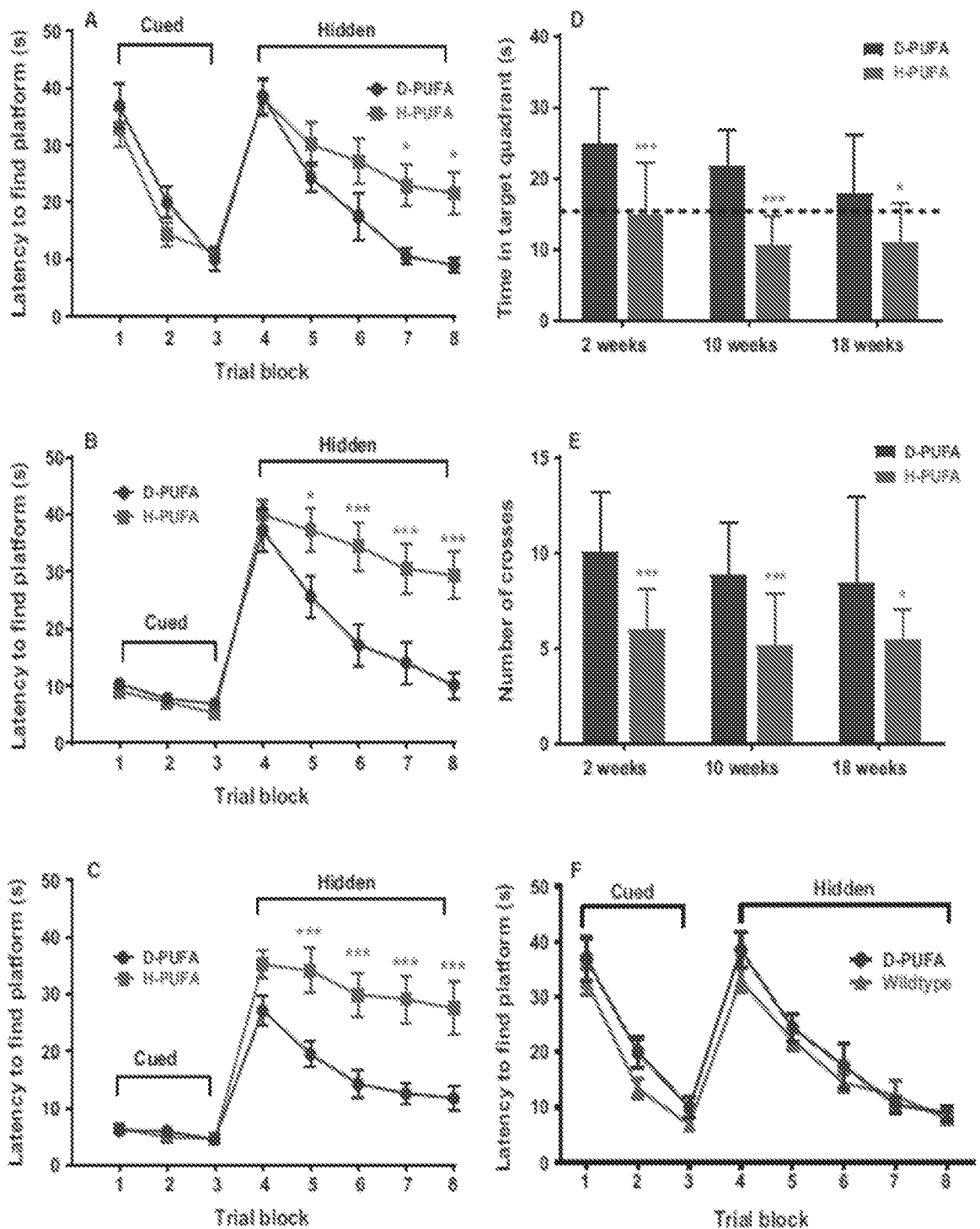
FIG. 6A-6F show the superior performance in the Morris Water Maze task in Aldh2$^{-/-}$ mice fed the D-PUFA diet. Two weeks (A) 10 weeks (B), or 18 weeks (C) after the initiation of the D-PUFA or H-PUFA diet, escape latency (time to reach the hidden platform) was determined in a 3-day cued trial block (four trials per day) followed by a 5-day hidden trial block (six trials per day). Day 9 was a probe trial, in which the time spent in the target quadrant (D) and number of platform crosses (E) were determined (total time of the trial was 60 s). Performance in the MWM task in a separate cohort of wild-type animals was compared to Aldh2$^{-/-}$ mice fed the D-PUFA diet for 2 weeks (F).

The effect of D-PUFAs preventing cognitive impairment and anxiety-like behavior in Aldh2$^{-/-}$ mice was studied. Three widely used and accepted tests of spatial and working memory to assess the effects of the D-PUFA diet on memory deficits in Aldh2$^{-/-}$ mice were used. The MWM task assessed spatial reference memory, spontaneous alternations in the Y-maze was a test for spatial working memory, and the open field NOR task assessed working memory in the absence of a reference memory component. The version of the MWM task used in this study consisted of 3 days of cued platform training, in which mice swim to a visible platform, followed by 5 days of testing in which the platform was hidden. There were no differences in latency times between the two diets for the cued platform training (FIG. 6A-C), when comparing with wildtype and Aldh2$^{-/-}$ mice. For the hidden platform trials, after 2 weeks on the D-PUFA or H-PUFA diet, there was a significant decrease in escape latency times for D-PUFA diet mice compared to H-PUFA diet mice on the fourth and fifth days of testing (blocks 7 and 8 in FIG. 6A). Differences in escape latencies became more marked after 10 or 18 weeks on the two diets (FIG. 6 B,C), and were significantly different on days 2, 3, 4, and 5 of testing (blocks 5-8). In the probe trial, mice fed the D-PUFA diet spent more time in the target quadrant (FIG. 6D) and had a greater number of platform crosses (FIG. 6E) compared to HPUFA diet mice after either 2, 10, or 18 weeks on the two diets.

FIG. 6A-6F show the superior performance in the Morris Water Maze task in Aldh2$^{-/-}$ mice fed the D-PUFA diet. Two weeks (A) 10 weeks (B), or 18 weeks (C) after the initiation of the D-PUFA or H-PUFA diet, escape latency (time to reach the hidden platform) was determined in a 3-day cued trial block (four trials per day) followed by a 5-day hidden trial block (six trials per day). Day 9 was a probe trial, in which the time spent in the target quadrant (D) and number of platform crosses (E) were determined (total time of the trial was 60 s). Performance in the MWM task in a separate cohort of wild-type animals was compared to Aldh2$^{-/-}$ mice fed the D-PUFA diet for 2 weeks (F). In (F), no significant differences were found at any trial block. In (A, B, C, and F), data are expressed as the mean±SEM of the average scores in each trial block (n=16 for D-PUFA, n=15 for H-PUFA, and n=20 for wild-type). In D and E, data are expressed as the mean±SD (n=16 for D-PUFA and n=15 for H-PUFA). In D, the dotted line represents the expected time that would be spent in any quadrant by chance alone. Data were analyzed by two-way ANOVA and a Bonferroni post-hoc test in (A, B, C, and F) and by Student's t-test for unpaired data in (D, E).

Changes in task performance over time in animals on each of the diets were evaluated. For mice on the H-PUFA diet, there were no differences in performance in any of the trial blocks over the 18-week study period. For animals on the D-PUFA diet, the only difference was a decrease in latency time in the first trial block (block 4) after 18 weeks on diet compared to that of mice after either 2 or 10 weeks on diet. In the probe trials, time in the target quadrant and number of platform crosses did not change over time for either of the groups. Thus, memory deficits in mice fed the H-PUFA diet, and task performance in mice fed the D-PUFA diet, remained stable for the duration of the study. Similarly, task performance in wild-type and Aldh2−/− mice fed a standard diet (Lab-Diet 5015 Mouse diet) remains stable in animals between 3 and 12 months of age.

In the open field NOR task (FIG. 7) and spontaneous alternations in the Y-maze (FIG. 8), Aldh2$^{-/-}$ mice fed the H-PUFA diet showed a progressive decrease in performance in both memory tasks, compared to a progressive increase in performance in mice on the D-PUFA diet. Performance in the NOR task was significantly different between the two groups after 10 and 18 weeks on diet, and in the Y-maze task after 18 weeks on diet. FIGS. 7A and 7B show superior performance in the in the novel object recognition (NOR) task in Aldh2$^{-/-}$ mice fed the D-PUFA diet. Male and female mice were subjected to the NOR task 2, 10, and 18 weeks after initiation of either the D-PUFA or H-PUFA diet, and the frequency of visits to the objects and the time spent exploring each object was recorded. (A) Ratio of time spent with the novel object in relation to the familiar object. (B) Discrimination index (difference in time exploring the novel and familiar object, divided by total exploration time). Data are presented as the mean±SD (n=16) and were analyzed by Student's t-test for unpaired data. FIG. 8 shows the superior performance in the Y-maze task by Aldh2$^{-/-}$ mice fed the D-PUFA diet. The spontaneous alternation rate in the Ymaze task was assessed in male and female mice 2, 10, and 18 weeks after initiation of either the D-PUFA or H-PUFA diet. Data are presented as means±s.d. (n=16) and were analyzed by Student's t-test for unpaired data.

The open field test was used to assess spontaneous locomotor activity during free exploration in a dimly lit environment, and revealed no differences between groups in total time moving (D-PUFA, 161±29 s; H-PUFA, 163±17 s, P>0.05, Student's t-test for unpaired data) or total distance travelled (D-PUFA, 83±20 m; H-PUFA, 83±18 m, P>0.05, Student's t-test for unpaired data).

The Light/Dark box test was used to assess aversion to bright illumination as a measure of anxiety-like behavior. Although both groups showed a preference for the dark chamber, in mice fed the D-PUFA diet for 10 weeks there was a significant increase in both time spent in the light side and total number of crosses between the light and dark sides, compared to mice on the H-PUFA diet (FIG. 9). The differences observed here between D-PUFA- and H-PUFA-fed mice were similar to those between wild-type and Aldh2$^{-/-}$ mice of a comparable age. FIG. 9 shows increased time spent in, and number of crosses into, the illuminated chamber of the Light/Dark Box by Aldh2$^{-/-}$ mice fed the D-PUFA diet for 10 weeks. Mice were placed into the dark side of the light/dark box chamber and allowed to explore for a 5-min period. The number of crosses between the light and dark sides of the chamber, and the total time spent in the light side were recorded. Data are presented as means±SD (n=16 for DPUFA and n=13 for H-PUFA) and were analyzed by Student's t-test for unpaired data.

Example 15

Deuterium-reinforced D-PUFAs were resistant to nonenzymatic LPO and have been shown to reduce oxidative stress in several experimental models. The present study evaluated whether alteration of lipid metabolism by a D-PUFA-enriched diet resulted in improvement of cognitive deficits in our model of oxidative stress induced cognitive impairment that exhibits AD-like pathological changes. Oral administration of the ethyl esters of D-PUFA (e.g., 11,11-D2-LA and 11,11,14,14-D4-ALA) markedly reduced LPO products in Aldh2$^{-/-}$ mice. This was associated with improved performance in three different memory tasks that assess both working and spatial memory, and also with a reduction in anxiety-like behavior.

The protocol for the MWM, in which a 3-day cued trial was followed by a 5-day hidden platform trial, provided a thorough assessment of spatial reference memory. The lack of differences between D-PUFA and H-PUFA-fed mice during the 3-day cued trial suggests that eyesight, swim speed, basic strategies, and motivation were the same in each treatment group. No nonspecific behavioral changes were observed such as floating or thygmotaxis in either group. Mice fed the D-PUFA diet performed significantly better in all measures of the hidden platform portion of MWM task after only 2 weeks on diet, with differences becoming more marked after 10 and 18 weeks on diet. In both the Y-maze NOR tasks, Aldh2$^{-/-}$ mice fed the H-PUFA diet showed progressive decreased in performance compared to progressive increases in performance in mice on the D-PUFA diet. In the Light/dark box test, mice fed the D-PUFA diet exhibited a reduction in the anxiety-like behavior that was seen in this model (aversion to bright illumination). Thus, reduction of nonenzymatic LPO by D-PUFAs had cognition-restoring properties in Aldh2$^{-/-}$ mice, and suggested that there are therapeutic opportunities afforded by oral dosing with D-PUFAs for the treatment of neurodegenerative diseases such as AD.

Although wild-type animals fed the D-PUFA or H-PUFA diets were not used in this study, when the performance of mice fed the D-PUFA diet for 2 weeks was compared to that of wild-type animals of a similar age, but fed LabDiet 5015 Mouse diet, no significant differences in escape latency were found at any trial block. Both diets contained 12% fat, but had differing amounts and ratios of linoleic and ALA. Thus, the D-PUFA diet prevented the loss in special reference memory performance that would otherwise occur in the Aldh2$^{-/-}$ mice. Furthermore, the differences in performance in all three memory tasks between mice fed the D-PUFA and H-PUFA diets for 8 weeks, were very similar to the differences between wild-type and Aldh2$^{-/-}$ mice of a comparable age, indicating that D-PUFAs essentially reset the performance of Aldh2$^{-/-}$ mice to that of wild-type mice.

Isotope ratio mass spectrometry indicated incorporation of deuterium into brain lipids, to an extent similar to that found in previous studies. This level of incorporation was sufficient to markedly reduce LPO products, as measured by the decrease in esterified F2-IsoPs, consistent with previous studies in yeast and mice. F2-IsoPs are derived from nonenzymatic oxidation of ARA. ARA can also undergo enzymatic oxidation to yield PGF2a as well as numerous other products catalyzed by cyclooxygenases and lipoxygenases.

Comparison of F2-IsoPs and PGF2a levels in the D-PUFA fed animals shows that there was a substantially greater reduction in nonenzymatic LPO than enzymatic lipid oxidation. That D-PUFAs also had an effect on enzymatic oxidation can be explained by the fact that 11,11-D2-LA is efficiently converted to 13,13-D2-ARA. The presence of deuterium at carbon 13 on ARA would be expected to influence both nonenzymatic and enzymatic oxidation since this is the site of action of the cyclooxygenase enzymes. Nonenzymatic oxidation is also influenced by the presence of other D-PUFAs in lipid membranes, slowing down the free radical chain reaction and resulting in a greatly decreased level of F2-IsoPs.

F2-IsoPs were recognized as reliable biomarkers of endogenous LPO by virtue of their ubiquitous nature, their chemical stability in biological fluids and tissues, and their amenability to quantitative GC/MS analysis, and were the measure used in the current study for assessment of nonenzymatic LPO, rather than the more semi-quantitative assessment afforded by immunoblot analysis of carbonyl protein adducts. In the context of AD progression, increased levels of F2-IsoPs and F4-NeuroPs were found in the frontal, parietal, and occipital lobes of subjects with amnesic mild cognitive impairment (MCI) relative to age-matched normal control subjects [35]. These levels were comparable to those found in subjects with late stage AD, suggesting that LPO of ARA and DHA is an early event that continues throughout the progression of AD. This was consistent with studies of individuals with MCI, early stage AD, and late stage AD which examined the formation of protein adducts of LPO derived reactive aldehydes such as IMF, and HUE. Given that HITE and HNE exhibit similar toxicities in cultured and that DHA, the predominant omega-3 PUFA in many brain regions, is 30-100% more abundant than ARA, the predominant omega-6 PUFA, raises the possibility that HHE protein adducts could contribute to reactive aldehyde-induced neuronal damage While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method of treating, inhibiting the progression of, or ameliorating Alzheimer's disease in a patient diagnosed with impaired aldehyde dehydrogenase-2 activity, comprising:
   administering to the subject patient an effective amount of a compound comprising a polyunsaturated fatty acid, a polyunsaturated fatty acid ester, a polyunsaturated fatty acid thioester, or a polyunsaturated fatty acid amide,
   wherein the polyunsaturated fatty acid, the polyunsaturated fatty acid ester, the polyunsaturated fatty acid thioester, or the polyunsaturated fatty acid amide is deuterated at one or more bis-allylic positions.

2. The method of claim 1, wherein the polyunsaturated fatty acid ester is an ethyl ester, triglyceride, diglyceride, or monoglyceride.

3. The method of claim 1, wherein the compound is deuterated at one or more bis-allylic positions and wherein the compound is a ω-3 or ω-6 fatty acid, ω-3 or ω-6 fatty acid ester, ω-3 or ω-6 fatty acid amide, ω-3 or ω-6 fatty acid thioester, or prodrug thereof.

4. The method of claim 3, wherein the compound is a linoleic acid, linolenic acid, arachidonic acid, eicosapentaenoic acid, docosahexaenoic acid, or their ester, amide, or thioester thereof.

5. The method of claim 1, wherein the compound comprises between about 1% and 100% of the total amount of polyunsaturated fatty acids or polyunsaturated fatty acid esters administered to or ingested by the patient.

6. The method of claim 5, wherein the amount of the compound is greater than 5% of the total amount of polyunsaturated fatty acids or polyunsaturated fatty acid esters administered to or ingested by the patient.

7. The method of claim 1, wherein the compound is selected from the group consisting of 11,11-D2-linolenic acid, 14,14-D2-linolenic acid, 11,11,14,14-D4-linolenic acid, 11,11-D2-linoleic acid, 14,14-D2-linoleic acid, 11,11,14,14-D4-linoleic acid, deuterated alpha linolenic acid, deuterated gamma linolenic acid, deuterated dihomo gamma linolenic acid, deuterated arachidonic acid, deuterated docosatetraenoic acid, deuterated eicosapentaenoic acid, or deuterated docosahexaenoic acid.

8. The method of claim 1, wherein the compound is administered with an antioxidant.

9. The method of claim 8, wherein the antioxidant is Coenzyme Q, idebenone, mitoquinone, mitoquinol, vitamin E, vitamin C, or any combination thereof.

10. The method of claim 1, wherein the compound is administered with one or more oxylipin.

11. The method of claim 10, wherein the oxylipin is a prostaglandin.

12. The method of claim 1, wherein the Alzheimer's disease is associated with a mutated form of aldehyde dehydrogenase-2.

13. The method of claim 1, wherein the compound comprises 11,11, D2-linolenic acid.

14. The method of claim 1, wherein the compound comprises 14,14, D2-linolenic acid.

15. The method of claim 1, wherein the compound comprises 11,11,14,14, D4-linolenic acid.

16. The method of claim 1, wherein the compound comprises 11,11, D2-linoleic acid.

17. The method of claim 1, wherein the compound comprises 14,14, D2-linoleic acid.

18. The method of claim 1, wherein the compound comprises 11,11,14,14, D4-linoleic acid.

19. The method of claim 1, wherein the compound comprises deuterated alpha linolenic acid.

20. The method of claim 1, wherein the compound comprises deuterated arachidonic acid.

21. The method of claim 1, wherein the compound comprises deuterated eicosapentaenoic acid.

22. The method of claim 1, wherein the compound comprises deuterated docosahexanenoic acid.

23. The method of claim 1, wherein the patient diagnosed with impaired aldehyde dehydrogenase-2 activity is identified as having the E487K variant of aldehyde dehydrogenase-2.

24. The method of claim 1, wherein the method includes diagnosing the patient diagnosed with impaired aldehyde dehydrogenase-2 activity as having an aldehyde dehydrogenase-2 gene mutation or deletion.

25. The method of claim 1, wherein the polyunsaturated fatty acid, polyunsaturated fatty acid ester, polyunsaturated fatty acid thioester, or polyunsaturated fatty acid amide is further deuterated at one or more pro-bis-allylic positions.

26. The method of claim 24, wherein the method further includes diagnosing the patient diagnosed with impaired aldehyde dehydrogenase-2 activity as having the heterozygous ALDH2*1/2*2 genotype.

27. The method of claim 24, wherein the method further includes diagnosing the patient diagnosed with impaired aldehyde dehydrogenase-2 activity as having the heterozygous ALDH2*2/2*2 genotype.

* * * * *